United States Patent
Won et al.

(10) Patent No.: US 11,701,378 B2
(45) Date of Patent: Jul. 18, 2023

(54) RNA AND NUCLEIC ACID CARRIER INCLUDING THE SAME

(71) Applicant: LEMONEX INC., Seoul (KR)

(72) Inventors: Cheol Hee Won, Seoul (KR); Jun Kim, Seoul (KR)

(73) Assignee: LEMONEX INC., Seoul (KR)

( * ) Notice: Subject to any disclaimer, the term of this patent is extended or adjusted under 35 U.S.C. 154(b) by 0 days.

(21) Appl. No.: 17/533,533

(22) Filed: Nov. 23, 2021

(65) Prior Publication Data

US 2022/0143068 A1    May 12, 2022

Related U.S. Application Data

(63) Continuation of application No. PCT/KR2021/008530, filed on Jul. 5, 2021.

(60) Provisional application No. 63/048,072, filed on Jul. 3, 2020.

(30) Foreign Application Priority Data

Jul. 5, 2021 (KR) ........................ 10-2021-0088160

(51) Int. Cl.
| | |
|---|---|
| *A61K 31/7105* | (2006.01) |
| *A61K 47/69* | (2017.01) |
| *A61K 47/54* | (2017.01) |
| *A61P 35/00* | (2006.01) |
| *A61K 31/713* | (2006.01) |
| *B82Y 5/00* | (2011.01) |
| *B82Y 30/00* | (2011.01) |
| *B82Y 40/00* | (2011.01) |

(52) U.S. Cl.
CPC ........ *A61K 31/7105* (2013.01); *A61K 31/713* (2013.01); *A61K 47/549* (2017.08); *A61K 47/6923* (2017.08); *A61P 35/00* (2018.01); *B82Y 5/00* (2013.01); *B82Y 30/00* (2013.01); *B82Y 40/00* (2013.01); *C12N 2310/351* (2013.01)

(58) Field of Classification Search
CPC .............. A61K 31/7105; A61K 31/713; A61K 47/549; A61K 47/6923; A61P 35/00; B82Y 5/00; B82Y 30/00; B82Y 40/00; C12N 2310/351
USPC ....................................................... 514/44 A
See application file for complete search history.

(56) References Cited

U.S. PATENT DOCUMENTS

| | | | |
|---|---|---|---|
| 8,389,708 B2 | 3/2013 | Min | |
| 2018/0142239 A1* | 5/2018 | Yu | ........................... A61P 35/00 |

FOREIGN PATENT DOCUMENTS

| | | | | |
|---|---|---|---|---|
| KR | 10-2018-0091768 A | 8/2018 | | |
| WO | WO 2014/039961 A1 | 3/2014 | | |
| WO | WO-2015084897 A2 * | 6/2015 | ............. | A61K 35/15 |
| WO | WO-2017210647 A1 * | 12/2017 | ......... | A61K 31/7088 |

OTHER PUBLICATIONS

Na et al. Small, 2012, vol. 8, No. 11, pp. 1752-1761. (Year: 2012).*
Na, Hee-Kyung et al., "Efficient functional delivery of siRNA using mesoporous silica nanoparticles with ultralarge pores", Small, 2012, pp. 1752-1761, vol. 8(11), Wiley-VCH Verlag GmbH & Co. KGaA, Weinheim.
Zhang, Qifang et al. "TLR9-mediated siRNA delivery for targeting of normal and malignant human hematopoietic cells in vivo", Blood, Feb. 21, 2013, pp. 1304-1315, vol. 121 (8), The American Society of Hematology.

* cited by examiner

*Primary Examiner* — Janet L Epps-Smith
(74) *Attorney, Agent, or Firm* — The PL Law Group, PLLC

(57) ABSTRACT

A nucleic acid carrier according to an embodiment of the present disclosure includes CpG-ODN-RNA conjugate and a porous silica particle carrying the conjugate inside pores thereof. In this regard, the nucleic acid carrier of the present invention can stably deliver loaded nucleic acid molecules to a body and release the same to a target, thereby increasing Type 1 interferon and exhibiting RNA-inherent functions.

16 Claims, 36 Drawing Sheets

Specification includes a Sequence Listing.

2 L scale 10 L scale

DDV(300)$_{17}$

DDV(300)$_{17}$-NH$_2$

$t_{50\%}$ = about 2.5 days

FIG. 13A

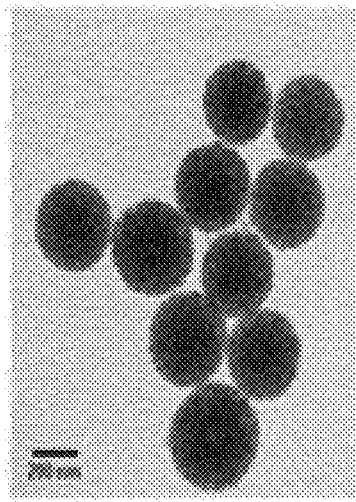

FIG. 13B

| | Sequence of CpG ODN-siIDO for LEM-S403 | |
|---|---|---|
| Human | 5'ggGGGACGA:TCGTCgggggg*-carbon linker-siIDO1#-3' | SEQ ID NO: 38 |
| | 5'-AGCUGCUUCUGCAAUCAAAGUAAU-3'# | SEQ ID NO: 34 |
| | 5'-AUUACUUUGAUUGCAGAAGCAGCU-3'# | SEQ ID NO: 35 |
| Mouse | 5'ggGGTCAAC:GTTGAgggggg*-carbon linker-siIDO1#-3' | SEQ ID NO: 39 |
| | 5'-GGGCUUCUUCCUCGUCUCU-3'# | SEQ ID NO: 36 |
| | 5'-AGAGACGAGGAAGAAGCCC-3'# | SEQ ID NO: 37 |

*DNA #RNA, Palindrome is underlined
Capital letter: phosphodiester, non-capital letter: phosphorothioate.
Carbon linker: C6-linker

**CT26 syngeneic mouse
(tumor volume around 100 mm³)**

% of Treg cells in Tumors

RNA AND NUCLEIC ACID CARRIER INCLUDING THE SAME

PRIORITY

The present application is a continuation application to International Application No. PCT/KR2021/008530 with an International Filing Date of Jul. 5, 2021, which claims the benefit of U.S. Patent Applications No. 63/048,072 filed on Jul. 3, 2020 and Korean Patent Applications No. 10-2021-0088160 filed on Jul. 5, 2021 at the Korean Intellectual Property Office, the disclosures of which are incorporated by reference herein in their entirety.

BACKGROUND

1. Technical Field

The present invention relates to RNA and a nucleic acid carrier including the same.

2 Background Art

Tumor can construct a barrier against immune response using indoleamine 2,3-dioxegenase (IDO). The IDO is basically an enzyme used by a fetal to avoid rejection of a pregnant mother, which involves strong regulatory T cells (Tregs) to suppress immune response. Tregs are immune cells playing a key role in preventing auto-immune diseases such as rheumatoid arthritis or Type 1 diabetes. However, Tregs involved by tumor cells are more attackable than Tregs existing in other portions of a human body while having excellent inhibitory ability. Despite cancer patients have a large amount of activated tumor-specific T cells, tumor cannot be eliminated in a number of cases. The reason is that Tregs suppress tumor-specific CTL (CD8T cytotoxic) cells and Th (CD4 helper) cells, whereby the cancer may avoid attack of the immune system. Accordingly, suppressing IDO may improve cancer treatment effects.

SUMMARY

An object of the present invention is to provide a nucleic acid molecule including siRNA to inhibit expression of a gene relevant to immunity or a disease.

In addition, another object of the present invention is to provide a nucleic acid molecule further including CpG oligodeoxynucleotide (CpG-ODN).

Further, another object of the present invention is to provide a nucleic acid delivery system ("carrier") loaded with nucleic acid molecules including siRNA and CpGODN.

Furthermore, another object of the present invention is to provide a pharmaceutical composition for prevention or treatment of cancer.

To achieve the above objects, the following technical solutions are adopted in the present invention.

1. A nucleic acid carrier, including CpG-ODN-RNA conjugate and a porous silica particle carrying the same inside pores thereof, wherein the porous silica particle has an average pore diameter of 7 to 30 nm.

2. The nucleic acid carrier according to the above 1, wherein the RNA is mRNA, tRNA, miRNA, snRNA, snoRNA, aRNA, siRNA, circular RNA or piRNA.

3. The nucleic acid carrier according to the above 1, wherein the RNA is indoleamine 2,3-dioxygenase (IDO) siRNA.

4. The nucleic acid carrier according to the above 1, wherein the CpG-ODN and RNA are coupled through a linker.

5. The nucleic acid carrier according to the above 4, wherein the linker is saturated alkyl chains (C3 to C18), triazole linker or 4-methyl-6,7,8,9,10,10a-hexahydro-5H-3λ2-cycloocta[d]pyridazine linker.

6. The nucleic acid carrier according to the above 3, wherein the IDO siRNA includes siRNA of SEQ ID NOs: 1 and 2; siRNA of SEQ ID NOs: 3 and 4; siRNA of SEQ ID NOs: 5 and 6; siRNA of SEQ ID NOs: 7 and 8; or siRNA of SEQ ID NOs: 9 and 10.

7. The nucleic acid carrier according to the above 3, wherein the siRNA further includes a sequence of 1 to 10 nt complementary to IDO mRNA at N terminal or C terminal.

8. The nucleic acid carrier according to the above 3, wherein the IDO siRNA includes siRNA of SEQ ID NOs: 11 and 12.

9. The nucleic acid carrier according to the above 1, wherein the CpG-ODN is CpG-A ODN, CpG-B ODN or CpG-C ODN.

10. The nucleic acid carrier according to the above 1, wherein the CpG-ODN includes any one nucleotide among SEQ ID NOs: 13 to 15.

11. The nucleic acid carrier according to the above 1, wherein the porous silica particle is positively charged inside the pores.

12. The nucleic acid carrier according to the above 1, wherein the porous silica particle has zeta potential of 5 to 80 mV before loading of the conjugate.

13. The nucleic acid carrier according to the above 1, wherein a weight ratio of the conjugate and the particle ranges from 1:1 to 20.

14. The nucleic acid carrier according to the above 1, wherein a BET surface area of the particle ranges from 200 to 700 m$^2$/g, and a particle diameter ranges from 50 to 1000 nm.

15. A pharmaceutical composition for prevention or treatment of cancer, including the nucleic acid carrier according to the above 1, wherein the RNA is indoleamine 2,3-dioxygenase siRNA (IDO).

16. The pharmaceutical composition according to the above 15, wherein the cancer is selected from ovarian cancer, cervical cancer, follicle cysts, gynecologic cancer, urologic cancer, renal cancer, testicular cancer, penile cancer, genitourinary tract cancer, testicular tumor, bladder cancer, skin cancer, sarcoma, osteosarcoma, malignant bone tumor, soft tissue sarcoma, keratoacanthoma, melanoma, lung cancer, small cell lung carcinoma, non-small cell lung carcinoma (NSCLC), lung adenocarcinoma, squamous cell carcinoma of the lung, papillary cancer, breast cancer, triple negative breast cancer (TNBC), breast endocrine cancer, hepatobiliary and pancreatic cancer, liver cancer, cholangiocarcinoma, gallbladder cancer, bile duct cancer, pancreatic cancer, bone cancer, bone marrow disorder, lymphatic disorder, hair cell cancer, oral and pharyngeal (oral) cancer, lip cancer, tongue cancer, oral cancer, salivary gland cancer, pharyngeal cancer, laryngeal cancer, esophageal cancer, gastric cancer, gastrointestinal cancer, small intestine cancer, colon cancer, rectal cancer, prostate cancer, vulvar cancer, thyroid cancer, large intestine cancer, endometrial cancer, uterine cancer, brain cancer, glioma, non-glioma tumor, malignant glioma, metastatic brain cancer, brain parenchyma, vestibular schwannoma, pituitary tumor, head and neck cancer, central nervous system cancer, peritoneal cancer, hepatocellular carcinoma, head cancer, neck cancer, primary tumor, metastatic tumor, lymphoma, squamous cell carcinoma, hematologic malignancy, endocrine cancer, Hodgkin disease or leukemia.

17. RNA including sequences below:
   (1) siRNA of SEQ ID NOs: 1 and 2,
   (2) siRNA of SEQ ID NOs: 3 and 4,
   (3) siRNA of SEQ ID NOs: 5 and 6,
   (4) siRNA of SEQ ID NOs: 7 and 8, or
   (5) siRNA of SEQ ID NOs: 9 and 10.

18. The RNA according to the above 17, wherein the siRNA further includes a sequence of 1 to 10 nt complementary to IDO mRNA at N terminal or C terminal.

19. The RNA according to the above 17, wherein the RNA consists of siRNA of SEQ ID NOs: 11 and 12.

20. The RNA according to the above 17, wherein the RNA further includes CpG-ODN coupled to N terminal or C terminal thereof.

21. The RNA according to the above 20, wherein the CpG-ODN is CpG-A ODN, CpG-B ODN or CpG-C ODN.

22. The RNA according to the above 20, wherein the CpG-ODN includes any one nucleotide among SEQ ID NOs: 13 to 15.

23. The RNA according to the above 20, wherein CpG-ODN and siRNA are coupled through a linker.

24. The RNA according to the above 23, wherein the linker is saturated alkyl chains (C3 to C18), triazole linker or 4-methyl-6,7,8,9,10,10a-hexahydro-5H-3$\lambda$2-cycloocta[d]pyridazine linker.

The nucleic acid molecule including RNA according to the present invention may inhibit expression of indoleamine 2,3-dioxygenase (IDO) with high efficiency.

The nucleic acid molecule including RNA and CpG-ODN according to the present invention may increase Type 1 interferon and exhibit RNA-inherent function thereof.

The nucleic acid carrier of the present invention may stably deliver loaded nucleic acid molecules to a body and release the same to a target, so as to increase Type 1 interferon while exhibiting RNA-inherent function thereof.

The composition of the present invention may represent excellent anticancer activity.

BRIEF DESCRIPTION OF THE DRAWINGS

FIGS. 13A and 13B illustrate analyzed results of characteristics of porous silica particles (LEM-S403) loaded with nucleic acid molecules according to an embodiment of the present invention. FIG. 13A indicates physical properties (surface area, pore size, zeta potential, average size, pore size and loading capacity) as well as TEM image of DegradaBALL optimized for CpG-ODN-siIDO delivery, the bar on the left bottom of FIG. 13A indicates a length of 200 nm, and FIG. 13B shows LEM-S403 sequence for human and animal research.

FIG. 13C indicates a loading capacity of CpG-ODN-siIDO loaded in different amounts of DegradaBALL. Wherein, the loading capacity was about 90% CpG-ODN-siIDO loaded in DegradaBALL at room temperature within 30 minutes when a weight ratio was 1:5 (Cargo to DegradaBALL). FIG. 13D indicates a cumulative release kinetic profile of LEM-S403 in a bio-similar solution at 37° C. FIG. 13E shows knock-down of IDO1 by LEM-S403 in A549 cells and CT26 tumor through RT-PCR. Further, FIG. 13F illustrates cell absorption efficiency tests of LEM-S403 in mouse PBMC, wherein the mouse PBMC is separated, and then, treated with buffer, CpG-ODN-siIDO (FITC) (100 nM) or CpG-ODN-siIDO (FITC) with DegradaBALL (100 nM), respectively, for 6 hours. Herein, a loading efficiency of CpG-ODN-siIDO (FITC) was analyzed by flow cytometry. Further, FIG. 13H illustrates quantitative analysis of intracellular CpG-ODN-siIDO (FITC) in plasmacytoid dendritic cells (pDC) and non-pDC of PBMC based on gated results of the above f. Data (n=3 for each group) is represented by average±SD (***P<0.001 vs other groups).

FIG. 14B illustrates long-term IDO1 gene knock-down efficiency of LEM-S403 in A549 cells. For comparison, the cells were treated with 150 nM LEM-S403 and CpG-ODN-siIDO loaded in LNP, respectively. The cells were cultured for 24, 48 and 72 hours, respectively, along with IFN-γ induction for 12 hours. Comparison between groups was conducted by one-way ANOVA. p<0.01 and *P<0.001. FIG. 14C illustrates analyzed results of secreted Type I IFN present in the supernatant using HEK-BLUE™ INF-a/b cells after treating human PMBC with LEM-S403 at different concentrations (7.82, 15.63, 31.25, 62.5, 125, 250 and 500 nM), respectively, for 12 hours. Graphs are represented by average±SEM per group, n=3. FIG. 14D** illustrates analyzed results of secreted Type I IFN present in the supernatant using supernatant using HEK-BLUE™ INF-a/b cells after treating human PMBC with siIDO (125 nM) with or without DegradaBALL, CpG-ODN (125 nM) and CpG-ODN-siIDO (125 nM), respectively, and then further culturing the cells for 22 hours. Data (n=4 for each group) is represented by average±SD. Comparison between groups was conducted by one-way ANOVA. *p<0.05, p<0.01 and *p<0.001 vs non-treated group. FIG. 14E illustrates Type I FN induction test for LEM-S403 using human PMBC in five (5) different arrangements. Data (n=5 for each group) is represented by average±SD. Comparison between groups was conducted by one-way ANOVA. *p<0.05.

FIG. 15A shows a treatment schedule for tumor imaging and flow cytometry tests. In the tumor imaging test, the mice were treated with buffer, 70 μg of DegradaBALL (TAMRA), 14 μg of CpG-ODN-siIDO (Cy5) or 14 μg of LEMIDO (CpG-ODN-siIDO (Cy5) with DegradaBALL (TAMRA)), respectively. Day 1 and day 3 after treatment, tumor was separated for ex vivo imaging and immunofluorescence staining. In the flow cytometry test, the mice were treated with 70 μg of DegradaBALL, 14 μg of CpG-ODN-siIDO (FITC) or LEMIDO (CpG-ODN-siIDO (Cy5) with DegradaBALL (TAMRA)), respectively. Day 1 and day 3 after treatment, tumor and lymph node were separated for flow cytometry. FIG. 15B shows a sustained release profile of CpG-ODN-siIDO coupled or not coupled with DegradaBALL. FIG. 15C illustrates histological cross-sectional images of tumor tissues to demonstrate distributions of dendritic cells (cd11c), DegradaBALL and CpG-ODN-siIDO, respectively.

FIG. 15D illustrates time-dependent inclusion of CpG-ODN-siIDO (FITC) (day 1 and day 3) in total cells of lymphocytes, non-lymphocytes (mainly tumor cells) and tumor. The percentage of FITC-conjugated CpG-ODN-siIDO was determined by flow cytometry. Data (n=3 mice per group) is represented by average±SD. Comparison between two groups was conducted by student's t-test (two-tailed). *p<0.05 and *p<0.001. FIG. 15E illustrates time-dependent inclusion of CpG-ODN-siIDO (FITC) (day 1 and day 3) in draining lymph nodes. Comparison between two groups was conducted by student's t-test (two-tailed). *p<0.001.

FIG. 16A shows a treatment schedule and table summarizing administration route and dosage per injection (active pharmaceutical ingredient (API) and DegradaBALL) in regard to aPD-1ab, CpG-ODN-siIDO and LEM-S403. FIG. 16B illustrates a tumor growth curve using an average tumor volume in CT26 syngeneic mouse model (n=6 mice per group). Data is represented by average±SEM. Comparison between two groups was conducted by student's t-test (two-tailed). *p<0.05, p<0.01 and *p<0.001 vs vehicle group. FIG. 16C illustrates percentages for survival of mice treated with buffer, vehicle, aPD-1 Ab, CpG-ODD+vehicle, siIDO+vehicle, LEM-S403 (3.5/7/14 μg) or LEM-S403 (14 μg) with aPA-1 ab, respectively. It was demonstrated that resulting values are considerably different from those of buffer, vehicle, aPD-1 ab, CpG-ODN+vehicle, siIDO+vehicle and LEM-S403 3.5 μg groups (p<0.01, log-rank Mantel-Cox test). FIG. 16D shows a table summarizing administration route and dosage per injection (active pharmaceutical ingredient (API) and DegradaBALL) in regard to aPD-1 ab, aCTLA-4 ab and LEM-S403. FIG. 16E** shows a tumor growth curve to average tumor volume in CT26 syngeneic mouse model (n=6 mice per group). Data is represented by average±SEM. Comparison between two groups was conducted by student's t-test (two-tailed). *p<0.05, p<0.01 and *p<0.001 vs vehicle group. #p<0.05 and ##p<0.01 vs LEM-S403 group. FIG. 16F illustrates percentages for survival of the mice according to FIG. 16E. It was demonstrated that the resulting values are considerably different from those of LEM-S403 group (***p<0.001, log-rank Mantel-Cox test).

FIG. 16G shows a treatment schedule for anti-tumor mechanism test of LEM-S403 in CT26 syngeneic mouse model. In this case, the mice were treated twice with buffer, vehicle, CpG-ODN+vehicle, siIDO+vehicle or LEM-S403 on day 0 and day 3, respectively, and then, 24 hours after the last treatment, each mouse was sacrificed. As shown in FIG. 16H, a ratio of cells in tumor was determined by flow cytometry after double staining using Annexin V and PI. Data is represented by average±SD (n=6 mice per group). Comparison between groups was conducted by one-way ANOVA. *p<0.05, p<0.01 and *p<0.001 vs buffer, vehicle and CpG-ODN+vehicle group. #p<0.05 vs siIDO+vehicle group. FIG. 16I illustrates TUNEL staining of tumor fragments. A scale-bar indicates 100 μm. FIG. 16J illustrates immunofluorescence staining of phospho-STAT1, IDO1 and Kynurenine, respectively, in tumor. FIG. 16K shows quantitative data of fluorescent signals based on images shown in FIG. 16J. Data is represented by average±SD (n=3 mice per group). Comparison between groups was conducted by one-way ANOVA. *p<0.001. On day 1 and day 4, mRNA expression levels of IDO1 were measured through RT-PCR. Data is represented by average±SD (n=3 mice per group). Comparison between groups was conducted by one-way ANOVA. *p<0.001.

FIG. 17A shows a treatment schedule for anti-tumor immune response analysis in the above model. FIG. 17B illustrates a maturation frequency of dendritic cells in tumor micro-environment (TME) and draining lymph nodes (dLNs) 24 hours after last treatment. Data is represented by average±SD (n=5 mice per group). Comparison between groups was conducted by one-way ANOVA. *p<0.05, p<0.01 and *p<0.001 vs buffer group. FIG. 17C is a representative flow cytometric graph showing CD86 in TME.

FIGS. 17D and 17E illustrate immune cell infiltration and immunofluorescence staining of NK 1.1+ cells and NK1.1+CD69+ cells, respectively, in tumor. Comparison between two groups was conducted by one-way ANOVA. *p<0.05, p<0.01 and *p<0.001. FIGS. 17F and 17G illustrate immune cell infiltration and immunofluorescence staining of CD8+ cells and CD8+CD69+ cells, respectively, in tumor. Comparison between two groups was conducted by one-way ANOVA. *p<0.05, p<0.01 and *p<0.001. FIG. 17H shows Treg cell frequency in tumor 24 hours after last treatment. Comparison between two groups was conducted by one-way ANOVA. *p<0.001. FIG. 17I shows CD8/Treg cell ratio in tumor. Comparison between two groups was conducted by one-way ANOVA. *p<0.001.

FIG. 18A shows a treatment schedule for assessment of abscopal effects in the model. Mice received administration of buffer, vehicle, aPD-1 ab, CpG-ODN+vehicle, siIDO+vehicle, LEM-S403 (14 µg), LEM-S403 (14 µg) with aPD-1 ab or LEM-S403 (14 µg) with aCTLA-4 ab, respectively, four (4) times at an interval of 3 to 4 days. FIG. 18B illustrates a terminal tumor (non-injection) growth curve involving relative average tumor volumes of Balb/c mice (n=6 mice per group). Data is represented by average±SEM. Comparison between two groups was conducted by student's t-test (two-tailed). *p<0.05, p<0.01 and *p<0.001 vs vehicle group. #p<0.05 vs LEM-S403 group. FIG. 18C shows a treatment schedule for analysis of anti-tumor activity and tumor infiltration lymph nodes (TIL) in remote tumors.

FIG. 18D illustrates TUNEL staining of excised remote tumor, wherein a scale-bar indicates 100 µm. FIG. 18E shows the number of cells in regard to leukocytes, neutrophils and lymphocytes, wherein the number of cells in regard to circulating leukocytes, neutrophils and lymphocytes was determined using Hemavet in whole blood. Data (n=5 mice per group) is represented by average±SD. Comparison between two groups was conducted by student's t-test (two-tailed). *p<0.05 vs buffer group. FIGS. 18F to 18H are results of analyzing immune cell groups (f, NK1.1+ cells and NK1.1+CD69+ cells; g, CD8+ cells and CD8+CD69+ cells; h, Treg cells) through flow cytometry. Comparison between two groups was conducted by one-way ANOVA. *p<0.05 and ***p<0.001.

DETAILED DESCRIPTION

Figure 1:
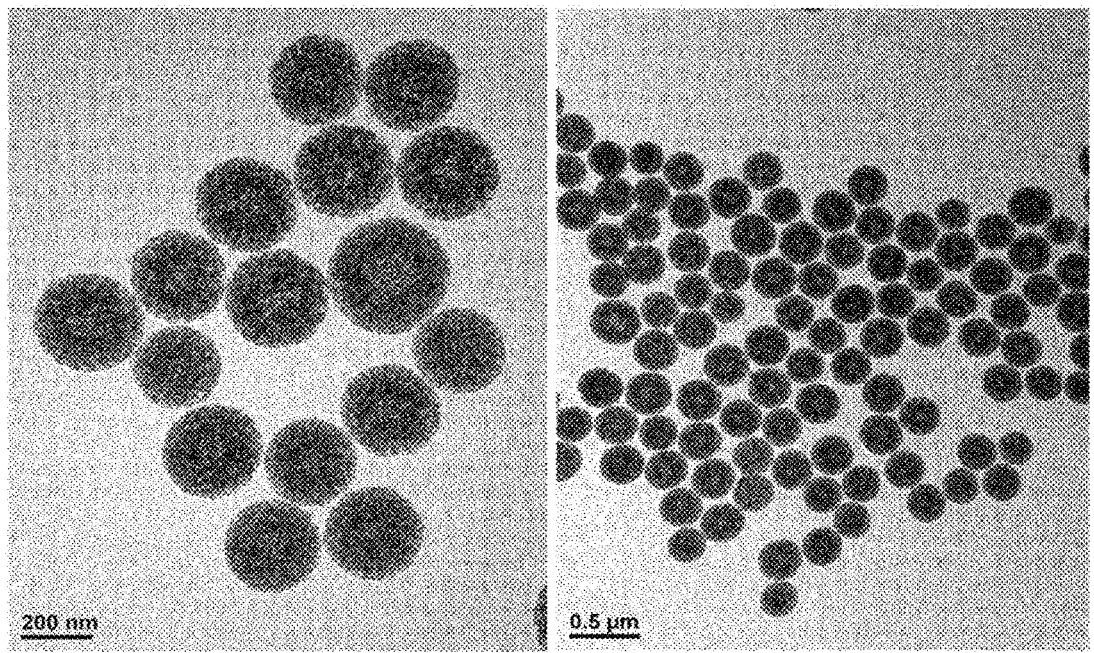
FIG. 1 is micrographs of porous silica particles according to one embodiment of the present invention.

Hereinafter, the present invention will be described in detail.

The present invention relates to a nucleic acid carrier.

A nucleic acid carrier of the present invention may include CpG-ODN-RNA conjugate and a porous silica particle loaded with the same in pores thereof.

The CpG-ODN-RNA conjugate may be a conjugate of CpG-ODN (oligodeoxynucleotide) and RNA. CpG-ODN is a synthetic short and single stranded oligonucleotide including unmethylated CpG dinucleotide. The oligonucleotide containing unmethylated CpG dinucleotide may be a nucleic acid molecule including an unmethylated cytosine-guanidine dinucleotide sequence (that is, "CpG DNA" or DNA in which 3' guanidine is linked to 5'cytosine and coupled thereto through a phosphate bond) and activating an immune system. Although the whole CpG oligonucleotide may not be methylated or may not be partially methylated, at least C in 5'CG 3' should not be methylated. The term "CpG oligonucleotide" or "CpG nucleic acid" as used herein may refer to an immune-stimulating CpG oligonucleotide or nucleic acid, unless otherwise stated herein.

As CpG-ODN is conjugated, Type 1 interferon may be increased.

Classes of CpG-ODN are not particularly limited, for example, may include class A, B or C, and preferably class A (CpG-A ODN). Class A (CpG-A ODN) is preferably used in an aspect of Type 1 IFN induction.

As CpG-ODN, any sequence known in the art may be used without limitation thereto. For example, sequences including SEQ ID NOs: 13 to 15. Specifically, the sequence SEQ ID NO: 13 may be used.

CpG-ODN may have a length of, for example, 10 to 100 nt, 10 to 80 nt, 10 to 50 nt, 15 to 80 nt, 15 to 50 nt, 10 to 40 nt, 10 to 30 nt, 15 to 40 nt, 15 to 30 nt, 10 to 25 nt, 15 to 25 nt or 20 to 25 nt, but it is not limited thereto.

CpG-ODN may be coupled to RNA through a linker. The linker may use any one known in the art without limitation thereto. For example, saturated alkyl chains (C3 to C18), a triazole linker, 4-methyl-6,7,8,9,10,10a-hexahydro-5H-3λ2-cycloocta[d]pyridazine linker, etc. may be used. In aspects of in vivo additional reaction and minimum side effects, saturated alkyl chains are preferably used. The saturated alkyl chains used herein may include C3 to C18, C3 to C15, C3 to C12, C3 to C10, C4 to C15, C4 to C12, C4 to C10, C4 to C8, C5 to C15, C5 to C12, C5 to C10, C3 to C8, C3 to C6, or C4 to C6 chains. Since CpG ODN and RNA are strongly coupled through a linker, side effects due to use of CpG ODN, that is, a problem of recruiting Treg cells may not occur.

RNA may include any one without limitation as long as it is required to be delivered. For example, mRNA, tRNA, miRNA, snRNA, snoRNA, aRNA, siRNA, circular RNA or piRNA may be used. For example, RNA having pharmacological activity may be used.

Specifically, RNA may be IDO siRNA.

RNA may be coupled to 5' terminal or 3' terminal of CpG-ODN.

Indoleamine 2,3-dioxygenase (IDO) may be IDO1 or IDO2. IDO siRNA may target human IDO mRNA or dog IDO mRNA. For example, mRNA SEQ ID NO: 32 (human IDO1 mRNA) or mRNA SEQ ID NO: 33 (dog IDO1 mRNA) may be targeted.

IDO siRNA is not particularly limited in terms of sequence, length, etc. as long as it can inhibit expression of IDO mRNA. For example siRNA SEQ ID NOs: 1 and 2, siRNA SEQ ID NOs: 3 and 4, siRNA SEQ ID NOs: 5 and 6, siRNA SEQ ID NOs: 7 and 8, or siRNA SEQ ID NOs: 9 and 10 may be included. Further, in an aspect of expression rate, siRNA SEQ ID NOs: 5 and 6, siRNA SEQ ID NOs: 7 and 8, or siRNA SEQ ID NOs: 9 and 10 are preferably included.

IDO siRNA may further include a base having a length of 1 to 10 nt, which is coupled to N terminal or C terminal. Such a length extension may be performed to enhance stability. The additionally added base may be used without limitation as long as the base does not inhibit expression inhibitory efficiency to a target mRNA. For example, the base may be a complementary base to the target. Further, the base may have a length of 1 to 10 nt, 1 to 8 nt, 1 to 6 nt or the like. For example, siRNA SEQ ID NOs: 11 and 12 may be used.

RNA may have a length of, for example, 10 to 50 nt, 10 to 30 nt, 10 to 25 nt, 15 to 25 nt, 17 to 25 nt, 18 to 25 nt, 17 to 23 nt, 18 to 23 nt, or the like, but it is not limited thereto.

The conjugate may further have a functional group which can be combined with porous silica particle at one end or both ends of CpG ODN or RNA. In biological and/or chemical fields, functional groups capable of coupling to each other or a compound containing the same may be applicable without limitation thereto. Further, the functional group to be coupled may be used in the conjugate and inside pores of particle, whereby due to coupling between functional groups, the conjugate may be loaded in the porous silica particles.

The porous silica particles are used to load the conjugate inside the pores. The conjugate is loaded inside the pores, thereby being protected from the external environment.

Further, CpG-ODN and RNA are loaded in a conjugate form inside the pores. Therefore, as compared to a case where CpG-ODN only is loaded and delivered, Treg cell collection inhibitory effects may be achieved. Further, as compared to another case where RNA only is loaded and delivered, immune improvement effects may be exhibited by use of CpG-ODN. Further, as compared to even a further case where both of the above two materials are loaded and delivered, respectively, the Treg cell group may be further reduced, thereby having a higher CD8/Teg ratio in tumor.

The porous silica particles of the present invention are particles based on silica ($SiO_2$) material and have a nano-scale particle size.

The porous silica nanoparticles are porous particles, each of which has nano-scale pores, and may carry nucleic acid molecules on an outer surface thereof and/or an inside of the pores.

The porous silica particles may have an average pore diameter of 7 to 30 nm.

The average pore diameter is within the above range, for example, 7 to 25 nm. Within the above range, it may be, for example, 7 to 25 nm, 7 to 23 nm, 10 to 25 nm, 13 to 25 nm, 7 to 20 nm, 7 to 18 nm, 10 to 20 nm, 10 to 18 nm, 12 to 18 nm, 12 to 16 nm, 14 to 18 nm, 14 to 16 nm, 15 to 16 nm, but it is not limited thereto.

The porous silica particles may have the above average pore diameter, thereby sufficiently loading the nucleic acid molecules inside the pores and delivering the same.

The porous silica particles may be positively charged inside the pores, and may have a zeta potential of 5 to 80 mV. Within the above range, the zeta potential may be, for example, 5 to 80 mV, 5 to 70 mV, 5 to 60 mV, 5 to 55 mV, 10 to 80 mV, 10 to 70 mV, 10 to 60 mV, 10 to 55 mV, 20 to 80 mV, 20 to 70 mV, 20 to 60 mV, 20 to 55 mV, 30 to 80 mV, 30 to 70 mV, 30 to 60 mV, 30 to 55 mV, 40 to 80 mV, 40 to 70 mV, 40 to 60 mV, 40 to 55 mV, 50 to 80 mV, 50 to 70 mV, 50 to 60 mV, 50 to 55 mV, etc., but it is not limited thereto.

When the charged particles are absorbed into a target cell (e.g., through a process such as Endocytosis), the particles entering the cell may have a strong positive charge due to low pH in endosome, which may induce osmosis due to diffusion of water passing a membrane of the endosome, thereby leading to formation of vacuoles.

When the particles have a strong positive charge, the cell membrane is wider than when it wraps around the particles, whereby extracellular fluid out of the particles or foreign substances such as various proteins contained therein may be introduced into the target cell together. In such a case, unexpected effects may occur due to inflow of foreign materials or, compared to the case where there is no inflow of foreign materials, the particles may relatively less inflow. Therefore, it may be difficult to generate drug effects by sufficient delivery of the particles. However, the present invention may prevent the problem described above by optimizing the charge of CpG ODN-RNA composite-carrying particles.

When the positive charge of the particles is low, the loading efficiency may be deteriorated. Therefore, the present invention may optimize the charge of the particles carrying CpG-ODN-RNA composite, thereby preventing the above problem.

If the conjugate has a coupling functional group on either or both ends of CaG ODN or RNA, the porous silica particles may be surface-modified to have a functional group inside the pore, which can be coupled with the same.

A loading rate of nucleic acid molecules (conjugate) to particles, for example, a weight ratio of nucleic acid molecules and the porous silica particles may range from 1:1 to 20. When a content ratio is within the above range, the nucleic acid molecules may be sufficiently loaded while preventing generation of empty porous silica particles without carrying the nucleic acid molecules. As a result, it is possible to prevent strongly positive-charged particles from being delivered into cells. Within the above range, for example, the above ratio may be in a range of 1:1 to 20, 1:3 to 20, 1:3 to 15, 1:3 to 12, 1:3 to 10, 1:5 to 20, 1:5 to 15, 1:5 to 10, etc., but it is not limited thereto.

Specifically, in order to administer the composition of the present invention to a subject, the porous silica particles carrying nucleic acid molecule may be dispersed in a dispersion medium, which may be obtained by adding and stirring the porous silica particles and nucleic acid molecule in a dispersion medium. In this regard, if an amount of particles relative to nucleic acid molecule is too large, empty particles not sufficiently carrying nucleic acid molecule may occur, and if the amount of particles relative to nucleic acid molecule is too small, residual nucleic acid molecule not supported by the particles may be generated.

According to an embodiment of the present invention, the porous silica particles may have the following specifications. For example, the pore size may range from 7 to 30 nm, specifically, 12 to 18 nm, and more specifically 14 to 16 nm. The particle diameter may range from 50 to 1000 nm, specifically 200 to 500 nm, and more specifically 250 to 350 nm. The surface area may range from 200 to 700 $m^2/g$, and specifically, 360 to 480 $m^2/g$. The zeta potential may be 5 mV or more, specifically 20 to 70 mV, and more specifically 40 to 60 mV before loading of nucleic acid molecules. The particles may carry the nucleic acid molecules to reach a weight ratio of 1:1 to 20, and specifically 1:5 to 10.

Figure 23:
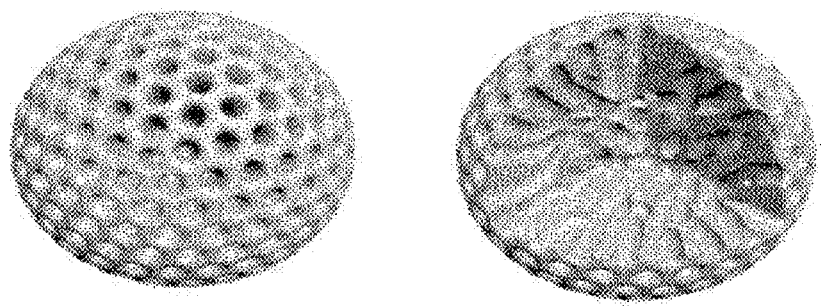
FIG. 23 is a schematic view illustrating the porous silica particles according to an embodiment of the present invention.
Figure 24:
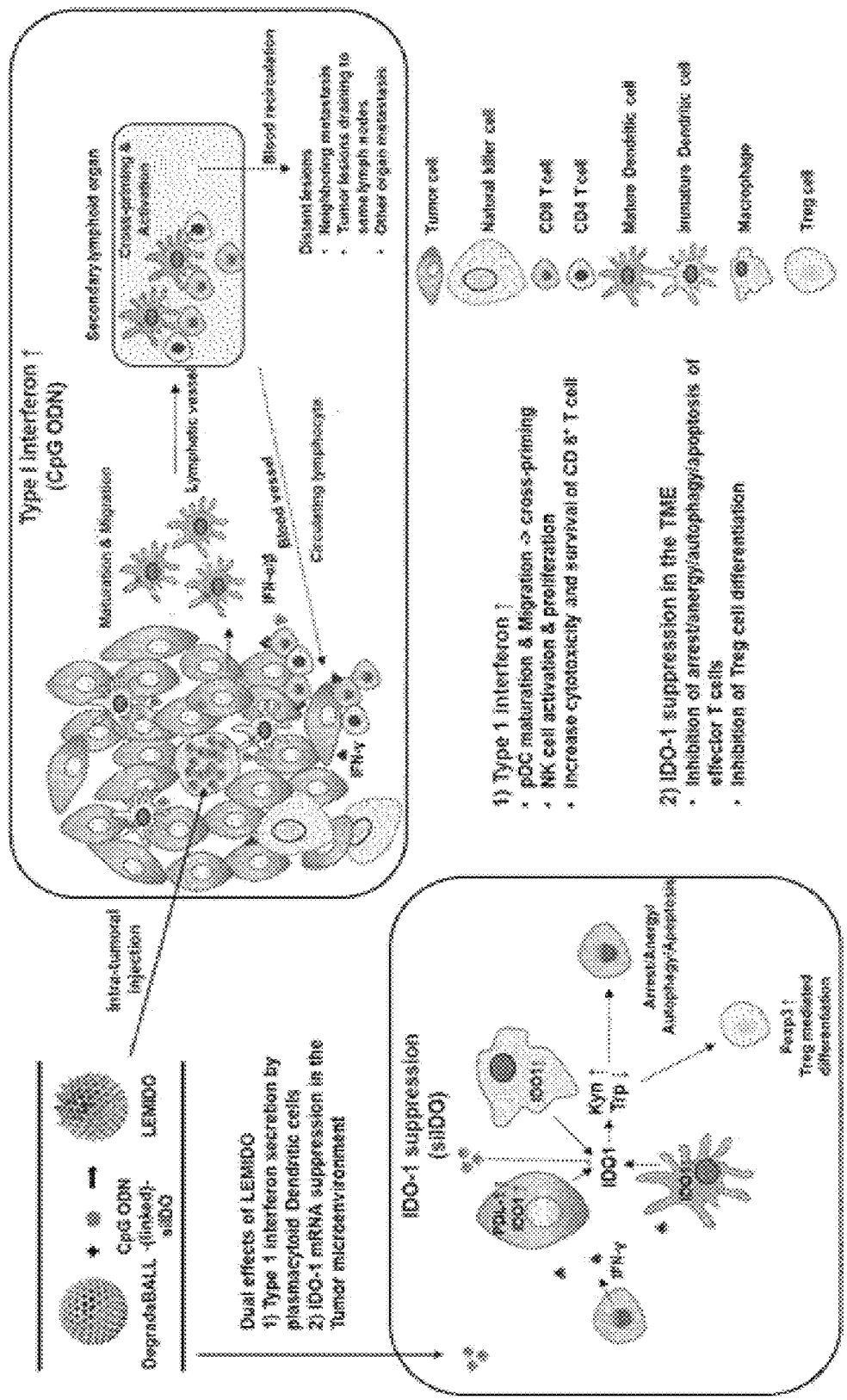
FIG. 24 is a schematic view illustrating function of the nucleic acid carrier loaded with CpG-ODN-siIDO according to an embodiment of the present invention.

As illustrated in FIG. 23, the porous silica particle may have a plurality of pores, and the pores may extend from the surface to the inside of the particle. Thus, nucleic acid molecule can be sufficiently supported inside the pores. The pores may be interconnected.

The porous silica particles of the present invention are biodegradable particles that support nucleic acid molecule and are biodegradable in the body to release nucleic acid molecule when administered into the body. The porous silica particles of the present invention may be slowly decomposed in the body so that the supported nucleic acid molecule can be released in a sustained manner. For example, t at which an absorbance ratio in Equation 1 below is 1/2 may be 24 or more:

$$A_t/A_0 \qquad \text{[Equation 1]}$$

(wherein $A_0$ is absorbance of the porous silica particles measured by putting 5 ml of suspension containing 1 mg/ml of porous silica particles into a cylindrical permeable membrane having pores with a pore diameter of 50 kDa, 15 ml of the same solvent as the suspension comes into contact with an outside of the permeable membrane, and the inside/outside of the permeable membrane are horizontally stirred at 60 rpm and at 37° C., pH of the suspension is 7.4, and $A_t$ indicates absorbance of the porous silica particle measured after lapse of "t" hours since $A_o$ was measured).

The above Equation 1 means what a rate the porous silica particles are degraded in an environment similar to the body.

For example, absorbance $A_0$ and $A_t$ in the above Equation 1 may be measured after placing porous silica particles and a suspension in a cylindrical permeable membrane and also placing the same suspension outside the permeable membrane.

The porous silica particles of the present invention are biodegradable, and may be slowly degraded in the suspension. The diameter of 50 kDa corresponds to about 5 nm, which allows biodegradable porous silica particles to pass through a permeable membrane having a diameter of 50 kDa, and a cylindrical permeable membrane is under horizontal agitation at 60 rpm to evenly blend the suspension, such that the degraded porous silica particles can come out of the permeable membrane.

The absorbance in the above Equation 1 may be measured, for example, under an environment in which the suspension outside the permeable membrane is replaced with a new suspension. The suspension may be continuously replaced, or replaced every period wherein the period is periodic or irregular. For example, the suspension may be replaced at 1 hour interval, 2 hours interval, 3 hours interval, 6 hours interval, 12 hours interval, 24 hours interval, 2 days interval, 3 days interval, 4 days interval, 7 days interval, etc., within a range of 1 hour to 1 week, but it is not limited thereto.

The absorbance ratio of 1/2 means that the absorbance is half of the initial absorbance after t hours, briefly, that approximately half of the porous silica particles are degraded.

The suspension may be a buffer solution, for example, at least one selected from the group consisting of phosphate buffered saline (PBS) and simulated body fluid (SBF), and more specifically, PBS.

"t" in the above Equation 1 of the present invention, at which the absorbance ratio becomes 1/2, may be 20 or more, for example, t may range from 24 to 120. That is, within the above range, t may range from 20 to 96, 24 to 96, 24 to 72, 30 to 70, 40 to 70, 50 to 65, etc., but it is not limited thereto.

With regard to the porous silica particles of the present invention, t at which the absorbance ratio in the above Equation 1 becomes 1/5 may range from 70 to 140. For example, t may range from 80 to 140, 80 to 120, 80 to 110, 70 to 140, 70 to 120, 70 to 110, etc. within the above range, but it is not limited thereto.

With regard to the porous silica particles of the present invention, t at which the absorbance ratio in the above Equation 1 becomes 1/20 may range from 130 to 220. For example, t may range from 130 to 200, 140 to 200, 140 to 180, 150 to 180, etc. within the above range, but it is not limited thereto.

With regard to the porous silica particles of the present invention, t at which the absorbance ratio in the above Equation 1 becomes 0.01 or less may be 250 or more. For example, t may be 300 or more, 350 or more, 400 or more, 500 or more, 1000 or more, etc. and the upper limit may be 2000, but it is not limited thereto.

With regard to the porous silica particles of the present invention, the absorbance ratio and t in the above Equation 1 have high positive correlation. For example, Pearson correlation coefficient may be 0.8 or more, and for example, 0.9 or more and 0.95 or more.

"t" in the above Equation 1 means how fast the porous silica particles are degraded under the environment similar to the body. That is, t may be regulated by adjusting, for example, a surface area, a particle size, a pore diameter, substituents on the surface of the porous silica particles and/or the inside of the pores, compactness of the surface and the like.

For example, the surface area of the particle may be increased to reduce t, or the surface area may be decreased to increase t. The surface area may be regulated by adjusting the particle size and the pore diameter of the particles. Further, if direct exposure of the porous silica particles to the environment (such as solvents) is reduced by placing substituents on the surface of the particles and/or the inside of the pores, t may be increased. Further, when the porous silica particles support or carry nucleic acid molecules, and when increasing affinity between the nucleic acid molecules and the porous silica particles, direct exposure of the porous silica particles to the environment may be reduced, thereby increasing t. In addition, t may be increased by preparing the particles with more compact surface. As described above, various examples of adjusting t in the above Equation 1 have been described, but it is not limited thereto.

The porous silica particles of the present invention may have a spherical shape, but it is not limited thereto.

The porous silica particles of the present invention may have an average diameter of, for example, 50 to 1000 nm. For example, the average diameter may range from 50 to 1000 nm, 50 to 500 nm, 50 to 400 nm, 50 to 350 nm, 100 to 1000 nm, 100 to 500 nm, 100 to 450 nm, 100 to 400 nm, 100 to 350 nm, 150 to 400 nm. 150 to 350 nm, 200 to 400 nm, 200 to 350 nm, 250 to 400 nm, 250 to 350 nm, 280 to 350 nm, etc. within the above range, but it is not limited thereto.

The porous silica particles of the present invention may have a BET surface area of, for example, 200 to 700 m$^2$/g. For example, the BET surface area may range from 200 m$^2$/g to 700 m$^2$/g, 220 m$^2$/g to 680 m$^2$/g, 220 m$^2$/g to 620 m$^2$/g, 280 m$^2$/g to 680 m$^2$/g, 280 m$^2$/g to 580 m$^2$/g, 280 m$^2$/g to 520 m$^2$/g, 280 m$^2$/g to 480 m$^2$/g, 320 m$^2$/g to 620 m$^2$/g, 320 m$^2$/g to 580 m$^2$/g, 320 m$^2$/g to 520 m$^2$/g, 320 m$^2$/g to 480 m$^2$/g, 320 m$^2$/g to 450 m$^2$/g, 320 m$^2$/g to 420 m$^2$/g, 360 m$^2$/g to 480 m$^2$/g, 360 m$^2$/g to 420 m$^2$/g, etc. within the above range, but it is not limited thereto.

Porous silica nanoparticles of the present invention may have a volume per gram, for example, 0.7 to 2.2 ml. For example, the volume may range from 0.7 to 2.0 ml, 0.8 to 2.2 ml, 0.8 to 2.0 ml, 0.9 to 2.0 ml, 1.0 to 2.0 ml, etc. within the above range, but it is not limited thereto.

The porous silica particles may include pores of small pore particles having an average pore diameter of less than 5 nm expanded to an average diameter of 7 to 30 nm. As a result, the pore diameter is large so that large nucleic acid molecules can be carried inside the pore, and the particle diameter itself is not large compared to the pore diameter, so that it is easy to deliver and absorb into the cells.

The porous silica particles of the present invention may be positively charged at an outer surface thereof and/or an inside of the pores. For example, both the surface of the particle and the inside of the pores may be positively charged, or only the surface of the particles or the inside of the pores may be positively charged. The charging may be performed, for example, by the presence of a cationic substituent.

The cationic substance may include, for example, an amino group or any other nitrogen-containing group. Further, the anionic substituent may include, for example, carboxy group (—COOH), sulfonic acid group (—$SO_3H$), thiol group (—SH), etc. as an acidic group, but it is not limited thereto.

Interaction of the porous silica particles with the release environment of the nucleic acid molecule is adjusted to regulate a degradation rate of the nanoparticles, whereby a release rate of the nucleic acid molecule may be regulated. Further, the nucleic acid molecule may be diffused and released from the nanoparticles, wherein adjusting substituents may regulate a binding force of the nucleic acid molecule to the nanoparticles, thereby controlling release of the nucleic acid molecule.

Further, the porous silica particles of the present invention may include substituents for the purposes of: supporting the nucleic acid molecule on the surface of the particles and/or the inside of the pores; delivery of the nucleic acid molecule into a target cell; supporting other substances for other purposes; or binding of additional substituents. Further, the porous silica particles may also include antibodies, ligands, cell permeable peptides, or aptamers bound thereto.

The substituents on the surface of the particles and/or the inside of the pores, charge, binders, etc. described above may be added by, for example, surface modification.

Surface modification may be performed, for example, by reacting a compound having a substituent to be introduced with the particles, wherein the compound may be, for example, alkoxysilane having C1 to C10 alkoxy group, but it is not limited thereto. The alkoxysilane has one or more alkoxy groups, for example, 1 to 3 alkoxy groups. Further, there may be a substituent to be introduced into a site where the alkoxy group is not bound, or a substituent substituted with the same.

The porous silica particles of the present invention may be manufactured, for example, through small pore particle preparation and pore expansion processes and, if necessary, may be manufactured further through calcination, or surface modification process and the like. If both the calcination and the surface modification processes have been implemented, the particles may be surface-modified after calcination.

The small pore particles may be, for example, particles having an average pore diameter of 1 to 5 nm.

The small pore particles may be harvested by adding a surfactant and a silica precursor in a solvent, followed by agitation and homogenization.

The solvent may be water and/or an organic solvent, and the organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, γ-butyrolactone, 1,3-dimethyl-imidazolidinone, methylethylketone, cyclohexanone, cyclopentanone, 4-hydroxy-4-methyl-2-pentanone, etc.; aromatic carbon-based materials such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (cellosolve) such as ethyleneglycol monoethyl ether, ethyleneglycol monomethyl ether, ethyleneglycol monobutyl ether, diethyleneglycol monoethyl ether, diethyleneglycol monomethyl ether, diethyleneglycol monobutyl ether, propyleneglycol monomethyl ether, propyleneglycol monoethyl ether, dipropyleneglycol diethyl ether, triethyleneglycol monoethyl ether, etc.; others such as dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethylphosphoamide, tetramethylurea, N-methylcarrolactam, tetrahydrofuran, m-dioxane, P-dioxane, 1,2-dimethoxyethane and the like. Specifically, alcohol, more specifically methanol may be used, but it is not limited thereto.

When using a mixed solvent of water and the organic solvent, a relative ratio of water and organic solvent may be, for example, in a volume ratio of 1:0.7 to 1.5, for example, 1:0.8 to 1.3, but it is not limited thereto.

The surfactant may include, for example, cetyltrimethylammonium bromide (CTAB), hexadecyltrimethylammonium bromide (TMABr), hexadecyltrimethylpyridinium chloride (TMPrCl), tetramethylammonium chloride (TMACl), etc., and specifically, CTAB may be used.

The surfactant may be added, for example, in an amount of 1 to 10 g, for example, 1 to 8 g, 2 to 8 g or 3 to 8 g per liter of solvent within the above range, but it is not limited thereto.

The silica precursor may be added after stirring with addition of a surfactant to the solvent. The silica precursor may be, for example, tetramethyl orthosilicate (TMOS), but it is not limited thereto.

The stirring may be conducted, for example, for 10 to 30 minutes, but it is not limited thereto.

The silica precursor may be added in an amount of 0.5 to 5 ml per liter of solvent, for example, 0.5 ml to 4 ml, 0.5 to 3 ml, 0.5 to 2 ml, 1 to 2 ml, etc. within the above range, but it is not limited thereto.

If necessary, sodium hydroxide may further be used as a catalyst, and specifically, may be added under stirring after addition of the surfactant and before addition of the silica precursor to the solvent.

The sodium hydroxide may be added in an amount of 0.5 to 8 ml per liter of solvent, for example, 0.5 to 5 ml, 0.5 to 4 ml, 1 to 4 ml, 1 to 3 ml, 2 to 3 ml, etc. within the above range based on 1 M aqueous sodium hydroxide solution, but it is not limited thereto.

After addition of the silica precursor, the solution may be reacted with stirring. The stirring may be conducted for 2 to 15 hours, for example, 3 to 15 hours, 4 to 15 hours, 4 to 13 hours, 5 to 12 hours, 6 to 12 hours, 6 to 10 hours, etc. within the above range, but it is not limited thereto. If the stirring time (reaction time) is too short, nucleation may be insufficient.

After agitation, the solution may be aged. Aging may be performed for 8 to 24 hours, for example, for 8 to 20 hours, 8 to 18 hours, 8 to 16 hours, 8 to 14 hours, 10 to 16 hours, 10 to 14 hours, etc. within the above range, but it is not limited thereto.

Thereafter, the reaction product may be washed and dried to harvest porous silica particles and, if necessary, separation of unreacted material may proceed before washing.

Separation of the unreacted material may be implemented by separating the supernatant, for example, through centrifugation. For example, centrifugation may be conducted at 6,000 to 10,000 rpm, and the centrifugation time may range from 3 to 60 minutes, for example, 3 to 30 minutes, 5 to 30 minutes, etc. within the above range, but it is not limited thereto.

The washing may be conducted with water and/or an organic solvent. Specifically, since different substances are dissolved in different solvents, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, γ-butyrolactone, 1,3-dimethyl-imidazolidinone, methylethylketone, cyclohexanone, cyclopentanone, 4-hydroxy-4-methyl-2-pentanone, etc.; aromatic carbon-based materials such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (cellosolve) such as ethyleneglycol monoethyl ether, ethyleneglycol monomethyl ether, ethyleneglycol monobutyl ether, diethyleneglycol monoethyl ether, diethyleneglycol monomethyl ether, diethyleneglycol monobutyl ether, propyleneglycol monomethyl ether, propyleneglycol monoethyl ether, dipropyleneglycol diethyl ether, triethyleneglycol monoethyl ether, etc.; others such as dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethylphosphoamide, tetramethylurea, N-methylcarrolactam, tetrahydrofuran, m-dioxane, P-dioxane, 1,2-dimethoxyethane and the like. Specifically, alcohol, more specifically methanol may be used, but it is not limited thereto.

The washing may be conducted under centrifugation, for example, at 6,000 to 10,000 rpm, and the centrifugation time may range from 3 to 60 minutes, for example, 3 to 30 minutes, 3 to 30 minutes, 5 to 30 minutes, etc. within the above range, but it is not limited thereto.

Alternatively, the washing may be conducted by filtering out particles through a filter without centrifugation. The filter may have pores in a size of less than or equal to the diameter of the porous silica particles. When filtering the reaction solution with such a filter as described above, only particles remain on the filter, which may be washed by pouring water and/or an organic solvent on the filter.

In the washing, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

In the particles produced by the above-described method, residual organic substances (surfactants, etc.) used for the reaction may remain on the surface and inside the pores, and washing may be performed to remove the same. Usually, acid treatment (or acidic organic solvent treatment) may be performed to remove such organic substances, but in the present invention, since such acid treatment is not performed, residual organic substances may remain in the pores even after washing.

The drying may be conducted, for example, at 20 to 100° C., but it is not limited thereto, and may also be conducted in a vacuum state.

Thereafter, the pore of the harvested porous silica particles may be expanded, and such pore expansion may be conducted using a pore swelling agent.

The pore swelling agent may include, for example, trimethylbenzene, triethylbenzene, tripropylbenzene, tributylbenzene, tripentylbenzene, trihexylbenzene, toluene, benzene, etc., and specifically, trimethylbenzene may be used, but it is not limited thereto.

Further, the pore swelling agent used herein may be, for example, N, N-dimethylhexadecylamine (DMHA), but it is not limited thereto.

The pore expansion may be performed, for example, by mixing the porous silica particles in the solvent with a pore swelling agent and heating the mixture to induce reaction.

The solvent may be water and/or an organic solvent, and the organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; aromatic carbon-based materials such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol and the like. Specifically, alcohol, more specifically methanol may be used, but it is not limited thereto.

The porous silica particles may be added in a ratio of 10 to 200 g per liter of solvent, for example, 10 to 150 g, 10 to 100 g, 30 to 100 g, 40 to 100 g, 50 to 100 g, 50 to 80 g, 60 to 80 g, etc., within the above range, but it is not limited thereto.

The porous silica particles may be evenly dispersed in a solvent. For example, the porous silica particles may be added to the solvent and ultrasonically dispersed. In the case of using a mixed solvent, the porous silica particles may be dispersed in a first solvent, followed by adding a second solvent thereto.

The pore swelling agent may be added in a ratio of 10 to 200 parts by volume ("vol. parts") based on 100 vol. parts of solvent, for example, 10 to 150 vol. parts, 10 to 100 vol.

parts, 10 to 80 vol. parts, 30 to 80 vol. parts, 30 to 70 vol. parts, etc. within the above range, but it is not limited thereto.

The reaction may be carried out at 120 to 190° C., for example, 120 to 190° C., 120 to 180° C., 120 to 170° C., 130 to 170° C., 130 to 160° C., 130 to 150° C., 130 to 140° C., etc. within the above range, but it is not limited thereto.

The reaction may be carried out for 6 to 96 hours, for example, 30 to 96 hours, 30 to 80 hours, 30 to 72 hours, 24 to 80 hours, 24 to 72 hours, 36 to 96 hours, 36 to 80 hours, 36 to 72 hours, 36 to 66 hours, 36 to 60 hours, 48 to 96 hours, 48 to 88 hours, 48 to 80 hours, 48 to 72 hours, 6 to 96 hours, 7 to 96 hours, 8 to 80 hours, 9 to 72 hours, 9 to 80 hours, 6 to 72 hours, 9 to 96 hours, 10 to 80 hours, 10 to 72 hours, 12 to 66 hours, 13 to 60 hours, 14 to 96 hours, 15 to 88 hours, 16 to 80 hours, 17 to 72 hours, etc. within the above range, but it is not limited thereto.

The time and temperature may be desirably adjusted within the ranges exemplified above so that the reaction may be carried out sufficiently but not excessively. For example, when the reaction temperature is reduced, the reaction time may be increased, and when the reaction temperature is increased, the reaction time may be shortened. If the reaction is not sufficiently performed, pore expansion may be insufficient. On the other hand, if the reaction proceeds excessively, the particles may collapse due to overexpansion of the pores.

The reaction may be carried out, for example, by gradually raising the temperature. Specifically, the reaction may be carried out by gradually raising the temperature at a rate of 0.5 to 15° C./min from the room temperature to the above-defined temperature. For example, the temperature may be raised at a rate of 1 to 15° C./min, 3 to 15° C./min, 3 to 12° C./min, 3 to 10° C./min, etc., but it is not limited thereto.

The reaction may be carried out under stirring. For example, the stirring may be implemented at a speed of 100 rpm or more, and specifically, at a speed of 100 to 1000 rpm, but it is not limited thereto.

After the reaction, the reaction solution may be cooled slowly, for example, by gradually decreasing the temperature. Specifically, the reaction may be carried out by gradually decreasing the temperature at a rate of 0.5 to 20° C./min from the above-defined temperature to room temperature. For example, the temperature may be decreased at a rate of 1 to 20° C./min, 3 to 20° C./min, 3 to 12° C./min, 3 to 10° C./min, etc. within the above range, but it is not limited thereto.

If the particles are not washed by acid treatment after the production of the particles, the residual material inside the pores may also participate in the pore expansion, so that the pores may be expanded more sufficiently evenly.

After cooling, the reaction product may be washed and dried to harvest porous silica particles having expanded pores. If necessary, unreacted material may be first separated before washing.

Separation of the unreacted material may be implemented by separating the supernatant, for example, through centrifugation. Herein, centrifugation may be conducted, for example, at 6,000 to 10,000 rpm, and the centrifugation time may range from 3 minutes to 60 minutes. For example, the centrifugation may be conducted for 3 to 30 minutes, 5 to 30 minutes, etc. within the above range, but it is not limited thereto.

The washing may be conducted with water and/or an organic solvent. Specifically, since different substances are dissolved in different solvents, water and the organic solvent may be used alternately once or several times, or the washing may be conducted with water or the organic solvent alone once or several times. The several times described above may be 2 times or more and 10 times or less, for example, 3 times, 4 times, 5 times, 6 times, 7 times, 8 times, etc.

The organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; aromatic carbon-based materials such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol and the like. Specifically, alcohol, more specifically methanol may be used, but it is not limited thereto.

The washing may be conducted under centrifugation, for example, at 6,000 to 10,000 rpm, and the centrifugation time may range from 3 to 60 minutes, for example, 3 to 30 minutes, 5 to 30 minutes, etc. within the above range, but it is not limited thereto.

Alternatively, the washing may be conducted by filtering out particles through a filter without centrifugation. The filter may have pores in a size of less than or equal to the diameter of the porous silica particles. When filtering the reaction solution with such a filter as described above, only particles remain on the filter, which may be washed by pouring water and/or an organic solvent on the filter.

In the washing, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

If the particles are not washed by acid treatment after the production of the particles, residual material inside the pores may remain even after pore expansion, such that the acid treatment may be performed even when washing after pore expansion, but the present invention does not perform acid treatment, instead, residual material can be removed by calcination to be described below.

The drying may be conducted, for example, at 20 to 100° C., but it is not limited thereto, and may also be conducted in a vacuum state.

Thereafter, the harvested particles may be subjected to calcination, which is a process of heating the particles to remove silanol groups present on the surface of the particles and inside of the pores so as to reduce reactivity of the particles, provide a more compact structure, and remove organic matter filling the pores. For example, the particles may be heated to a temperature of 400° C. or higher. The upper limit of the temperature is not particularly limited but may be 1000° C., 900° C., 800° C., 700° C., etc. The heating may be conducted, for example, for 3 hours or more, 4 hours or more, etc. The upper limit of the heating time is not particularly limited but may be 24 hours, 12 hours, 10 hours, 8 hours, 6 hours, 5 hours, etc. More particularly, the heating may be conducted at 400 to 700° C. for 3 to 8 hours or at 500 to 600° C. for 4 to 5 hours, but it is not limited thereto.

Removing the organic matter filling the pores can prevent some problems of cytotoxicity or foaming caused by the remaining organic matter.

Then, the harvested porous silica particles may be subjected to surface modification, and the surface modification may be performed on the surface of the particles and/or the inside of the pores. Both the particle surface and the inside of the pores may be surface-modified in the same manner, or may be surface-modified differently.

The particles may be charged through surface modification.

Surface modification may be performed, for example, by reacting a compound having a cationic substituent to be introduced with the particles, wherein the compound may be, for example, alkoxysilane having a C1 to C10 alkoxy group, but it is not limited thereto.

The alkoxysilane has one or more alkoxy groups, for example, 1 to 3 alkoxy groups. Further, there may be a substituent to be introduced into a site where the alkoxy group is not bound, or a substituent substituted with the same.

When alkoxysilane reacts with the porous silica particles, a covalent bond is formed between a silicon atom and an oxygen atom such that the alkoxysilane may be bound to the surface of the porous silica particles and/or the inside of the pores. Since the alkoxysilane has a substituent to be introduced, the corresponding substituent may be introduced into the surface of the porous silica particles and/or the inside of the pores.

The reaction may be implemented by reacting the porous silica particles dispersed in a solvent with alkoxysilane.

The solvent may be water and/or an organic solvent, and the organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, γ-butyrolactone, 1,3-dimethyl-imidazolidinone, methylethylketone, cyclohexanone, cyclopentanone, 4-hydroxy-4-methyl-2-pentanone, etc.; aromatic carbon-based materials such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (cellosolve) such as ethyleneglycol monoethyl ether, ethyleneglycol monomethyl ether, ethyleneglycol monobutyl ether, diethyleneglycol monoethyl ether, diethyleneglycol monomethyl ether, diethyleneglycol monobutyl ether, propyleneglycol monomethyl ether, propyleneglycol monoethyl ether, dipropyleneglycol diethyl ether, triethyleneglycol monoethyl ether, etc.; others such as dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethylphosphoamide, tetramethylurea, N-methylcarrolactam, tetrahydrofuran, m-dioxane, P-dioxane, 1,2-dimethoxyethane and the like. Specifically, alcohol, more specifically methanol may be used, but it is not limited thereto.

The positively charging may be performed by reacting the porous silica particles with alkoxysilane having a basic group such as a nitrogen-containing group, for example, an amino group or an aminoalkyl group. Specifically, N-[3-(trimethoxysilyl)propyl]ethylenediamine, N1-(3-trimethoxysilylpropyl)diethylenetriamine, (3-aminopropyl)trimethoxysilane, N-[3-(trimethoxysilyl)propyl]aniline, trimethoxy[3-(methylamino)propyl]silane, 3-(2-aminoethylamino)propyldimethoxymethylsilane, etc. may be used, but it is not limited thereto.

Further, the surface modification may be performed in combination. For example, surface modification may be performed twice or more on the outer surface of the particles or the inside of the pores. As a specific example, a compound including a carboxyl group may be bound to silica particles having amino groups introduced therein through amide bond in order to change the positively-charged particles to have different surface properties, but it is not limited thereto.

The reaction of the porous silica particles with alkoxysilane may be carried out, for example, under heating. The heating may be conducted at 80 to 180° C., for example, 80 to 160° C., 80 to 150° C., 100 to 160° C., 100 to 150° C., 110 to 150° C., etc. within the above range, but it is not limited thereto.

The reaction of the porous silica particles with alkoxysilane may be carried out for 4 to 20 hours, for example, 4 to 18 hours, 4 to 16 hours, 6 to 18 hours, 6 to 16 hours, 8 to 18 hours, 8 to 16 hours, 8 to 14 hours, 10 to 14 hours, etc. within the above range, but it is not limited thereto.

The reaction temperature, time and an amount of the compound used for surface modification may be desirably selected according to an extent of surface modification. In other words, reaction conditions will vary depending on a level of charge with regard to nucleic acid molecules. Specifically, by controlling the level of charge of the porous silica particles, a release rate of the nucleic acid molecule may be controlled. For example, if the nucleic acid molecule has a strong negative charge at neutral pH, the reaction temperature may be raised, the reaction time may be extended or the amount of the treated compound may be increased so as to make the porous silica particles to have a strong positive charge, but it is not limited thereto.

Further, the porous silica particles of the present invention may be manufactured through, for example, preparation of small pore particles, pore expansion, surface modification, and internal pore modification.

Preparation of small pore particles and pore expansion may be performed by the above-described processes and, after preparation of the small pore particles and after pore expansion, washing and drying processes may be implemented.

If necessary, unreacted materials may be separated before washing, and separation of the unreacted materials may be conducted by separating the supernatant through centrifugation.

Centrifugation may be conducted at 6,000 to 10,000 rpm, and the centrifugation time may range from 3 to 60 minutes, for example, 3 to 30 minutes, 5 to 30 minutes, etc. within the above range, but it is not limited thereto.

The washing after preparation of small pore particles may be conducted by a method/condition within the above-described range, but it is not limited thereto.

The washing after pore expansion may be conducted under more moderate conditions than the above embodiments. For example, washing may be conducted three times or less, but it is not limited thereto.

The surface modification and internal pore modification may be performed by the above-described processes, respectively. Herein, surface modification and then internal pore modification may be performed in this order, and a washing process may be further conducted between the above two processes.

When the washing is conducted in more moderated conditions after preparation of small pore particles and pore expansion, a reaction solution such as a surfactant used for particle production and pore expansion is filled in the pores so that the inside of the pores is not modified during surface modification and, instead, only the surface of the particles may be modified. Thereafter, the reaction solution inside of the pores may be washed out and removed.

Particle washing between the surface modification and the internal pore modification processes may be carried out using water and/or an organic solvent. Specifically, since different substances are dissolved in different solvents, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The washing may be carried out under centrifugation, for example at 6,000 to 10,000 rpm, and the centrifugation time may range from 3 to 60 minutes, for example, 3 to 30 minutes, 5 to 30 minutes, etc. within the above range, but it is not limited thereto.

Alternatively, the washing may be conducted by filtering out particles through a filter without centrifugation. The filter may have pores in a size of less than or equal to the diameter of the porous silica particles. When filtering the reaction solution with such a filter as described above, only particles remain on the filter, which may be washed by pouring water and/or an organic solvent on the filter.

In the washing, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The drying may be conducted, for example, at 20 to 100° C., but it is not limited thereto, and may also be conducted in a vacuum state.

The nucleic acid molecule may be supported on the surface of the porous silica particles and/or inside the pores. Herein, the supporting may be performed, for example, by mixing porous silica particles in a solvent with the nucleic acid molecule.

The solvent may be water and/or an organic solvent, and the solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; aromatic carbon-based materials such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol and the like. Specifically, alcohol, more specifically methanol may be used, but it is not limited thereto.

Further, PBS (phosphate buffered saline solution), SBF (simulated body fluid), borate-buffered saline, tris-buffered saline may be used as the solvent.

The nucleic acid molecule supported on the porous silica particles may be gradually released over an extended time. Such sustained release may be continuous or discontinuous, or linear or nonlinear. Further, the release may vary depending upon characteristics of the porous silica particles and/or interaction between the porous silica particles and the nucleic acid molecule.

The nucleic acid molecule supported on the porous silica particles are released when the porous silica particles are biodegraded. Specifically, the porous silica particles according to the present invention are slowly degraded to allow release of the nucleic acid molecule in a sustained manner. Such release may be controlled by, for example, adjusting surface area, particle size, pore diameter, substituents on the surface of the particles and/or the inside of the pores, surface compactness, etc. with regard to the porous silica particles, but it is not limited thereto.

The nucleic acid molecule supported on the porous silica particles may be released while being separated and diffused from the porous silica particles. Such release is influenced by correlations between the porous silica particles, the nucleic acid molecule and release environment of the same. Therefore, regulating the correlations may control the release of the nucleic acid molecule. For example, by enhancing or weakening a binding force of the porous silica particles to the nucleic acid molecule through surface modification, the release of the nucleic acid molecule may be controlled.

The nucleic acid molecule may be released for a period of, for example, 7 days to 1 year or more, depending on types of treatment to be required, release environments and types of porous silica particles to be used.

Further, if the porous silica particles of the present invention are biodegradable, these can be 100% degraded. Therefore, the nucleic acid molecule supported thereon may be 100% released.

Further, the present invention relates to a pharmaceutical composition for prevention or treatment of cancer.

The pharmaceutical composition of the present invention may include the nucleic acid carrier.

The nucleic acid molecule and porous silica particles may be within the ranges described above.

The composition of the present invention may have anticancer efficacy, wherein nucleic acid molecules loaded therein can be stably delivered to the body, released to a target, thereby inhibiting expression of indoleamine 2,3-dioxygenase (IDO-1).

Due to inhibition of IDO1 expression, generation of kynurenine (KYN) by IDO1 may be prevented, while suppressing differentiation of Treg cells.

Cancer as a target to be prevented or treated using the composition of the present invention may be any cancer that can be prevented or treated through the above pathways, and may include, for example, ovarian cancer, cervical cancer, follicle cysts, gynecologic cancer, urologic cancer, renal cancer, testicular cancer, penile cancer, genitourinary tract cancer, testicular tumor, bladder cancer, skin cancer, sarcoma, osteosarcoma, malignant bone tumor, soft tissue sarcoma, keratoacanthoma, melanoma, lung cancer, small cell lung carcinoma, non-small cell lung carcinoma (NSCLC), lung adenocarcinoma, squamous cell carcinoma of the lung, papillary cancer, breast cancer, triple negative breast cancer (TNBC), breast endocrine cancer, hepatobiliary and pancreatic cancer, liver cancer, cholangiocarcinoma, gallbladder cancer, bile duct cancer, pancreatic cancer, bone cancer, bone marrow disorder, lymphatic disorder, hair cell cancer, oral and pharyngeal (oral) cancer, lip cancer, tongue cancer, oral cancer, salivary gland cancer, pharyngeal cancer, laryngeal cancer, esophageal cancer, gastric cancer, gastrointestinal cancer, small intestine cancer, colon cancer, rectal cancer, prostate cancer, vulvar cancer, thyroid cancer, large intestine cancer, endometrial cancer, uterine cancer, brain cancer, glioma, non-glioma tumor, malignant glioma, metastatic brain cancer, brain parenchyma, vestibular schwannoma, pituitary tumor, head and neck cancer, central nervous system cancer, peritoneal cancer, hepatocellular carcinoma, head cancer, neck cancer, primary tumor, metastatic tumor, lymphoma, squamous cell carcinoma, hematologic malignancy, endocrine cancer, Hodgkin disease or leukemia, etc., but it is not limited thereto.

The pharmaceutical composition of the present invention may further include a pharmaceutically acceptable carrier, and may be formulated along with such a carrier. As used herein, the term "pharmaceutically acceptable carrier" refers to a carrier or diluent that does not stimulate the organism and does not inhibit biological activities and properties of the administered compound. Pharmaceutical carriers acceptable in the composition formulated as a liquid solution are sterile and biocompatible, and may include saline, sterile water, Ringer's solution, buffered saline, albumin injectable solutions, dextrose solution, maltodextrin solution, glycerol, ethanol, and a mixture of one or more of these components. Further, if necessary, other typical additives such as antioxidants, buffers and bacteriostatic agents may be added. Diluents, dispersants, surfactants, binders and lubricants may also be added to formulate the pharmaceutical composition into injectable formulations, pills, capsules, granules or tablets such as aqueous solutions, suspensions, emulsions and the like.

The pharmaceutical composition of the present invention is applicable in a form of any formulation containing the nucleic acid molecule of the present invention as an active ingredient, and may be prepared in oral or parenteral formulations. The pharmaceutical formulations of the present invention may include forms suitable for oral, rectal, nasal, topical (including the cheek and sublingual), subcutaneous, vaginal or parenteral (intramuscular, subcutaneous) administration. Alternatively, forms suitable for administration by inhalation or insufflations may also be included.

The pharmaceutical composition of the present invention is administered in a pharmaceutically effective amount. Effective dose levels may be determined depending on types of disease of the patient, severity, activity of drug, sensitivity to drug, administration time, administration route and rate of release, duration of treatment, factors including concurrent medications, and other factors well known in the medical field. The pharmaceutical composition of the present invention may be administered as an individual therapeutic agent or in combination with other therapeutic agents, may be administered sequentially or simultaneously with conventional therapeutic agents, and may be administered in single or multiple doses. Taking all of the above factors into consideration, it is important to administer the pharmaceutical composition in an amount that can achieve maximum effects with a minimum amount without side effects, which may be easily determined by those skilled in the art.

The dosage of the pharmaceutical composition according to the present invention may vary widely depending on the weight, age, sex, health conditions or diet of a patient, administration time, administration method, excretion rate and severity of the disease, and the appropriate dosage depends on, for example, an amount of drug accumulated in the patient's body and/or specific efficacy of the carrier of the present invention used. For example, the amount may be from 0.01 µg to 1 g per kg of body weight. Further, the pharmaceutical composition of the present invention may be administered once or several times per unit time during unit periods of time such as daily, weekly, monthly or yearly, or may be continuously administered using an infusion pump for a long time. The number of repeated administration doses is determined in consideration of a residential time of drug in the body, a drug concentration in the body, etc. Even after treatment according to the course of disease treatment, the composition may be further administered for preventing recurrence, i.e., relapse of the disease.

The composition of the present invention may be administered intratumorally.

The pharmaceutical composition of the present invention may further include a compound to maintain/increase one or more of active ingredients exhibiting the same or similar functions in relation to treatment of wounds or the solubility and/or absorption of at least one active ingredient.

Further, the pharmaceutical composition of the present invention may be formulated using any method known in the art to allow rapid, sustained or delayed release of the active ingredient after administration to a mammal. The formulation may be produced in a form of powders, granules, tablets, emulsions, syrups, aerosols, soft or hard gelatin capsules, sterile injectable solutions, sterile powders.

Further, the present invention relates to RNA.

The RNA of the present invention may consist of sequences below.

(1) siRNA of SEQ ID NOs: 1 and 2
(2) siRNA of SEQ ID NOs: 3 and 4
(3) siRNA of SEQ ID NOs: 5 and 6
(4) siRNA of SEQ ID NOs: 7 and 8, or
(5) siRNA of SEQ ID NOs: 9 and 10.

siRNA of the present invention may be siRNA targeting IDO mRNA.

The siRNA of the present invention may further include a base having a length of 1 to 10 nt, which is coupled to a N-terminal or C-terminal thereof. Length extension as described above may be performed to improve stability. The added base may be any base without limitation as long as it does not prevent expression inhibitory efficiency to mRNA in the siRNA. For example, the base may be a complementary base to the target. The base may have a length of 1 to 10 nt, 1 to 8 nt, 1 to 6 nt, etc. For example, siRNA of SEQ ID NOs: 11 and 12 may be used.

IDO siRNA may have a length of, for example, 10 to 50 nt, 10 to 30 nt, 10 to 25 nt, 15 to 25 nt, 17 to 23 nt, 17 to 25 nt, etc., but it is not limited thereto.

RNA of the present invention may further include CpG oligodeoxynucleotide (CpG-ODN). For example, RNA of the present invention may be CpG-ODN-IDO siRNA conjugate.

CpG-ODN is not particularly limited in terms of class and, for example, may include class A, B or C, and specifically class A (CpG-A ODN). Class A is preferably used in an aspect of Type 1 IFN induction.

With regard to CpG-ODN, sequences known in the art may be used without limitation thereof. For example, sequences of SEQ ID NOs: 13 to 15 may be used, specifically, the sequence of SEQ ID NO: 13 may be used.

CpG-ODN may have a length of, for example, 10 to 100 nt, 10 to 80 nt, 10 to 50 nt, 15 to 80 nt, 15 to 50 nt, 10 to 40 nt, 10 to 30 nt, 15 to 40 nt, 15 to 30 nt, 10 to 25 nt, 15 to 25 nt or 20 to 25 nt, but it is not limited thereto.

CpG-ODN may be coupled through a linker of the siRNA. The linker used herein may be any one known in the art without limitation thereof. For example, saturated alkyl chains (C3 to C18), triazole linker, 4-methyl-6,7,8,9,10,10a-hexahydro-5H-3λ2-cycloocta[d]pyridazine linker, etc. may be used. In aspects of in vivo additional reaction and minimum side effects, saturated alkyl chains are preferably used. The saturated alkyl chains used herein may include C3 to C18, C3 to C15, C3 to C12, C3 to C10, C4 to C15, C4 to C12, C4 to C10, C4 to C8, C5 to C15, C5 to C12, C5 to C10, C3 to C8, C3 to C6, or C4 to C6 chains.

For loading RNA in the particles, RNA may further have a functional group on either or both ends of CpG ODN or IDO siRNA, wherein the functional group can be coupled to the porous silica particles. Further, in biological and chemical fields, functional groups possibly coupled to each other or a compound having the same may be employed without limitation thereof. Such functional groups for coupling may be used inside pores of the particles and the conjugate, therefore, the conjugate may be loaded in the porous silica particles due to coupling between the functional groups Hereinafter, the present invention will be described in detail with reference to the following examples.

EXAMPLE

Example 1. Porous Silica Particles (DDV or DegradaBALL)

1. Preparation of Porous Silica Particles
(1) Preparation of Porous Silica Particles
1) Preparation of Small Pore Particles 960 mL of distilled water (DW) and 810 mL of MeOH were put into a 2 L round bottom flask. 7.88 g of CTAB was added to the flask, followed by rapid addition of 4.52 mL of 1M NaOH under stirring. After adding a homogeneous mixture while stirring for 10 minutes, 2.6 mL of TMOS was further added. After stirring for 6 hours to mix uniformly, the reaction solution was aged for 24 hours.

Then, the reaction solution was centrifuged at 8000 rpm and 25° C. for 10 minutes to remove the supernatant, centrifuged at 8000 rpm and 25° C. for 10 minutes, and washed five times with ethanol and distilled water alternately.

Thereafter, the resultant product was dried in an oven at 70° C. to harvest 1.5 g of powdery microporous silica particles (pore average diameter of 2 nm and particle size of 200 nm).

2) Pore Expansion 1.5 g of microporous silica particle powder was added to 10 ml of ethanol and subjected to ultrasonic dispersion, and 10 ml of water and 10 ml of TMB (trimethyl benzene) were further added, followed by ultrasonic dispersion.

Thereafter, the dispersion was placed in an autoclave and reacted at 160° C. for 48 hours.

The reaction was initiated at 25° C. and performed while raising the temperature at a rate of 10° C./min, then slowly cooled in an autoclave at a rate of 1 to 10° C./min.

The cooled reaction solution was centrifuged at 8000 rpm for 10 minutes at 25° C. to remove the supernatant, and centrifuged at 8000 rpm for 10 minutes at 25° C. and washed five times with ethanol and distilled water alternately.

Then, the product was dried in an oven at 70° C. to harvest powdery porous silica particles (pore diameter of 10 to 15 nm, and particle size of 200 nm).

3) Calcination

The porous silica particles prepared in 2) were put in a glass vial, heated at 550° C. for 5 hours, and cooled slowly to room temperature after completing the reaction to prepare particles.

(2) Preparation of Porous Silica Particles

Porous silica particles were prepared by the same method as Example 1-1-(1), except that the reaction conditions at the time of pore expansion were changed to 140° C. and 72 hours.

(3) Preparation of Porous Silica Particles (10 L Scale)

Porous silica particles were prepared by the same method as Example 1-1-(1), except that a 5 times larger container was used and each material was used in a 5 times capacity.

(4) Preparation of Porous Silica Particles (Particle Size of 300 nm)

Porous silica particles were prepared by the same method as Example 1-1-(1), except that 920 ml of distilled water and 850 ml of methanol were used to prepare the small pore particles.

(5) Preparation of Porous Silica Particles (Particle Size of 500 nm)

Porous silica particles were prepared by the same method as Example 1-1-(1), except that 800 ml of distilled water, 1010 ml of methanol, and 10.6 g of CTAB were used to prepare the small pore particles.

(6) Preparation of Porous Silica Particles (Particle Size of 1000 nm)

Porous silica particles were prepared by the same method as Example 1-1-(1), except that 620 ml of distilled water, 1380 ml of methanol, and 7.88 g of CTAB were used to prepare the small pore particles.

(7) Preparation of Porous Silica Particles (Pore Diameter of 4 nm)

Porous silica particles were prepared by the same method as Example 1-1-(1), except that 2.5 mL of TMB was used for pore expansion.

(8) Preparation of Porous Silica Particles (Pore Diameter of 7 nm)

Porous silica particles were prepared by the same method as Example 1-1-(1), except that 4.5 mL of TMB was used for pore expansion.

(9) Preparation of Porous Silica Particles (Pore Diameter of 17 nm)

Porous silica particles were prepared by the same method as Example 1-1-(1), except that 11 mL of TMB was used for pore expansion.

(10) Preparation of Porous Silica Particles (Pore Diameter of 23 nm)

Porous silica particles were prepared by the same method as Example 1-1-(1), except that 12.5 mL of TMB was used for pore expansion.

(11) Preparation of Porous Silica Particles

Porous silica particles were prepared by the same method as Example 1-1-(1), except that 900 ml of distilled water, 850 mL of methanol and 8 g of CTAB were used in preparation of small pore particles.

2. Surface Modification of Porous Silica Particles (1) The porous silica particles of Example 1-1-(1) were reacted with (3-aminopropyl)triethoxysilane (APTES) to be positively charged.

Specifically, 100 mg of porous silica particles were dispersed in a 10 mL toluene in a 100 mL round bottom flask with a bath sonicator. Then, 1 mL of APTES was added and stirred at 400 rpm and 130° C. for 12 hours.

After the reaction, the product was slowly cooled to room temperature and centrifuged at 8000 rpm for 10 minutes to remove the supernatant, further centrifuged at 8000 rpm and 25° C. for 10 minutes, and then washed five times with ethanol and distilled water alternately.

Thereafter, the product was dried in an oven at 70° C. to harvest powdery porous silica particles having an amino group on the surface thereof and inside of the pores.

(2) The product of Example 1-1-(11) was subjected to surface modification by the same method described above except of using 1.8 mL of APTES, thereby obtaining powdery porous silica particles having amino groups on surface of the particle and inside the pore.

3. Identification of Particle Formation and Pore Expansion

Small pore particles and porous silica particles prepared in Experimental Examples 1-1-(1) to (3) were observed under a microscope to determine whether the small pore particles were uniformly formed or the pores were sufficiently expanded to uniformly form the porous silica particles (FIGS. 1 to 4).

Figure 2:
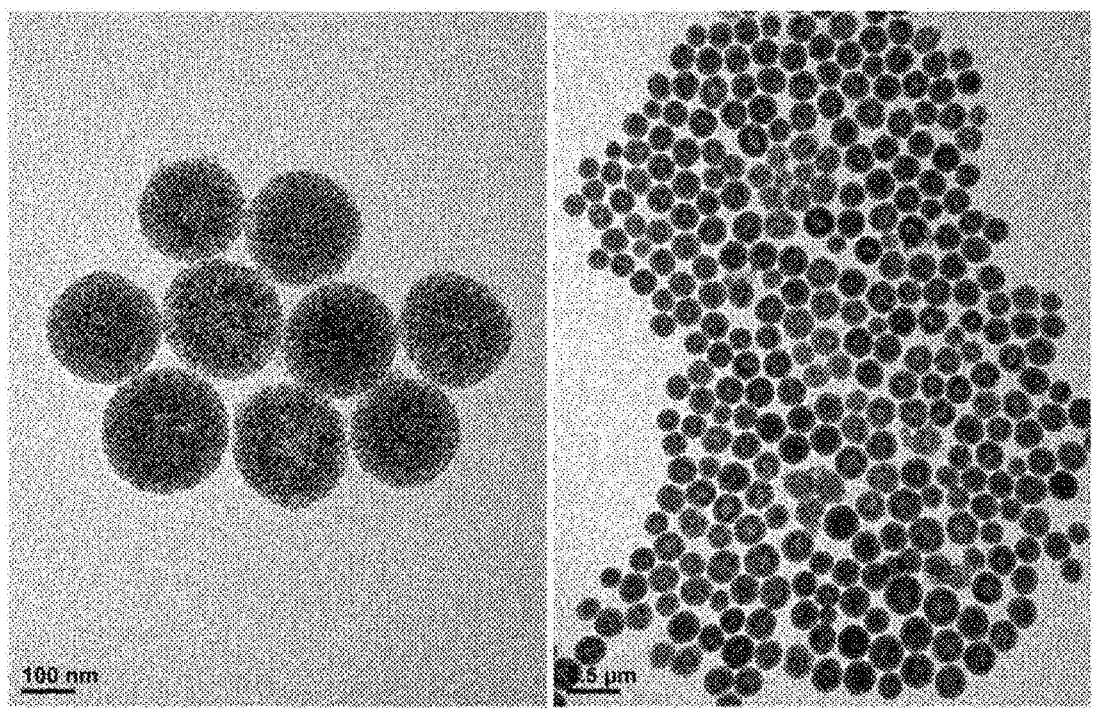
FIG. 2 is micrographs of porous silica particles according to one embodiment of the present invention.

FIG. 1 is photographs of the porous silica particles in Example 1-1-(1), and FIG. 2 is photographs of the porous silica particles in Example 1-1-(2), and from these drawings, it can be seen that spherical porous silica particles having sufficiently expanded pores were formed evenly.

Figure 3:
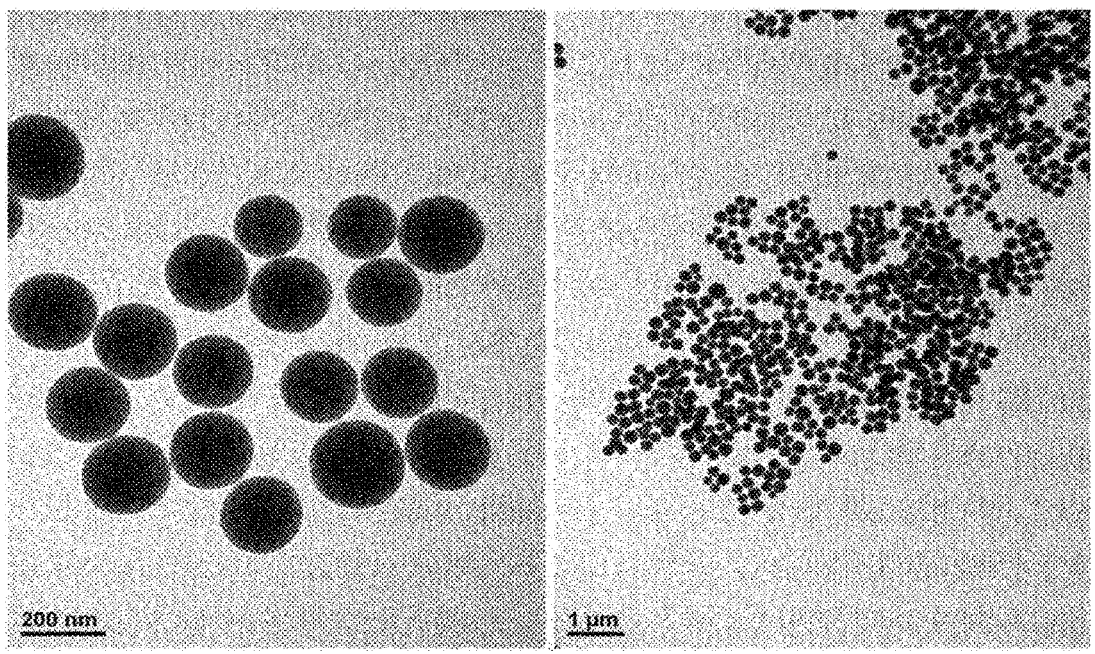
FIG. 3 is micrographs of small pore particles obtained in a manufacturing process of the porous silica particles according to one embodiment of the present invention.
Figure 4:
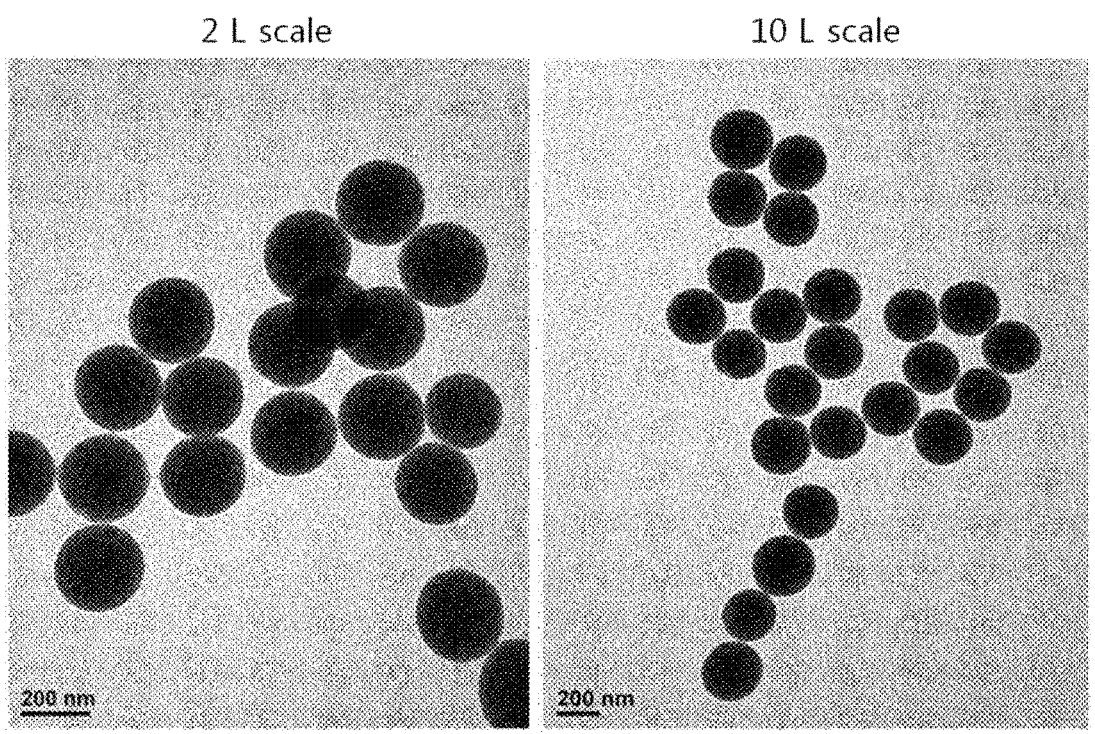
FIG. 4 is micrographs of the small pore particles according to one embodiment of the present invention.

FIG. 3 is photographs of the small pore particles in Example 1-1-(1), and FIG. 4 is comparative photographs of the small pore particles in Examples 1-1-(1) and 1-1-(3), and from these drawings, it can be seen that spherical small pore particles were formed evenly.

4. Calculation of BET Surface Area and Pore Diameter

Surface areas of the small pore particles in Example 1-1-(1) and the porous silica particles of Examples 1-1-(1), (7), (8), (10) and (11) were calculated. The surface areas were calculated by Brunauer-Emmett-Teller (BET) method, and the pore size distributions were calculated by Barrett-Joyner-Halenda (BJH) method.

Figure 5:
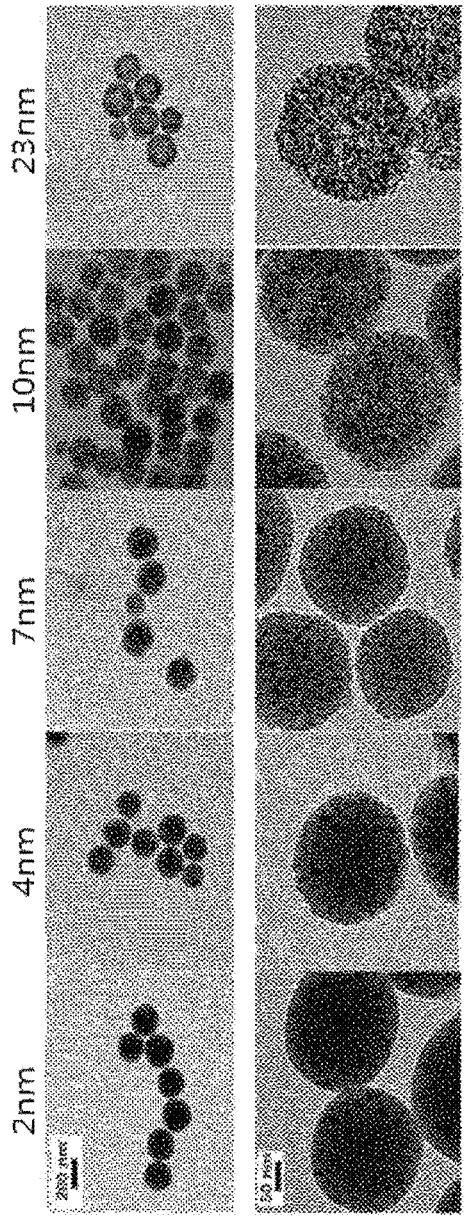
FIG. 5 is micrographs of the porous silica particles for each pore diameter according to one embodiment of the present invention. DDV (Degradable Delivery Vehicle) is the particles according to an embodiment, wherein the number in parenthesis means the diameter of the particle and the number of subscripts means the pore diameter. For example, DDV (200)$_{10}$ refers to a particle having a particle diameter (that is, particle size) of 200 nm and a pore diameter of 10 nm according to an embodiment.

Micrographs of the particles are shown in FIG. 5, and the calculation results are shown in Table 1 below.

TABLE 1

| Section | Pore diameter (nm) | BET surface area (m$^2$/g) |
|---|---|---|
| Small pore particle in Example 1-1-(1) | 2.1 | 1337 |
| Example 1-1-(7) | 4.3 | 630 |
| Example 1-1-(8) | 6.9 | 521 |
| Example 1-1-(1) | 10.4 | 486 |
| Example 1-1-(10) | 23 | 395 |
| Example 1-1-(11) | 12.3 | 379 |

5. Identification of Biodegradability

Figure 6:
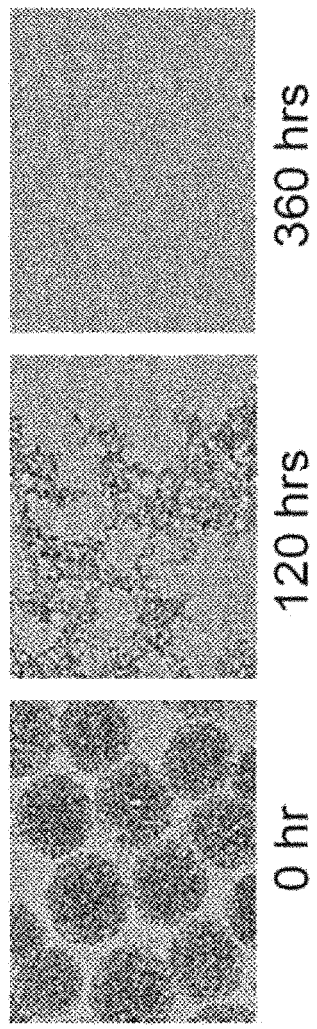
FIG. 6 is micrographs to identify biodegradability of the porous silica particles according to one embodiment of the present invention.

In order to identify biodegradability of the porous silica particles in Example 1-1-(1), biodegradability at 37° C. in SBF (pH 7.4) was observed under a microscope at 0 hours, 120 hours and 360 hours, and results thereof are shown in FIG. 6.

Referring to FIG. 6, it can be seen that the porous silica particles are biodegraded and almost degraded after 360 hours.

6. Measurement of Absorbance Ratio

Absorbance ratio over time was measured according to Equation 1 below.

$$A_t/A_0 \qquad \text{[Equation 1]}$$

(wherein $A_0$ is absorbance of the porous silica particles measured by putting 5 ml of suspension containing 1 mg/ml of the porous silica particles into a cylindrical permeable membrane having pores with a pore diameter of 50 kDa, 15 ml of the same solvent as the suspension comes into contact with an outside of the permeable membrane, and the inside/outside of the permeable membrane are horizontally stirred at 60 rpm and 37° C., and $A_t$ indicates absorbance of the porous silica particles measured after lapse of "t" hours since $A_0$ was measured).

Figure 7:
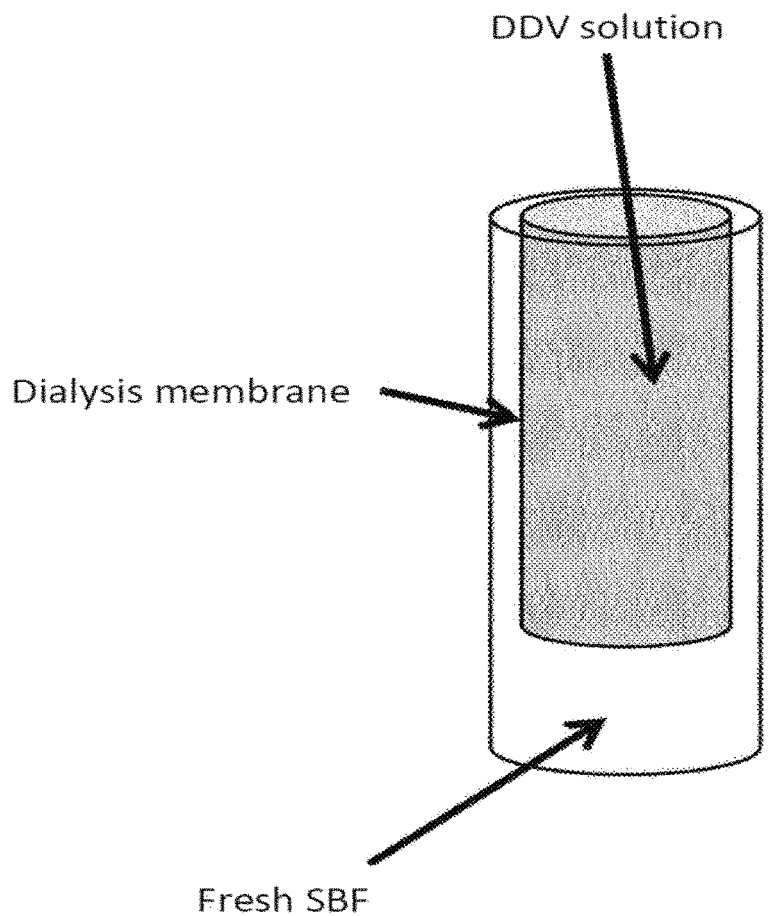
FIG. 7 a view illustrating a tube having a cylindrical permeable membrane according to one illustrative example.

Specifically, 5 mg of porous silica particle powder was dissolved in 5 ml of SBF (pH 7.4). Thereafter, 5 ml of porous silica particle solution was placed in a permeable membrane having pores with a pore diameter of 50 kDa shown in FIG. 7. 15 ml of SBF was added to the outer membrane, and the SBF on the outer membrane was replaced every 12 hours. Degradation of the porous silica particles was performed at 37° C. under horizontal stirring at 60 rpm.

Then, the absorbance was measured by UV-vis spectroscopy and analyzed at λ=640 nm.

(1) Measurement of Absorbance Ratio

Figure 8:
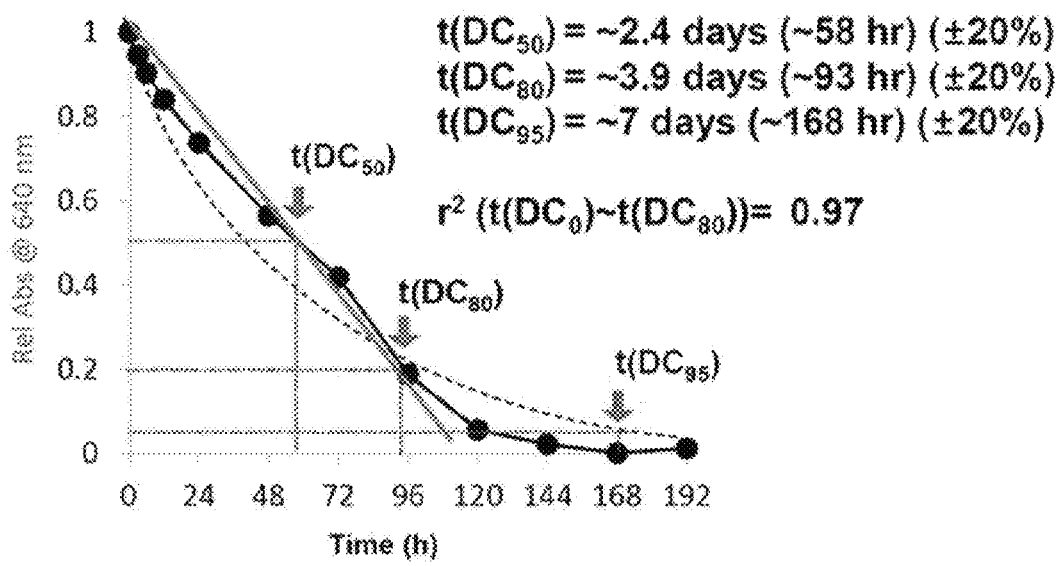
FIG. 8 is a graph illustrating results of decreasing absorbance of the porous silica particles over time according to one embodiment of the present invention.

Absorbance ratio of the porous silica particles in Example 1-1-(1) was measured according to the above method, and results thereof are shown in FIG. 8.

Referring to FIG. 8, it can be seen that t, at which the absorbance ratio becomes 1/2, is about 58 hours to demonstrate very slow degradation.

(2) Particle Size

Figure 9:
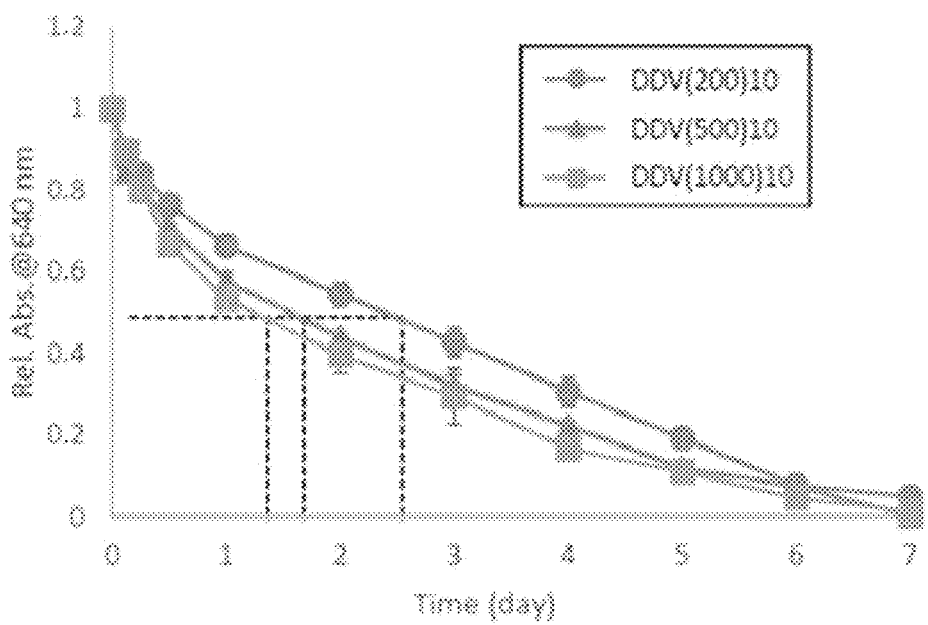
FIG. 9 is diagrams illustrating results of decreasing absorbance of the porous silica particles for each particle size over time according to one embodiment of the present invention.

Absorbances of the porous silica particles in Examples 1-1-(1), (5) and (6) were measured according to Equation 1 above, and results thereof are shown in FIG. 9 (SBF used as the suspension and the solvent).

Referring to FIG. 9, it can be seen that t is decreased as the particle size is increased.

(3) Average Pore Diameter

Figure 10:
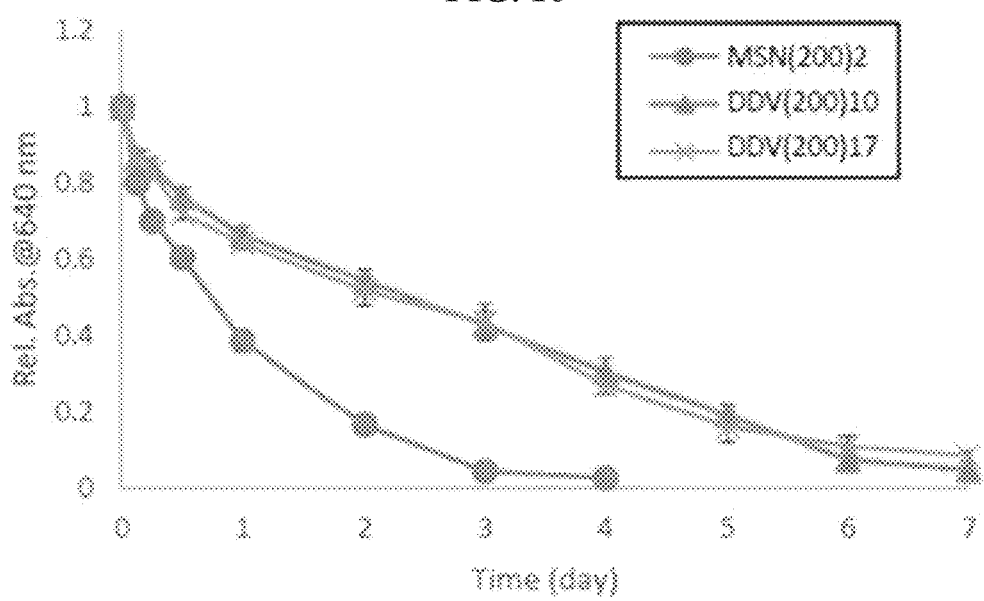
FIG. 10 is diagrams illustrating results of decreasing absorbance of the porous silica particles for each pore diameter over time according to one embodiment of the present invention.

Absorbances of the porous silica particles in Examples 1-1-(1) and (9) and the microporous silica particles in Example 1-1-(1) as a control were measured according to Equation 1 above, and results thereof are shown in FIG. 10 (SBF used as the suspension and the solvent).

Referring to FIG. 10, it can be seen that the porous silica particles of the inventive example have a significantly larger t than the control.

(4) pH

Absorbance of the porous silica particles in Example 1-1-(4) for each pH was measured. The absorbance was measured in SBF and in Tris at pH 2, 5, and 7.4, and results thereof are shown in FIG. 11.

Figure 11:
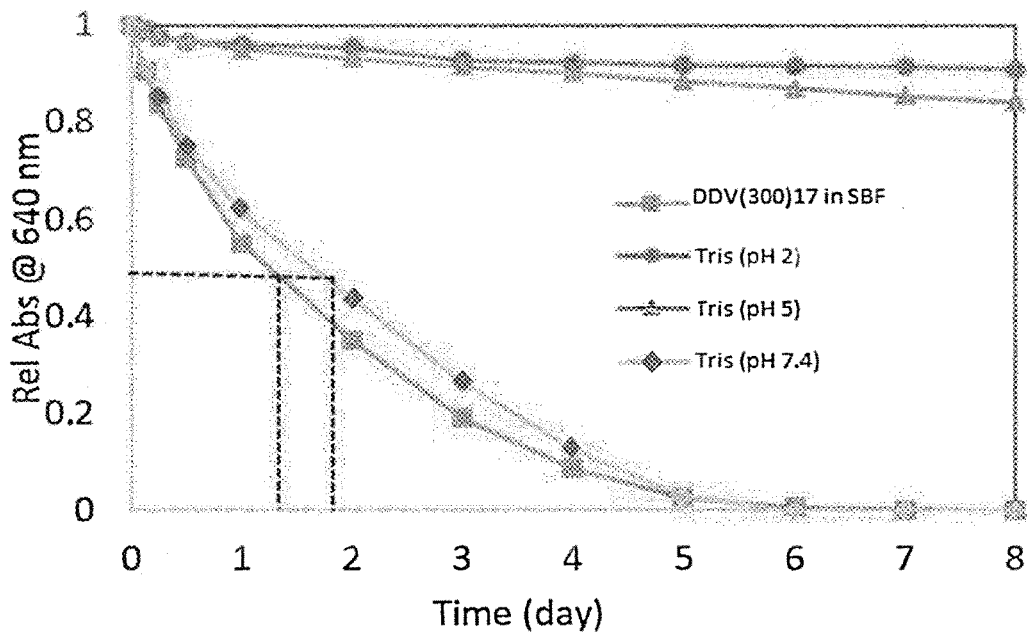
FIG. 11 is a graph illustrating results of decreasing absorbance of the porous silica particles for each pH of the environment over time according to one embodiment of the present invention.

Referring to FIG. 11, it could be seen that, although there is a difference in t in relation to pH, t at which all absorbance ratio becomes 1/2 was 24 or more.

(5) Charging

Figure 12:
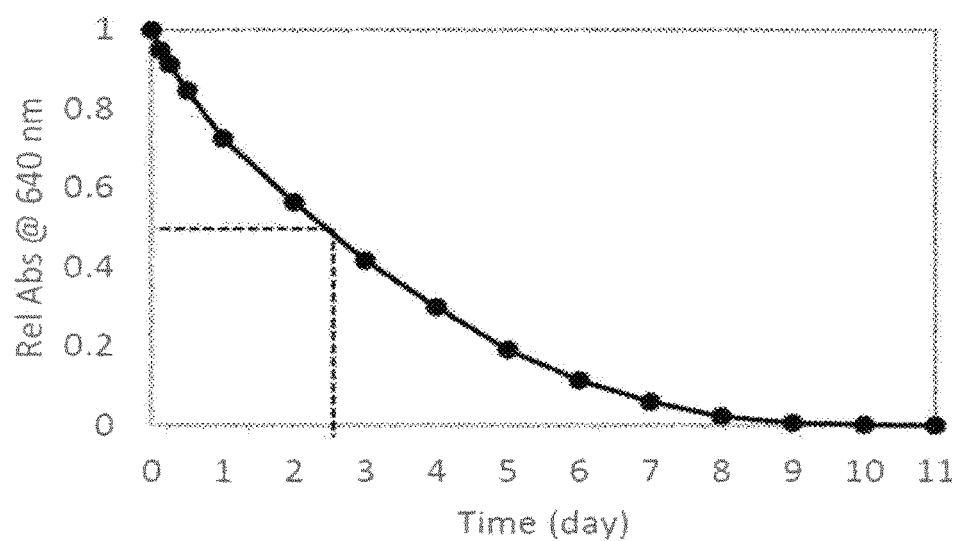
FIG. 12 is a graph illustrating results of decreasing absorbance of the porous silica particles over time according to one embodiment of the present invention.

Absorbance of the porous silica particles in Example 1-2-(1)-1) was measured, and results thereof are shown in FIG. 12 (Tris (pH 7.4) used as the suspension and the solvent).

Referring to FIG. 12, it could be seen that t at which the absorbance ratio of the positively charged particles becomes 1/2 was 24 or more.

Example 2: Preparation of DegradaBALL and Selection of CpG ODN and siIDO

1. Preparation of DegradaBALL

Porous silica particles were prepared by the same method as Example 1-1-(1) except that 920 ml of distilled water and 850 ml of methanol were used for preparing small pore particles, and 11 mL of TMB was used for pore expansion.

Figure 13C:
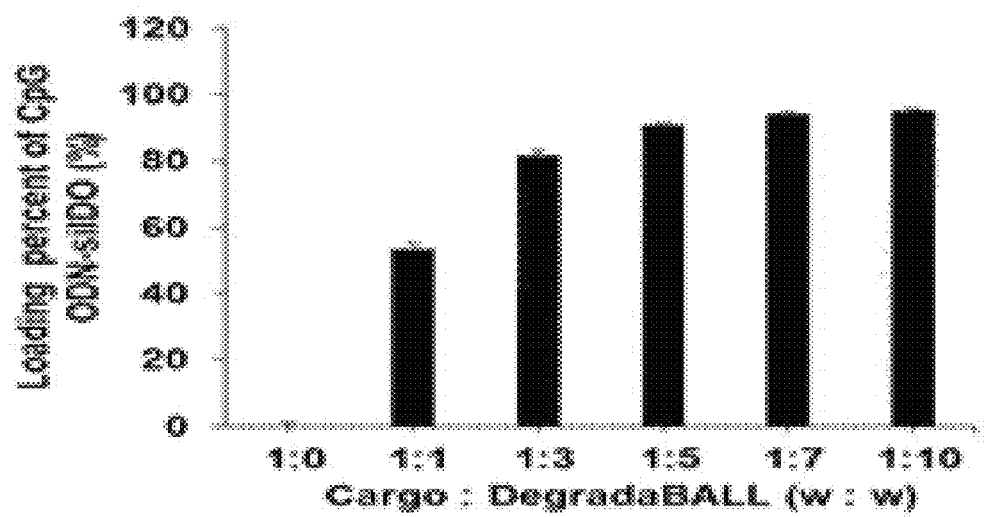
FIGS. 13C to 13H illustrate analyzed results of characteristics of porous silica particles (LEM-S403) loaded with the nucleic acid molecules according to an embodiment of the present invention.
Figure 13D:
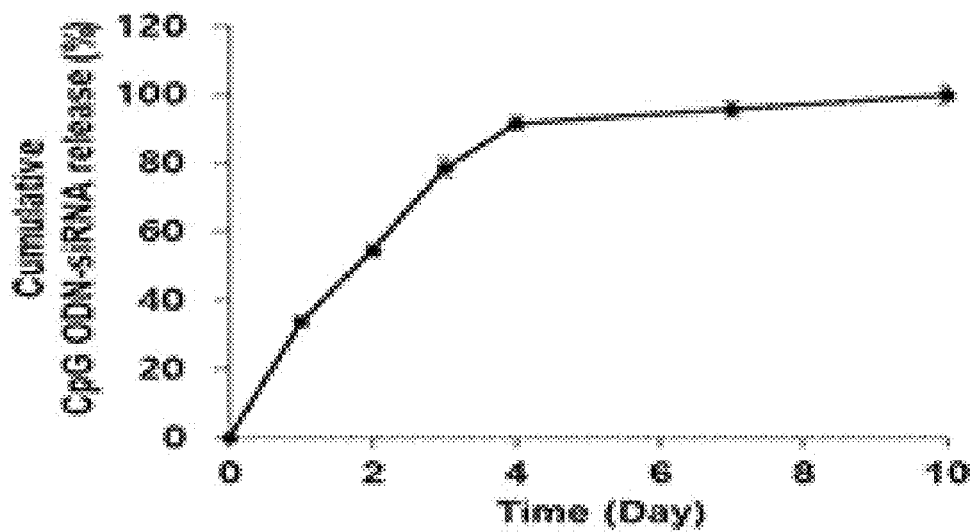
Figure 13E:
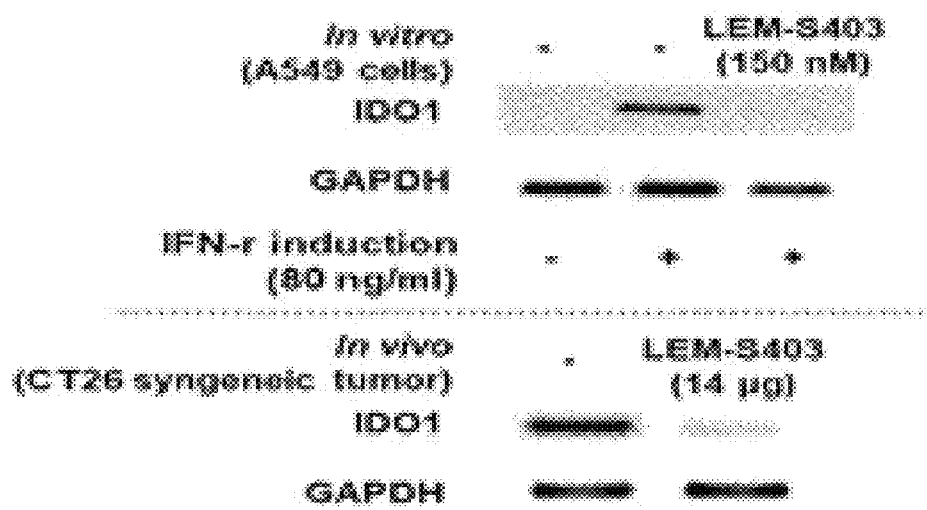
Figure 13F:
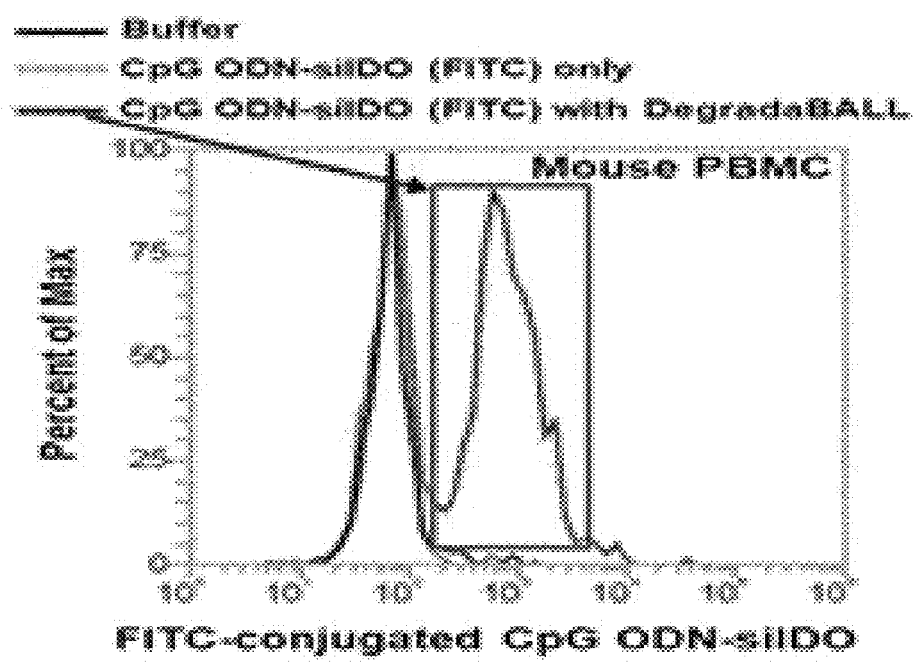
Figure 13G:
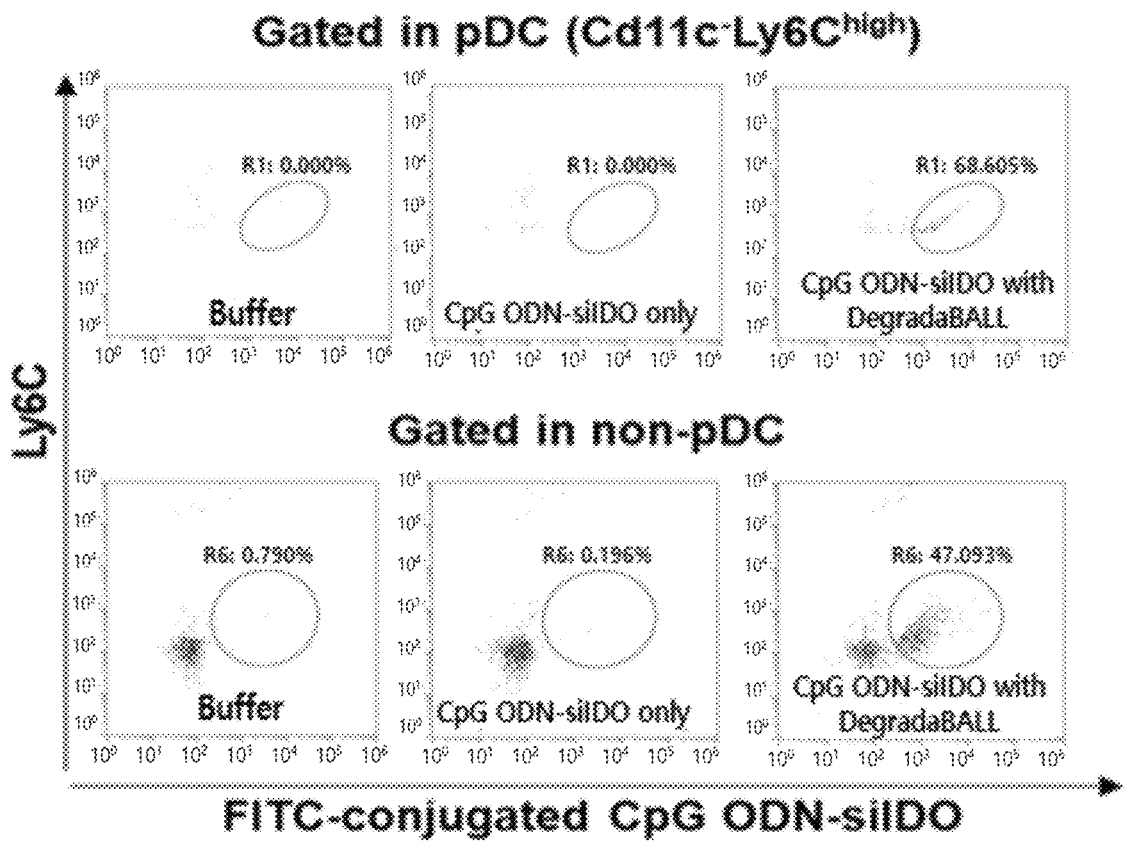
Figure 13H:
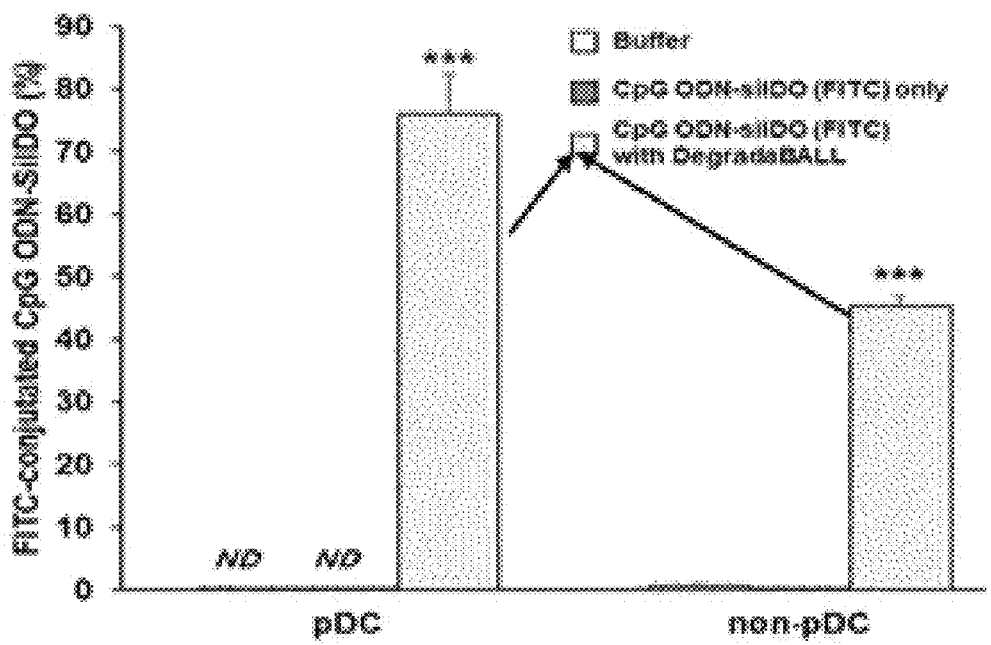
Figure 14A:
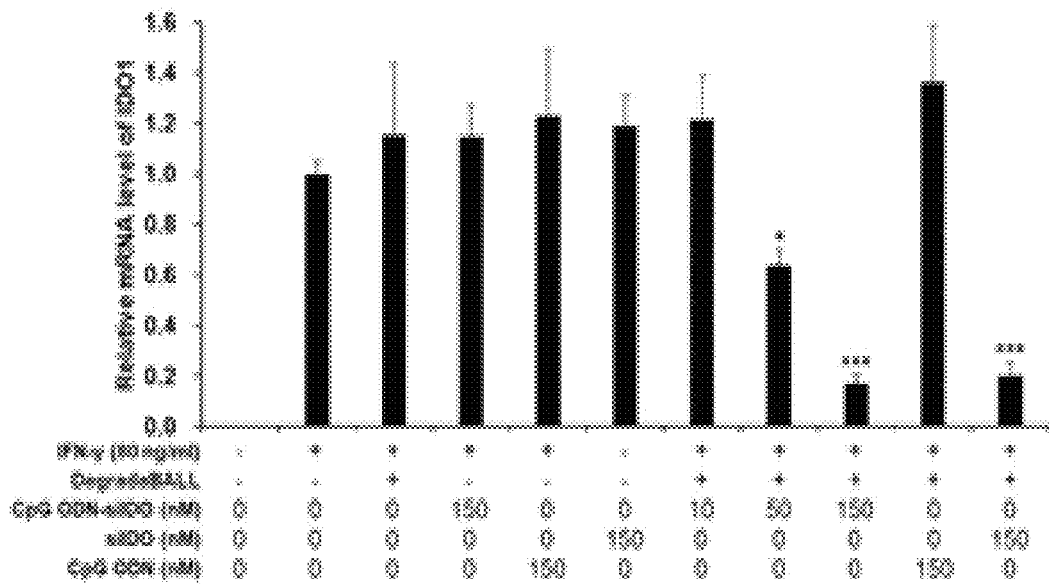
FIGS. 14A to 14E illustrate IDO1 gene knock-down efficiency and type I IFN induction efficiency of LEMIDO. Specifically, in FIG. 14A, A549 cells were treated with LEM-S403 with different concentrations (10, 50 and 150 nM) and a comparative control sample, respectively, for 12 hours. Thereafter, 80 ng/ml of IFN-γ was further added for 12 hours to induce IDO1 gene expression. Data (n=3 for each group) is represented by average±SEM. Comparison between groups was conducted by one-way ANOVA. (*p<0.05 and *p<0.001 vs only IFN-γ-treated group).
Figure 14B:
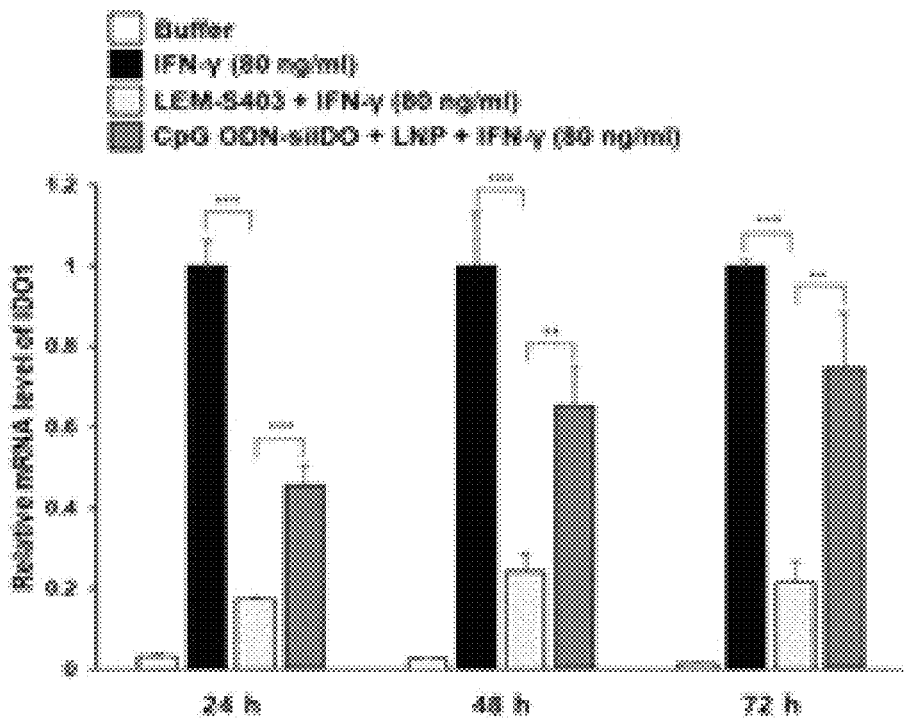
Figure 14C:
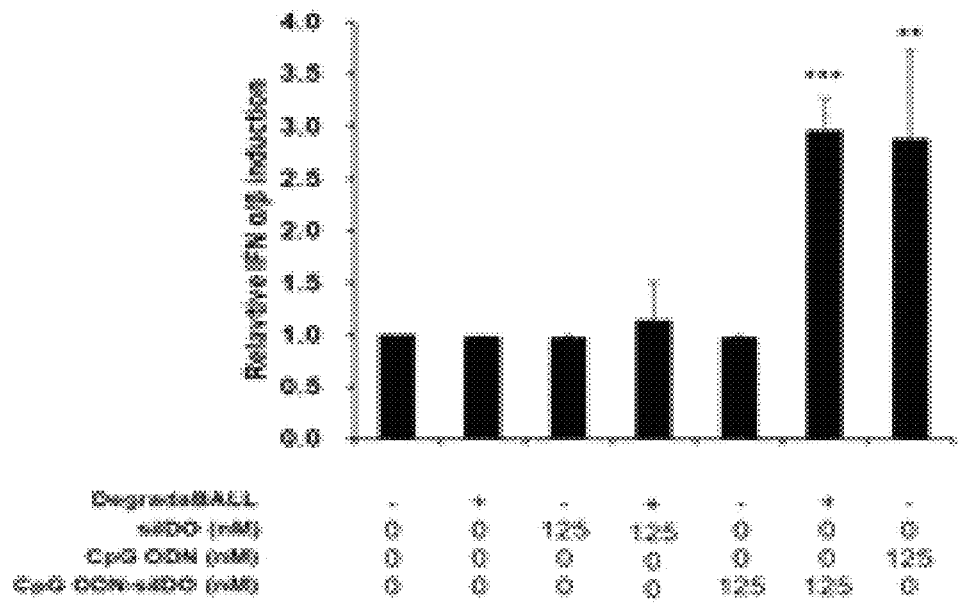
Figure 14D:
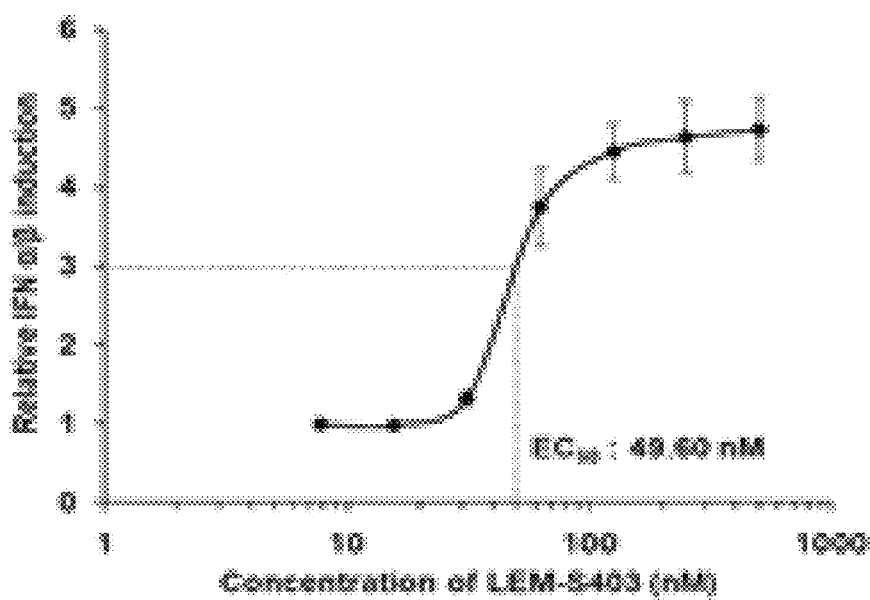
Figure 14E:
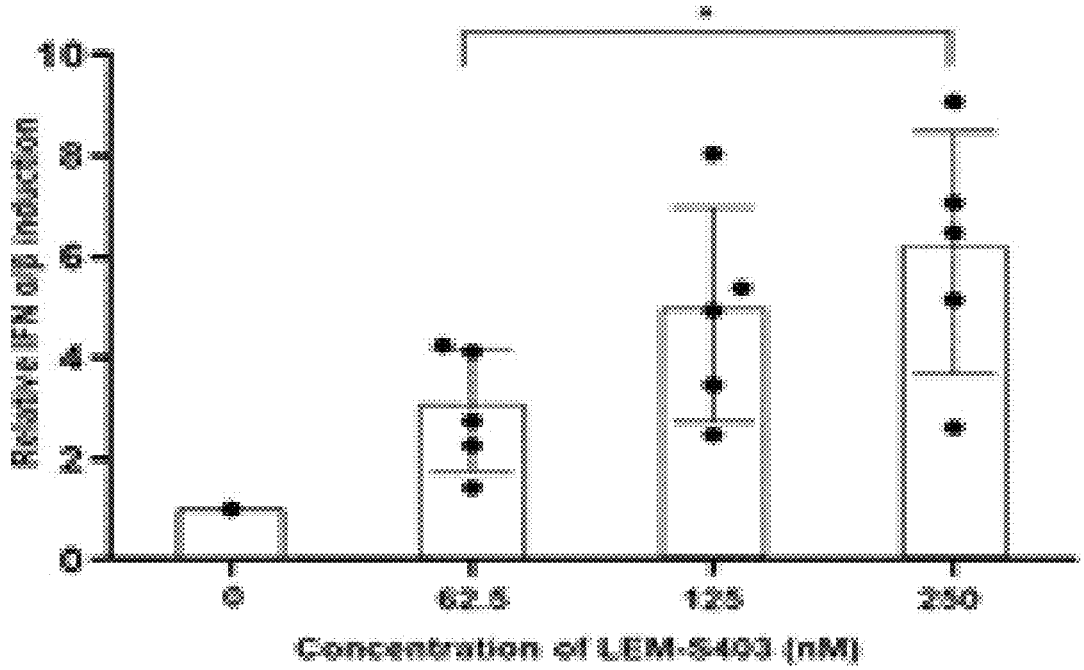
Figure 15A:
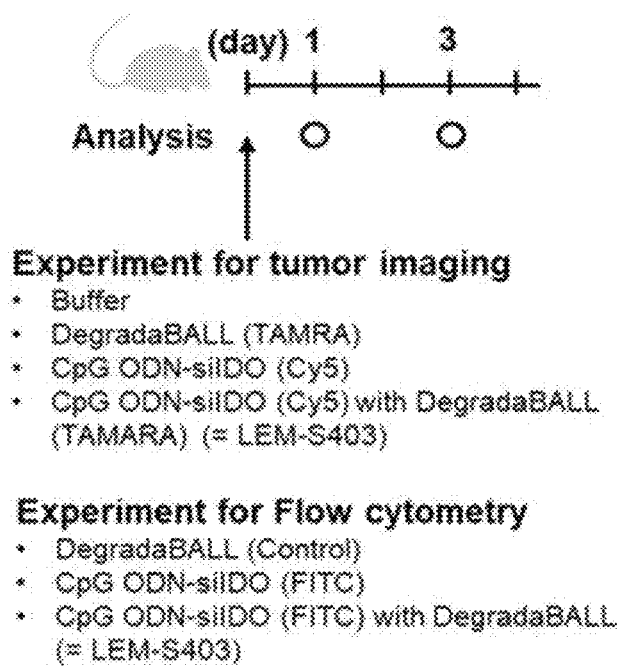
FIGS. 15A to 15C illustrate a sustained release system of LEM-S403 and enhanced bio-distribution in CT26 syngeneic mouse model.
Figure 15B:
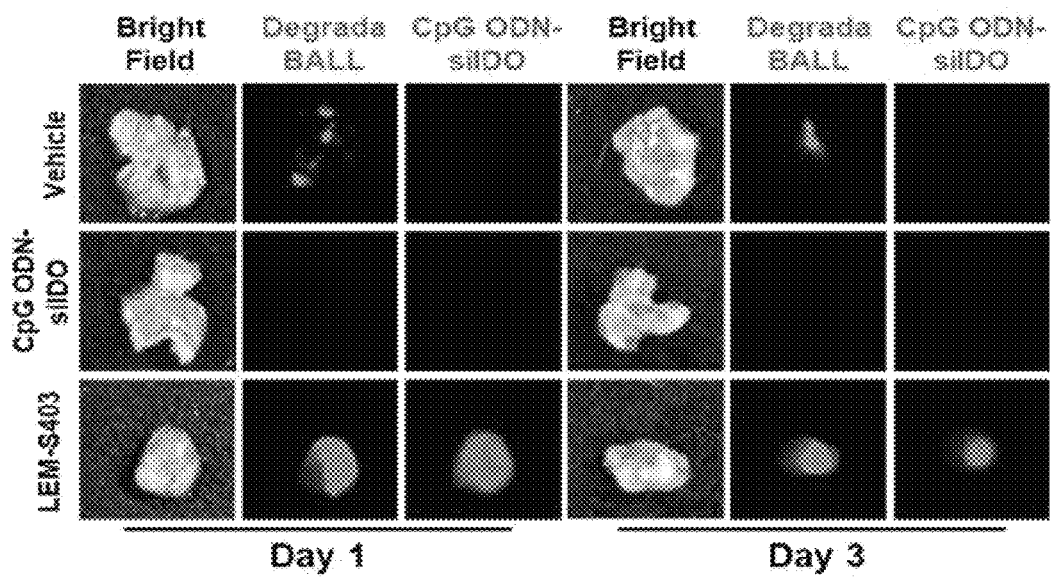
Figure 15C:
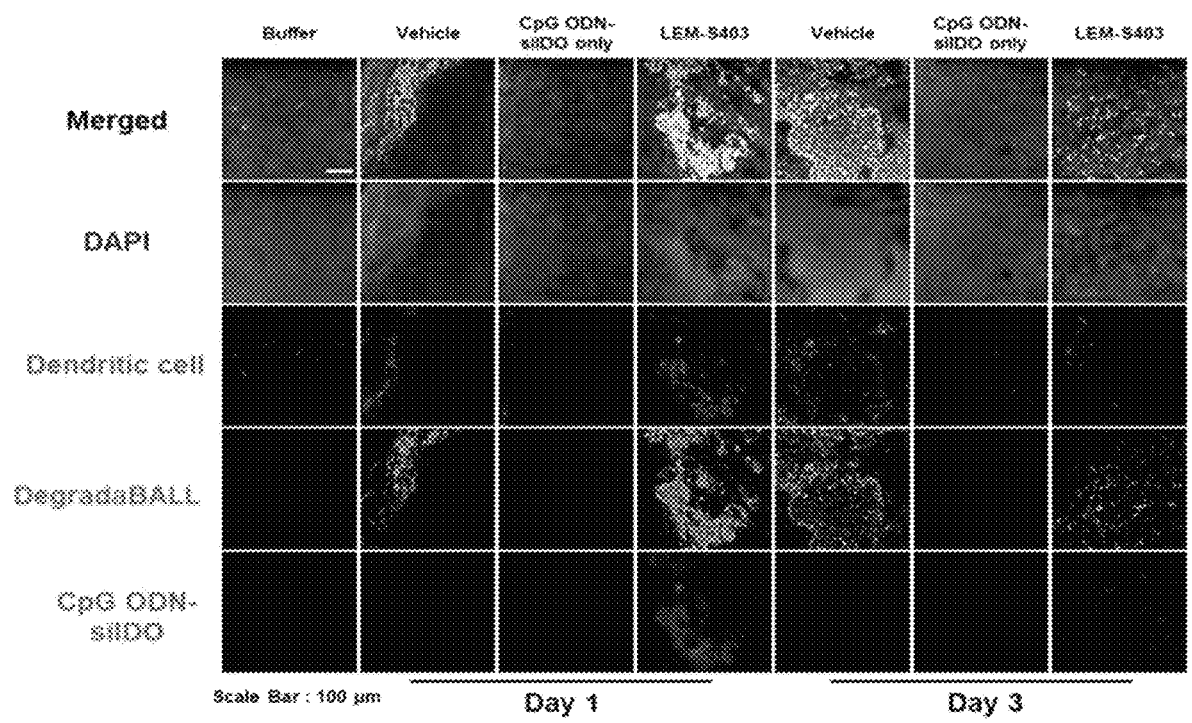
Figure 15D:
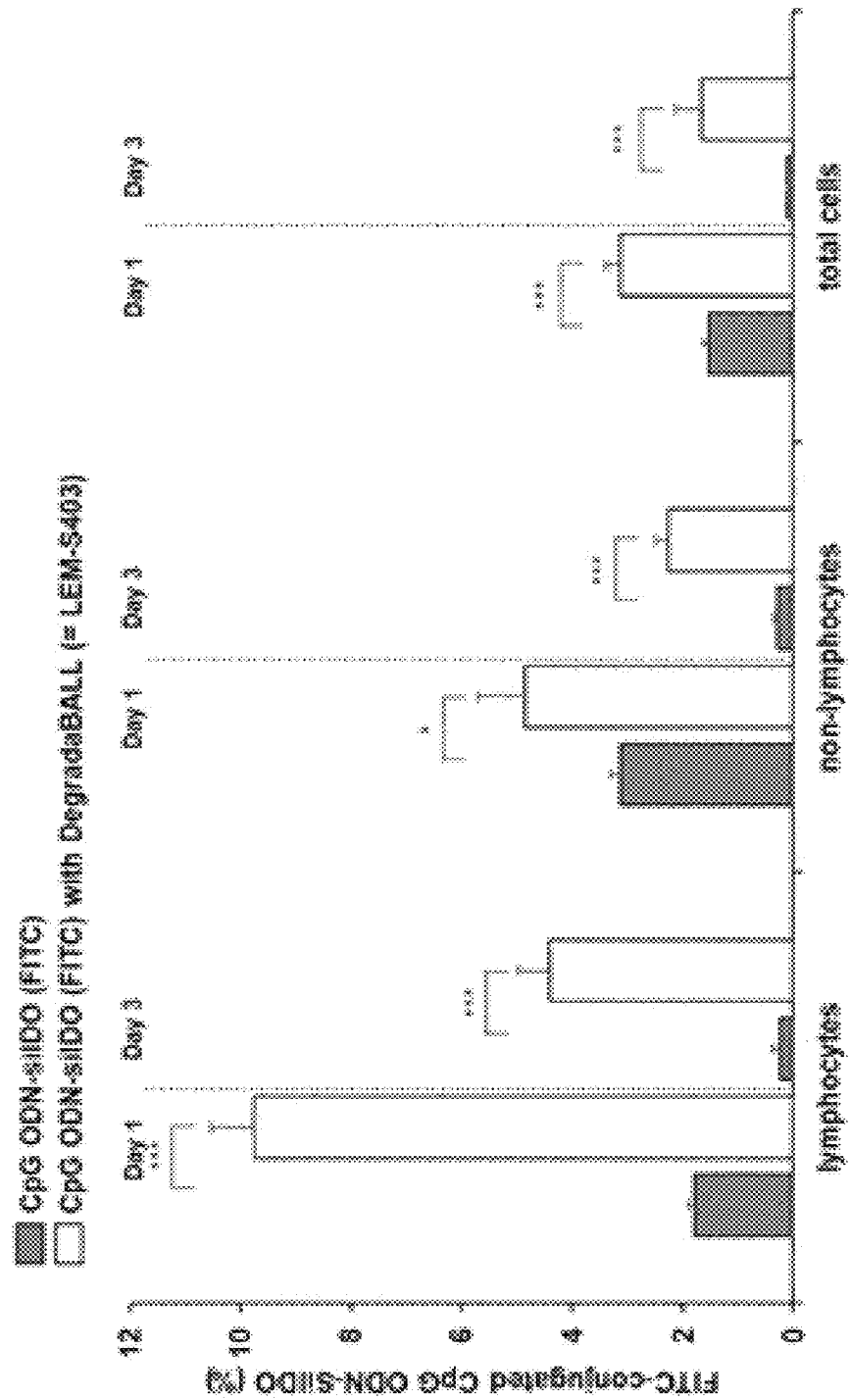
FIGS. 15D and 15E illustrate a sustained release system and enhanced bio-distribution of LEM-S403 in CT26 syngeneic mouse model. Specifically.
Figure 15E:
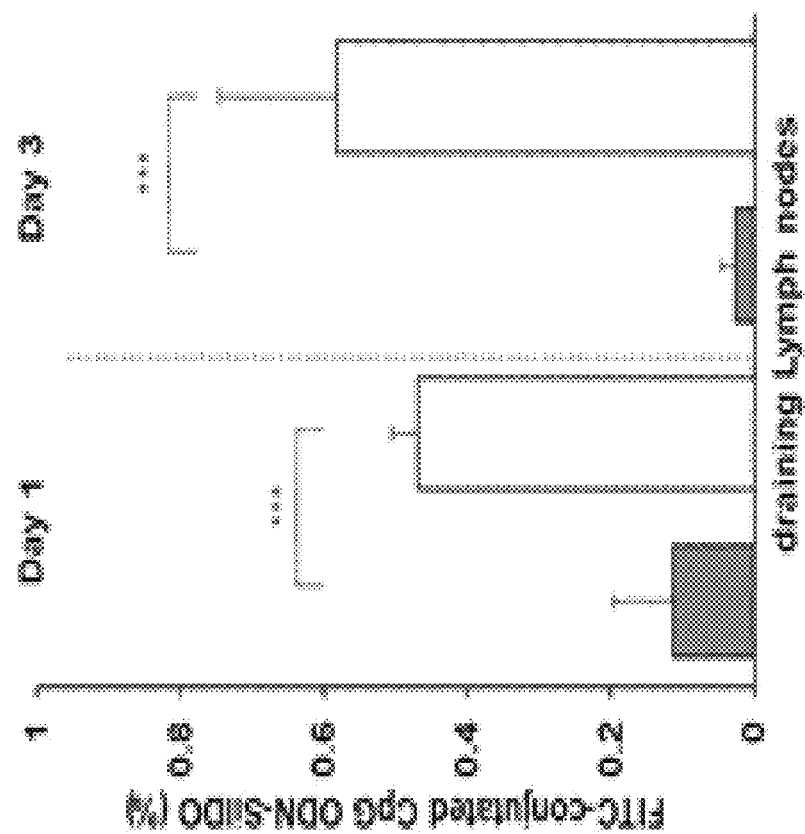
Figure 16A:
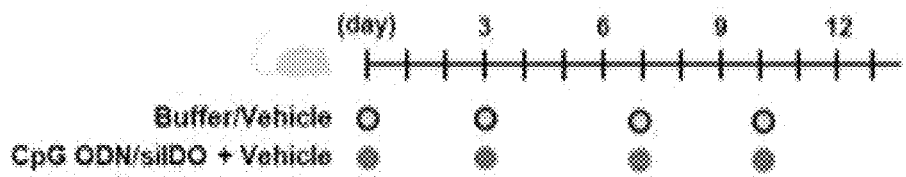
FIGS. 16A to 16F illustrate therapeutic efficacy of intra-tumoral injection of LEMIDO in CT26 syngeneic mouse model.
Figure 16B:
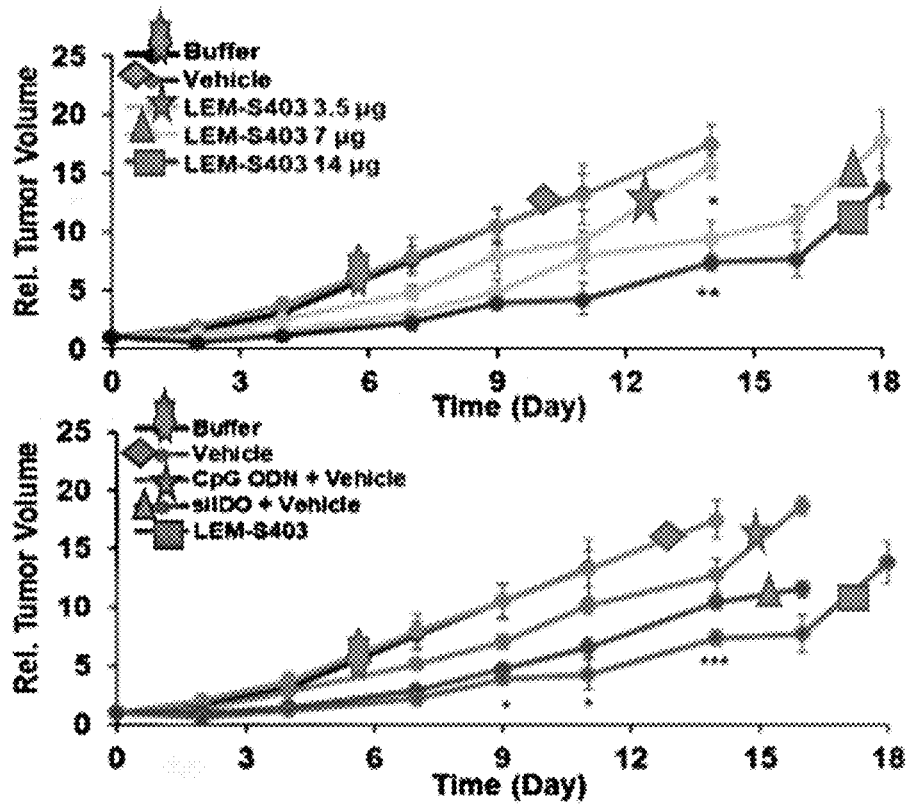
Figure 16C:
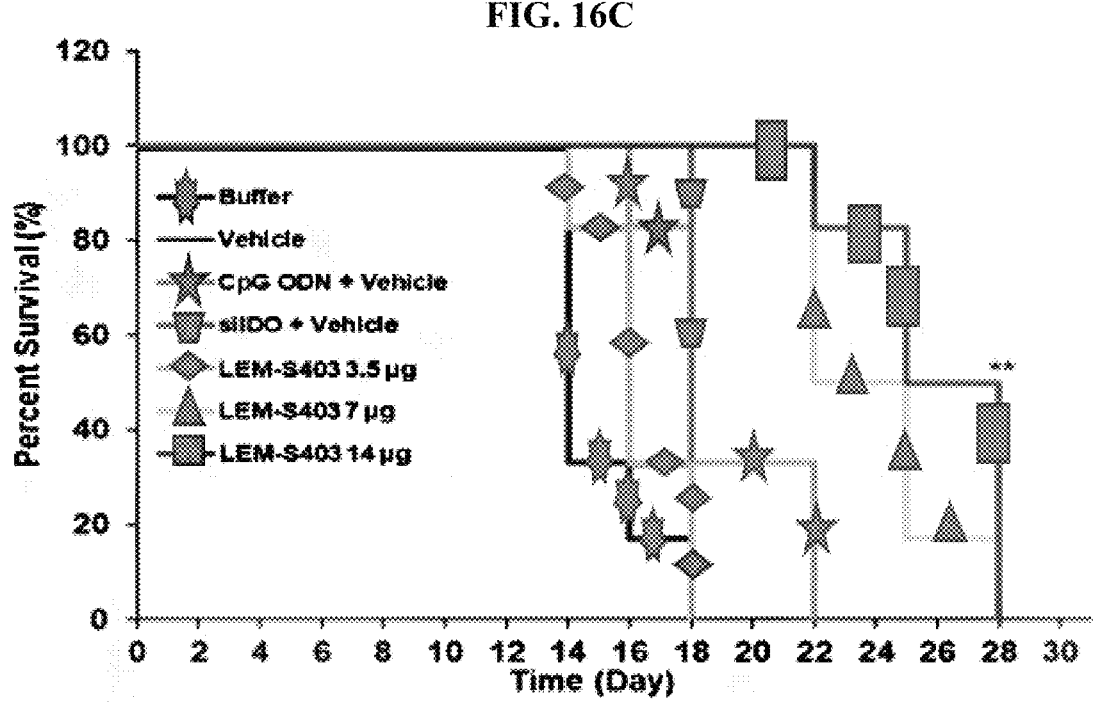
Figure 16D:
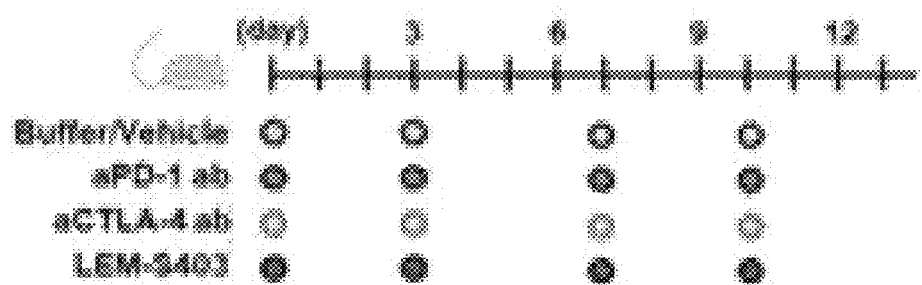
Figure 16E:
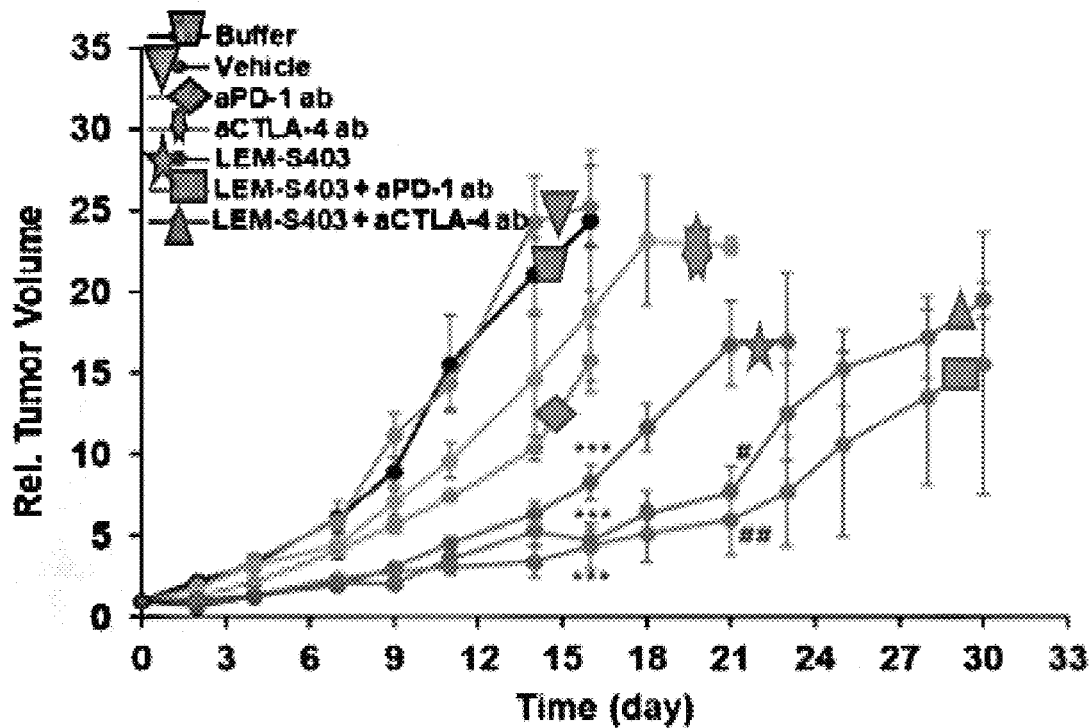
Figure 16F:
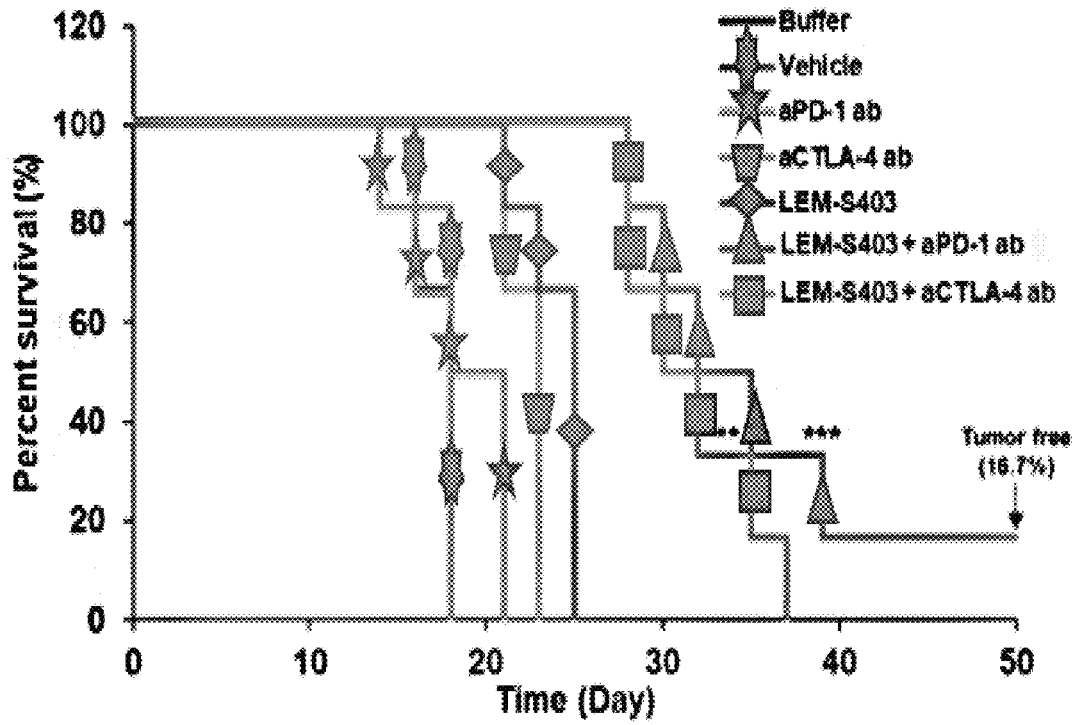
Figure 16G:
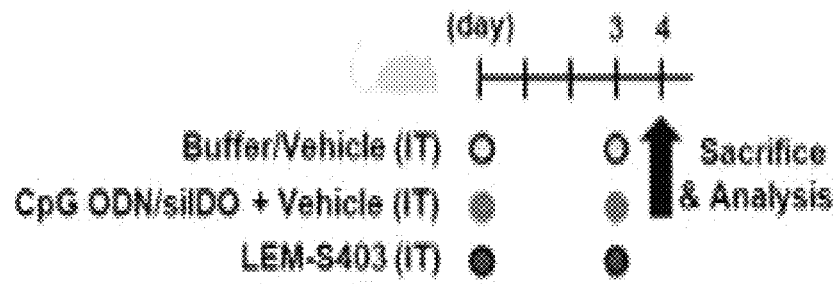
FIGS. 16G to 16L illustrate therapeutic efficacy of intra-tumoral injection of LEMIDO in CT26 syngeneic mouse model.
Figure 16H:
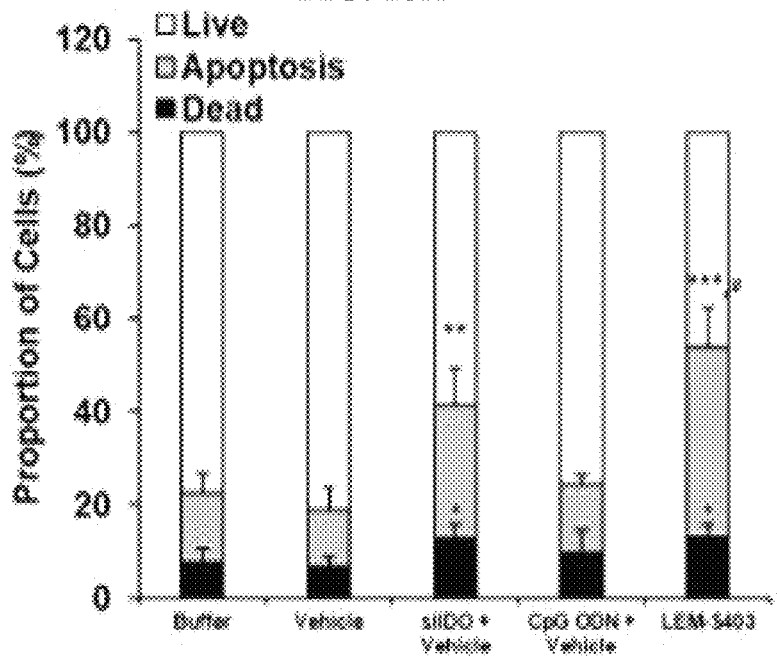
Figure 16I:
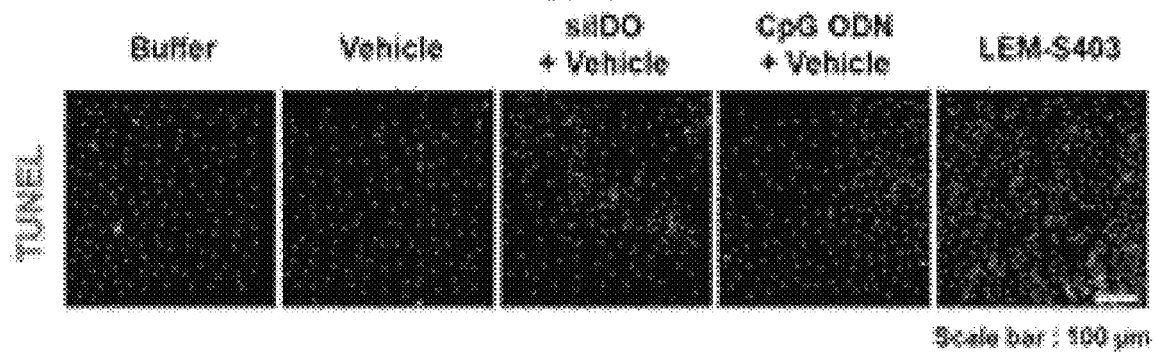
Figure 16J:
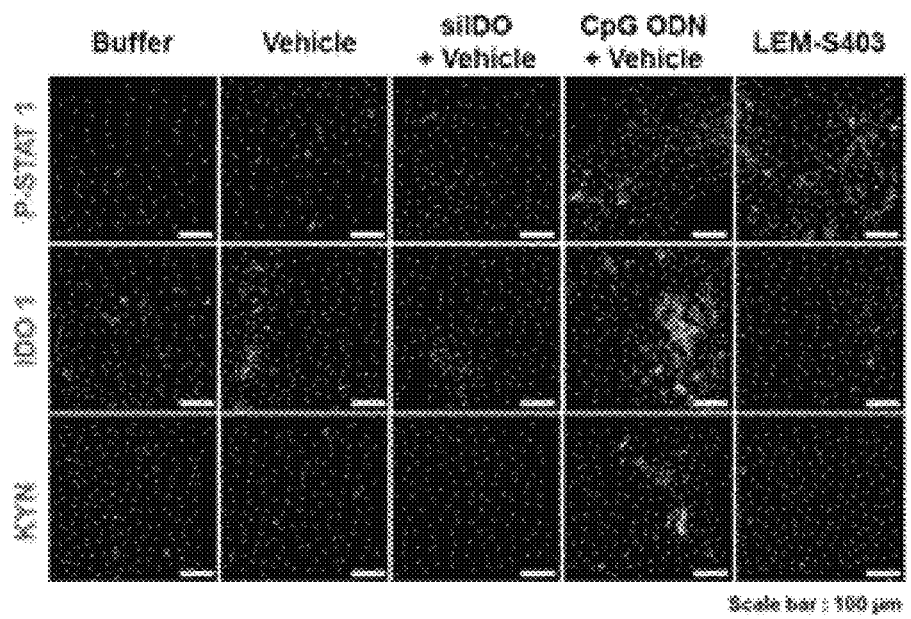
Figure 16K:
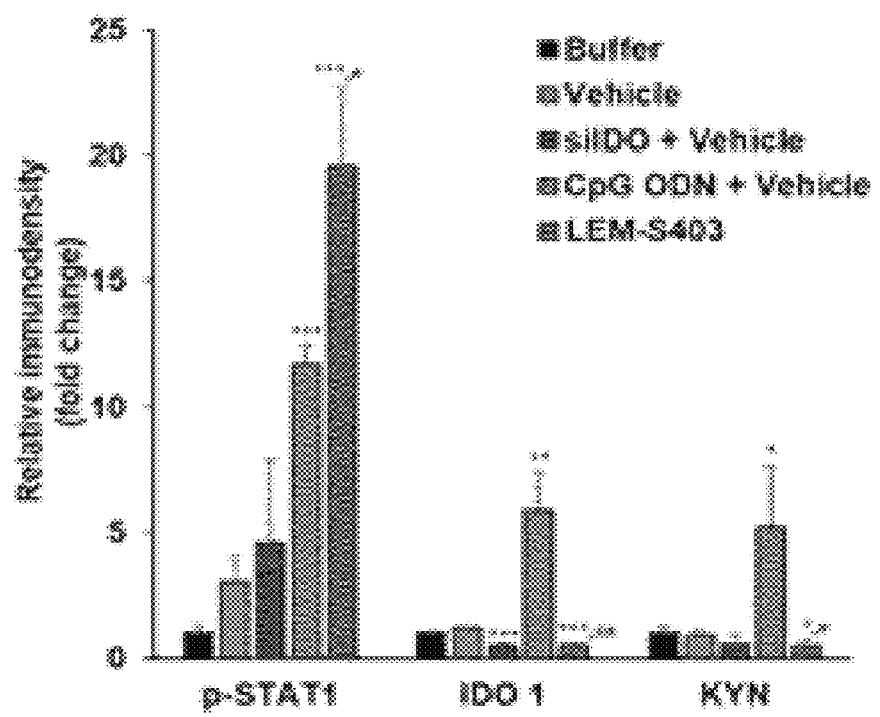
Figure 16L:
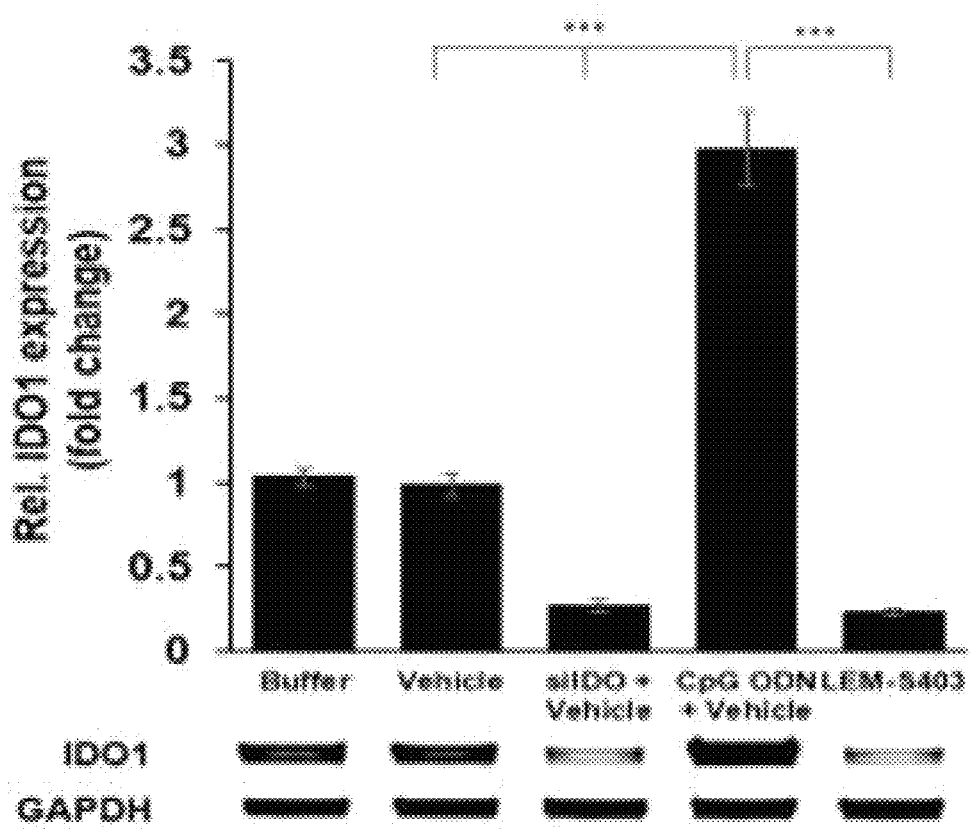
Figure 17A:
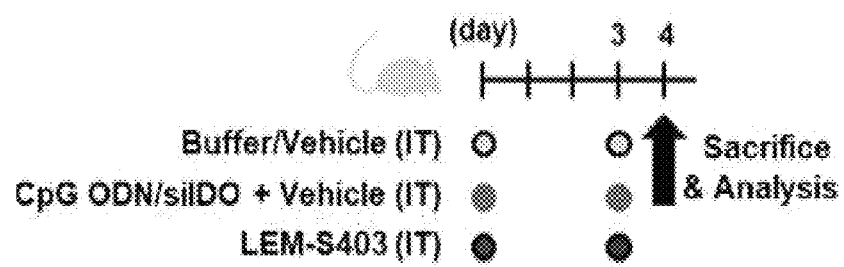
FIGS. 17A to 17C illustrate anti-tumor immune response of LEM-S403 in CT26 syngeneic mouse model.
Figure 17B:
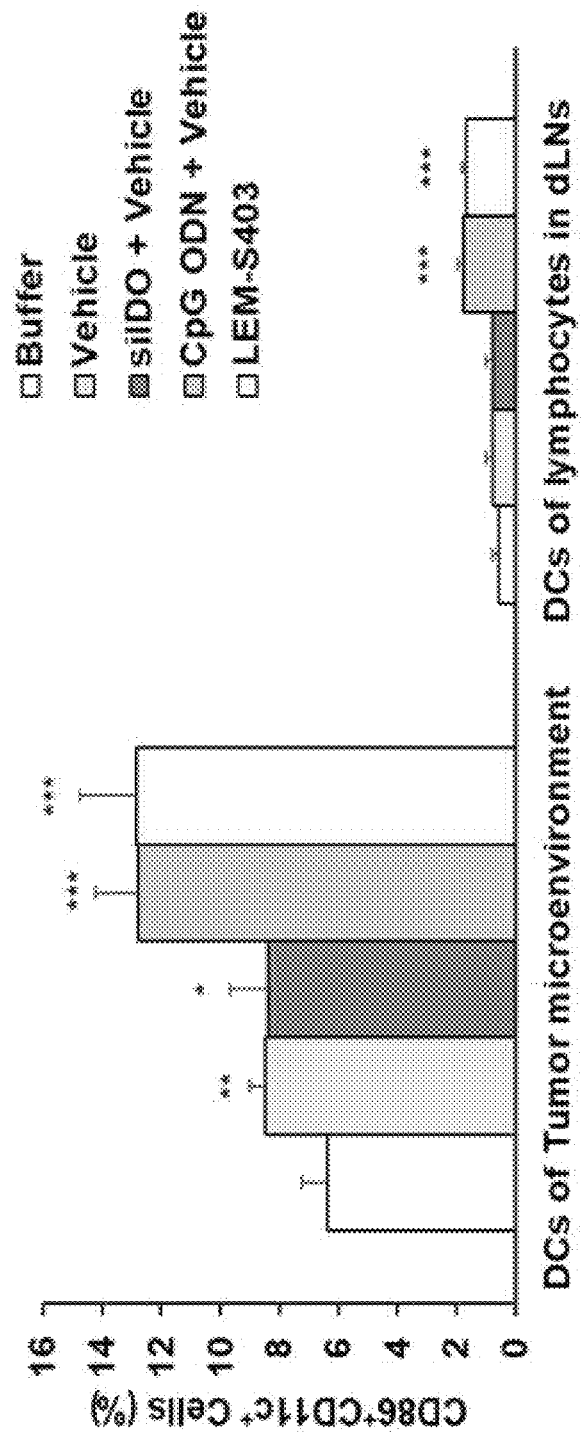
Figure 17C:
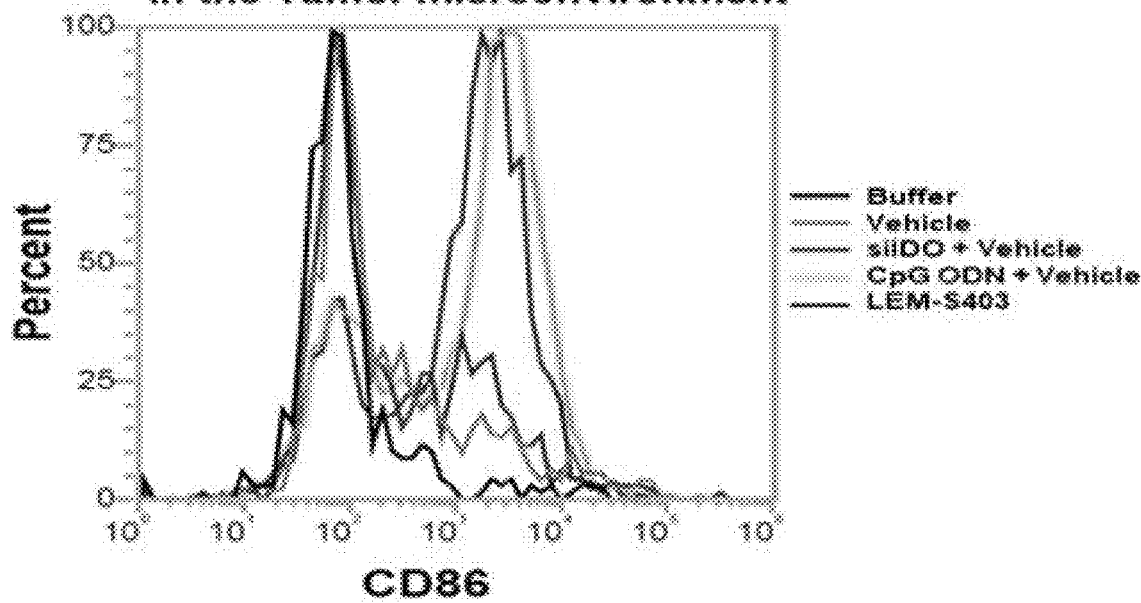
Figure 17D:
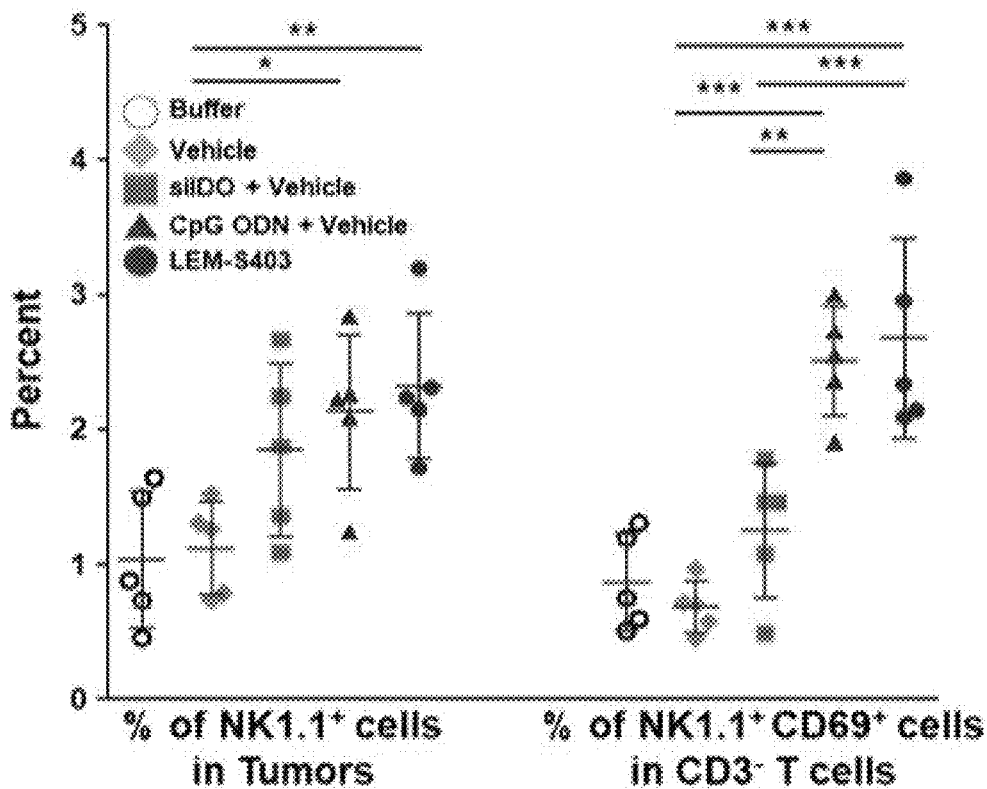
FIGS. 17D to 17I illustrate anti-tumor immune response of LEM-S403 in CT26 syngeneic mouse model.
Figure 17E:
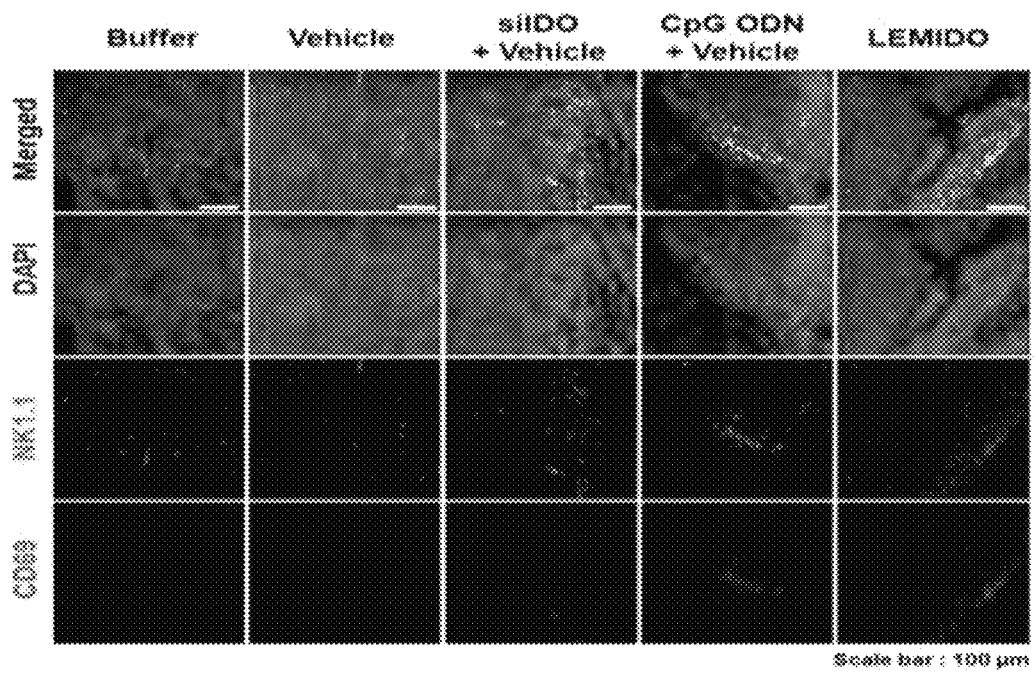
Figure 17F:
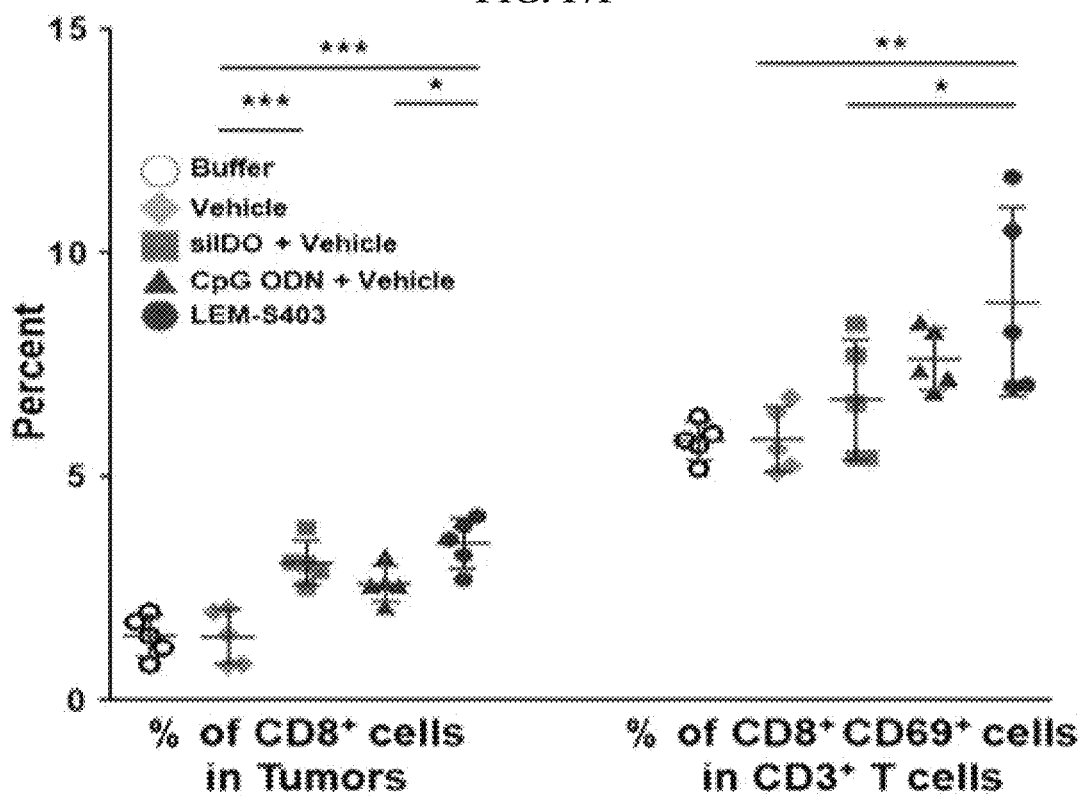
Figure 17G:
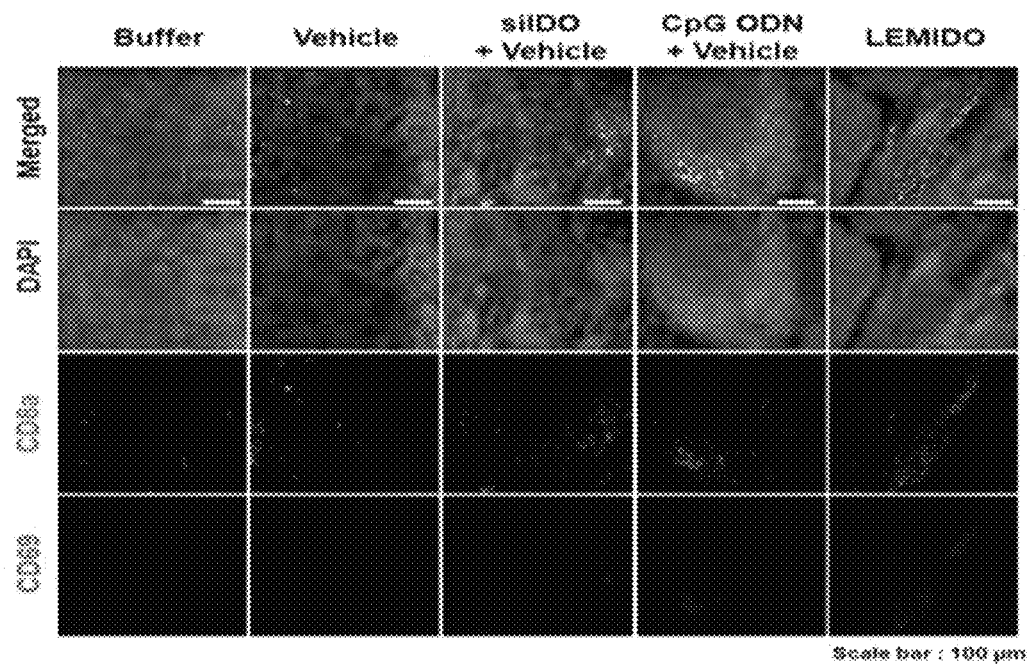
Figure 17H:
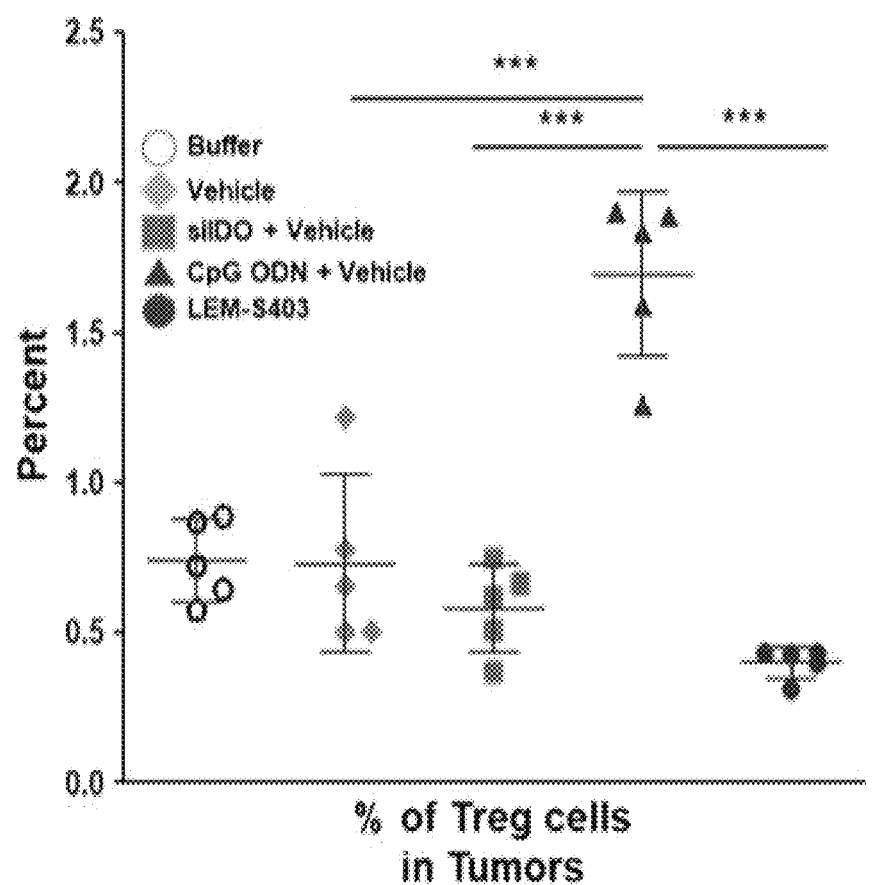
Figure 17I:
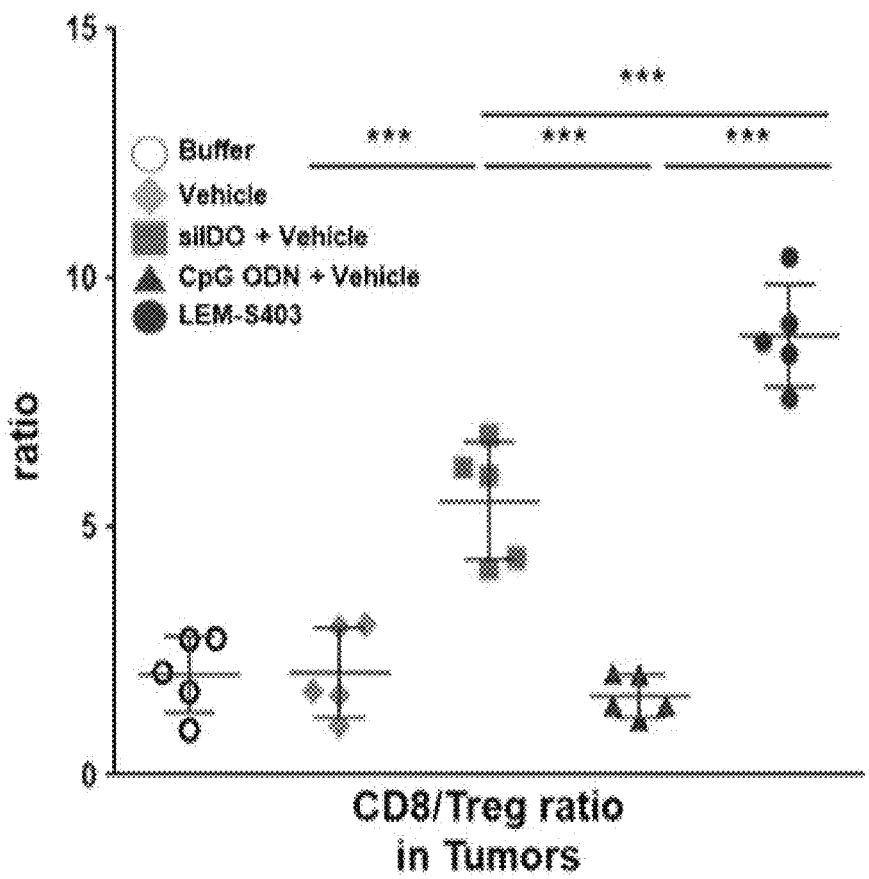
Figure 18A:
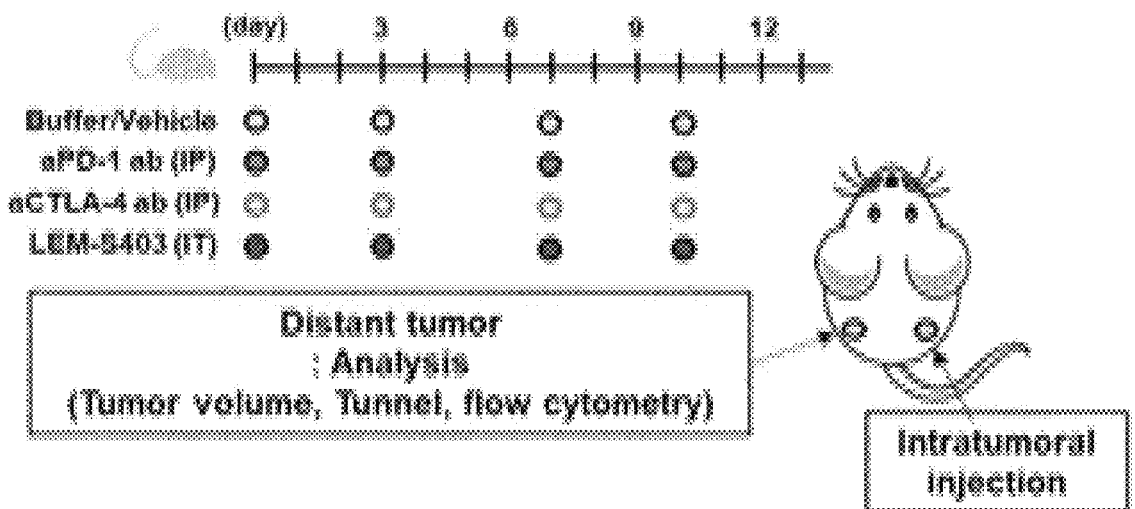
FIGS. 18A to 18C illustrate therapeutic effects of LEM-S403 to remote tumor in CT26 syngeneic mouse model (abscopal effects).
Figure 18B:
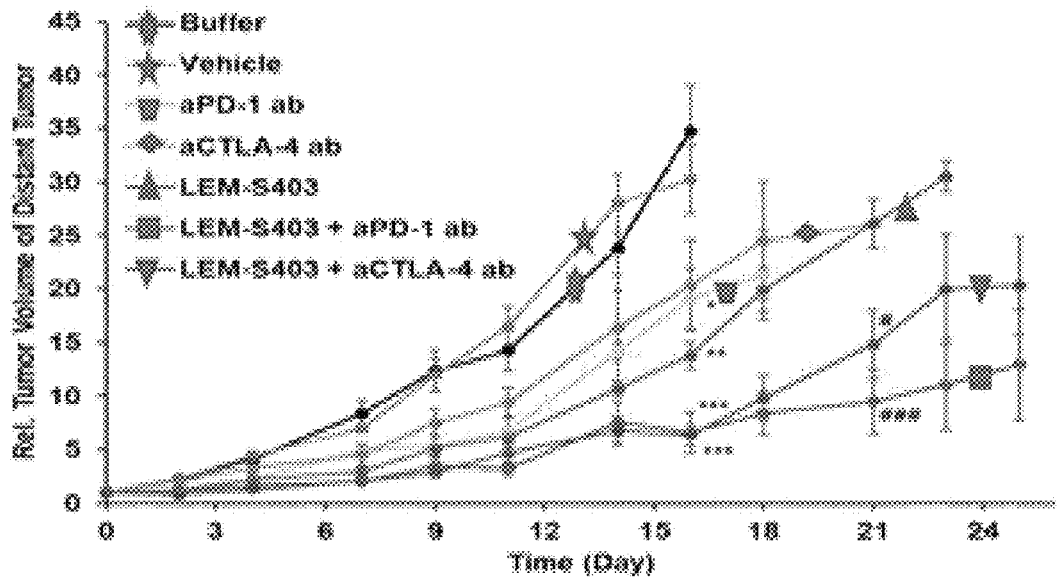
Figure 18C:
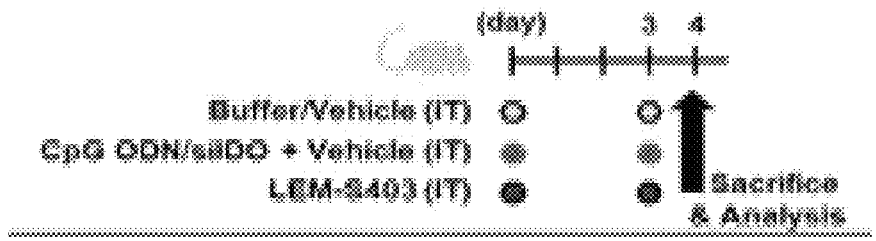
Figure 18D:
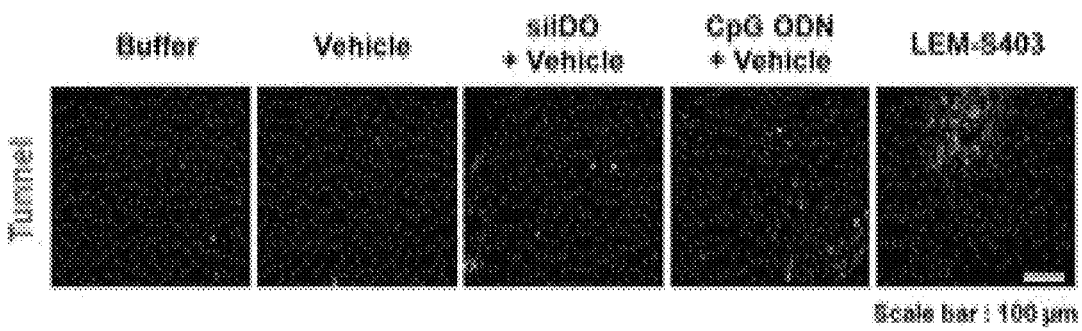
FIGS. 18D to 18H illustrate therapeutic effects of LEM-S403 to remote tumor in CT26 syngeneic mouse model (abscopal effects).
Figure 18E:
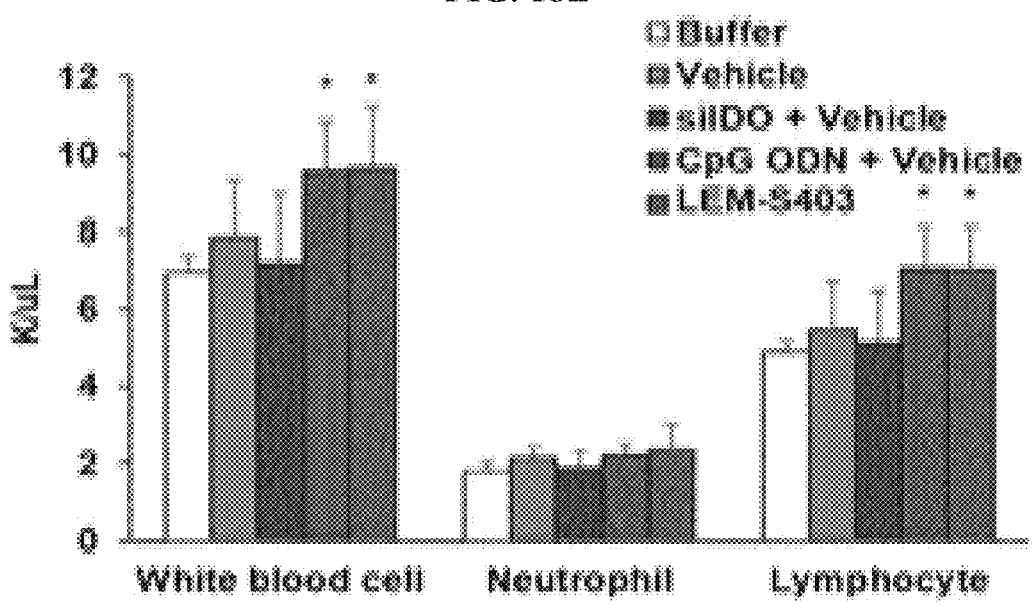
Figure 18F:
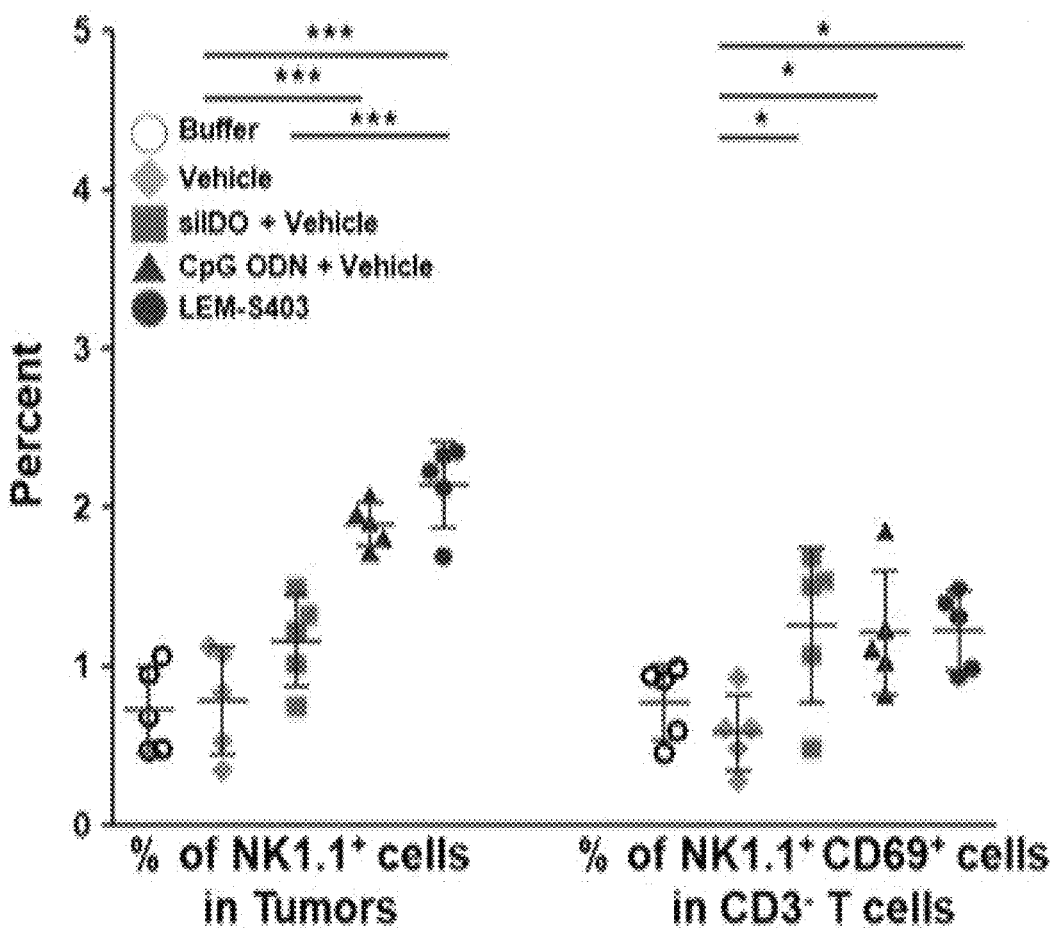
Figure 18G:
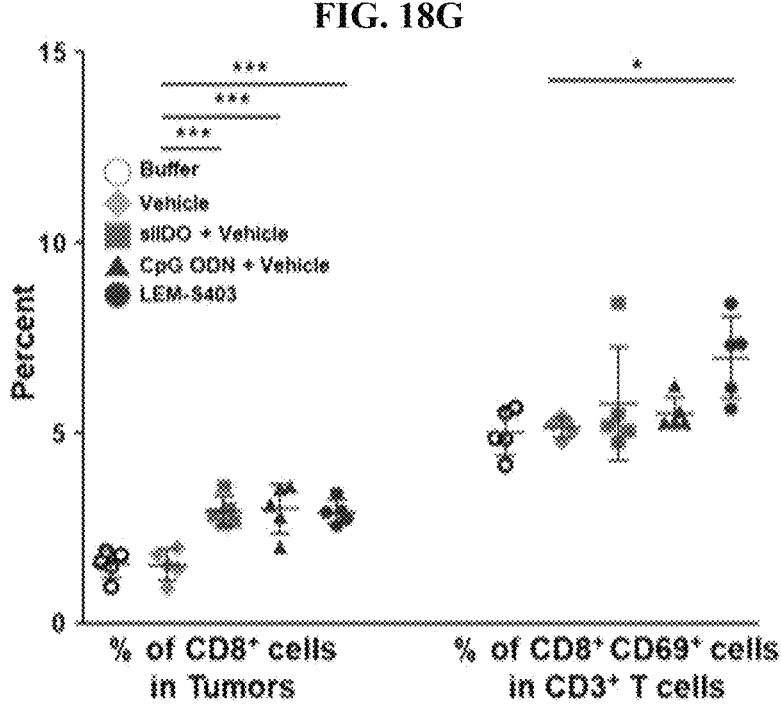
Figure 18H:
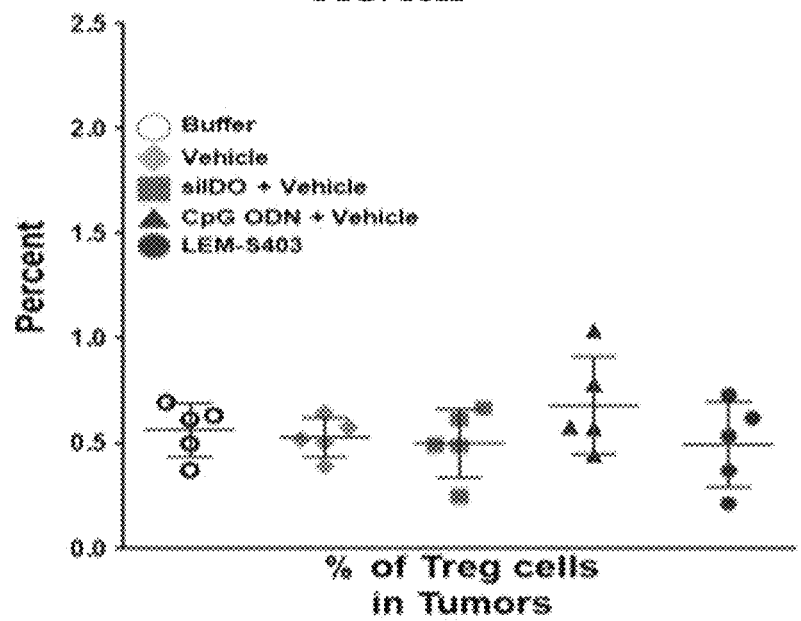

Thereafter, surface modification was conducted by the method in Example 2-(1) using 2 mL of APTES. As a result, DegradaBALL was obtained as shown in FIG. 13A.

2. siDO Selection and Knock-Down Efficiency

State, USA). Ficoll-paque was purchased from GE Healthcare Bio Sciences AB (Uppsala, Sweden). TAMRA NHS ester was purchased from Thermo Fisher Scientific (Massachusetts, USA). 10× phosphate buffered saline (10×PBS),

TABLE 2

|   | Target | Target site | Sense | Antisense | Knockdown Efficiency (%) |
|---|---|---|---|---|---|
| #1 | IOD1 | ATCACCATGG CATATGTGTG G (SEQ ID NO: 40) | AUCACCAUGG CAUAUGUGU G (SEQ ID NO: 1) | CACACAUAUG CCAUGGUGAU (SEQ ID NO: 2) | 28.78 |
| #2 |  | TGACTTATGA GAACATGGAC (SEQ ID NO: 41) | UGACUUAUG AGAACAUGG AC (SEQ ID NO: 3) | GUCCAUGUUC UCAUAAGUCA (SEQ ID NO: 4) | 54.81 |
| #3 |  | TGGAGACTGC AGTAAAGGAT (SEQ ID NO: 42) | UGGAGACUGC AGUAAAGGA U (SEQ ID NO: 5) | AUCCUUUACU GCAGUCUCCA (SEQ ID NO: 6) | 96.43 |
| #4 |  | AGCTGCTTCT GCAATCAAAG (SEQ ID NO: 43) | AGCUGCUUCU GCAAUCAAAG (SEQ ID NO: 7) | CUUUGAU UGCAGAAGCA GCU (SEQ ID NO: 8) | 99.45 |
| #4' |  | AGCTGCTTCT GCAATCAAAG TAAT (SEQ ID NO: 44) | AGCUGCUUCU GCAAUCAAAG UAAU (SEQ ID NO: 11) | AUUACUUUG AUUGCAGAA GCAGCU (SEQ ID NO: 12) | 100.22 |
| #5 |  | TGATTCCTGC AAGCCAGCA (SEQ ID NO: 45) | UGAUUCCUGC AAGCCAGCA (SEQ ID NO: 9) | UGCUGGCUUG CAGGAAUCA (SEQ ID NO: 10) | 83.24 |
| #6 | IDO1/ IDO2 | TCACCATGC ATATGTGTGG (SEQ ID NO: 46) | UCACCAUGGC AUAUGUGUG G (SEQ ID NO: 16) | CCACACAUAU GCCAUGGUGA (SEQ ID NO: 17) | 0 |
| #7 |  | TCTCATTTCGT GATGGAGA (SEQ ID NO: 47) | UCUCAUUUCG UGAUGGAGA (SEQ ID NO: 18) | UCUCCAUCAC GAAAUGAGA (SEQ ID NO: 19) | 0 |
| #8 |  | TCTGGCTGGA AAGGCAACC (SEQ ID NO: 48) | UCUGGCUGGA AAGGCAACC (SEQ ID NO: 20) | GGUUGCCUUU CCAGCCAGA (SEQ ID NO: 21) | 0 |
| #9 |  | GGTCTGGTGT ATGAAGG (SEQ ID NO: 49) | GGUCUGGUG UAUGAAGG (SEQ ID NO: 22) | CCUUCAUACA CCAGACC (SEQ ID NO: 23) | 35.13 |

Figure 19:
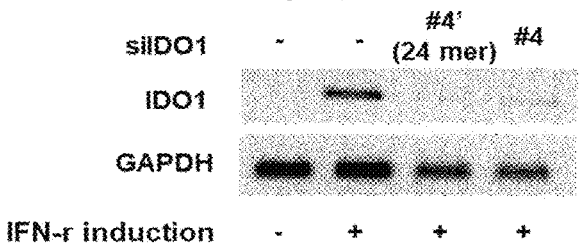
FIG. 19 illustrates IFN γ-induction effects of siRNA (#4) of SEQ ID NOs: 7 and 8 and siRNA with extension of 4 mer (#4', total 24 mer).
Figure 20:
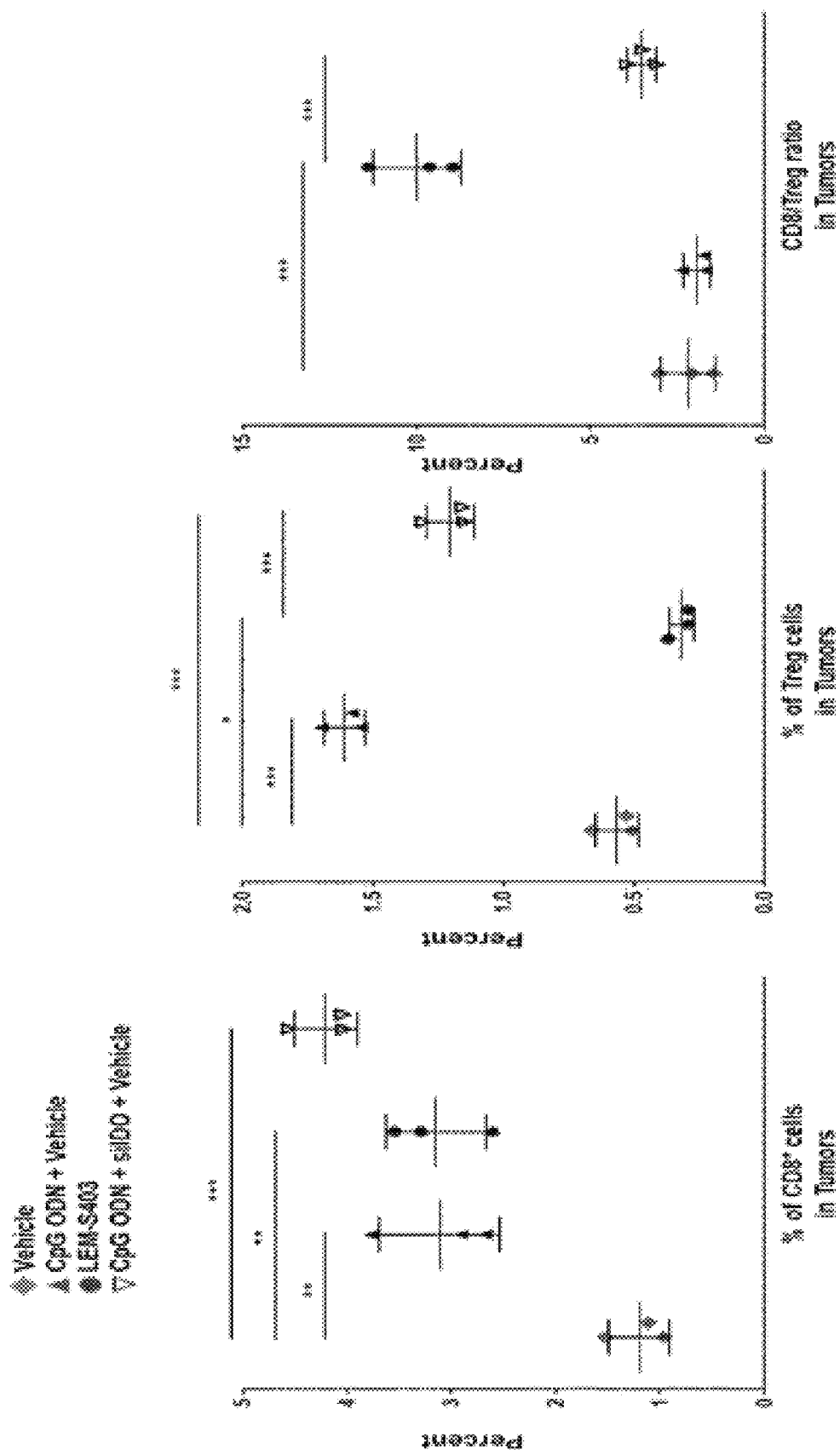
FIG. 20 shows ratios of CD8 cell and Treg cell in tumor. Specifically, a difference when a combination of LEM-S403 and CpG ODN+siIDO is used for treatment is illustrated, and importance of a carbon linker to connect CpG ODN and siIDO is demonstrated.
Figure 21:
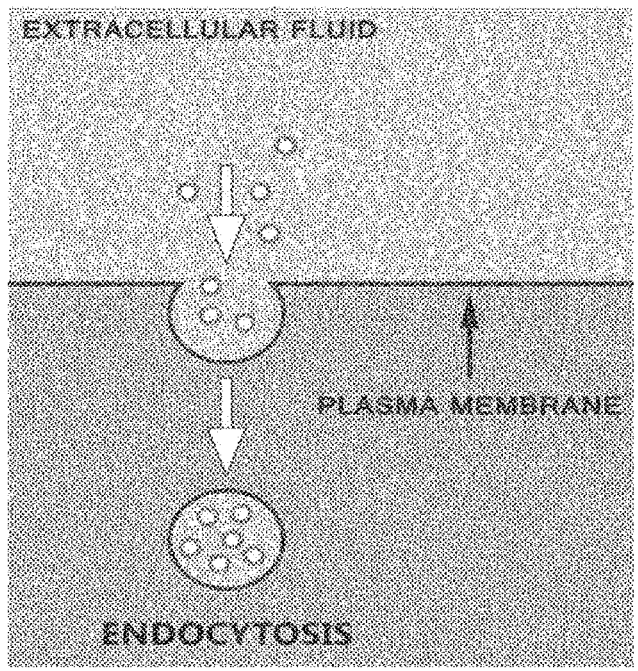
FIG. 21 is a schematic view of the delivery of particles into cells according to an embodiment.
Figure 22:
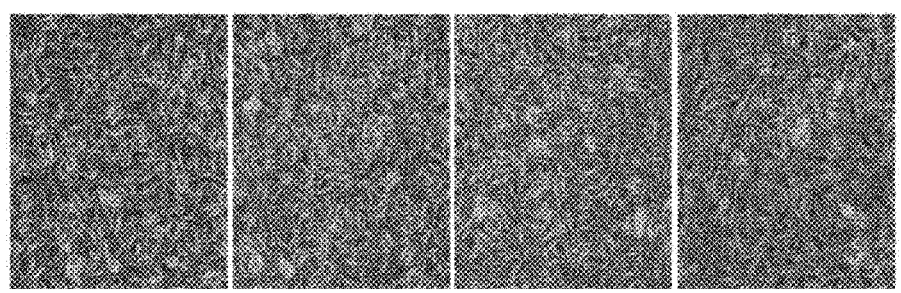
FIG. 22 illustrates confirmation of whether smooth introduction of particles into cells (B16F10) when a content ratio between the porous silica particles according to an embodiment of the present invention and nucleic acid molecules is differently adjusted.

For stability of siRNA of SEQ ID NOs: 7 and 8, the experiment was conducted with further extension of 4 mer. Even in the sequences of SEQ ID NOs: 11 and 12 including further extension of 4 mer, excellent K/D effects were observed (FIG. 19), therefore, the sequences of SEQ ID NOs: 11 and 12 were selected as siIDO in the present experiment.

3. CpG-ODN Selection

Figure 25:
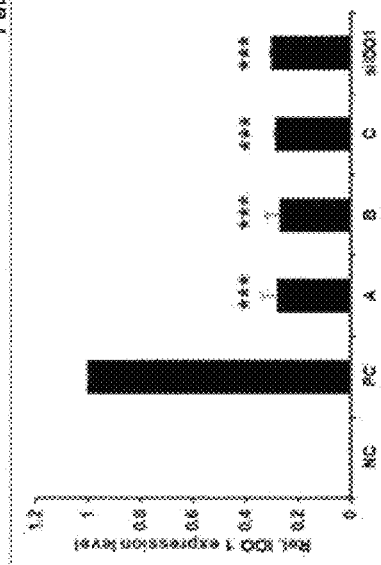
FIG. 25 illustrates IDO1 expression levels when CpG class A, B or C is coupled.

The selected siIDO 1(#4, #4') was connected with different classes of CpG (A, B, C), respectively, in order to determine effects thereof. Each test was conducted by loading the above material in DegradaBALL Independent of CpG class, it was confirmed that all of the above classes were K/O by siIDO1 (FIG. 25).

Figure 26:
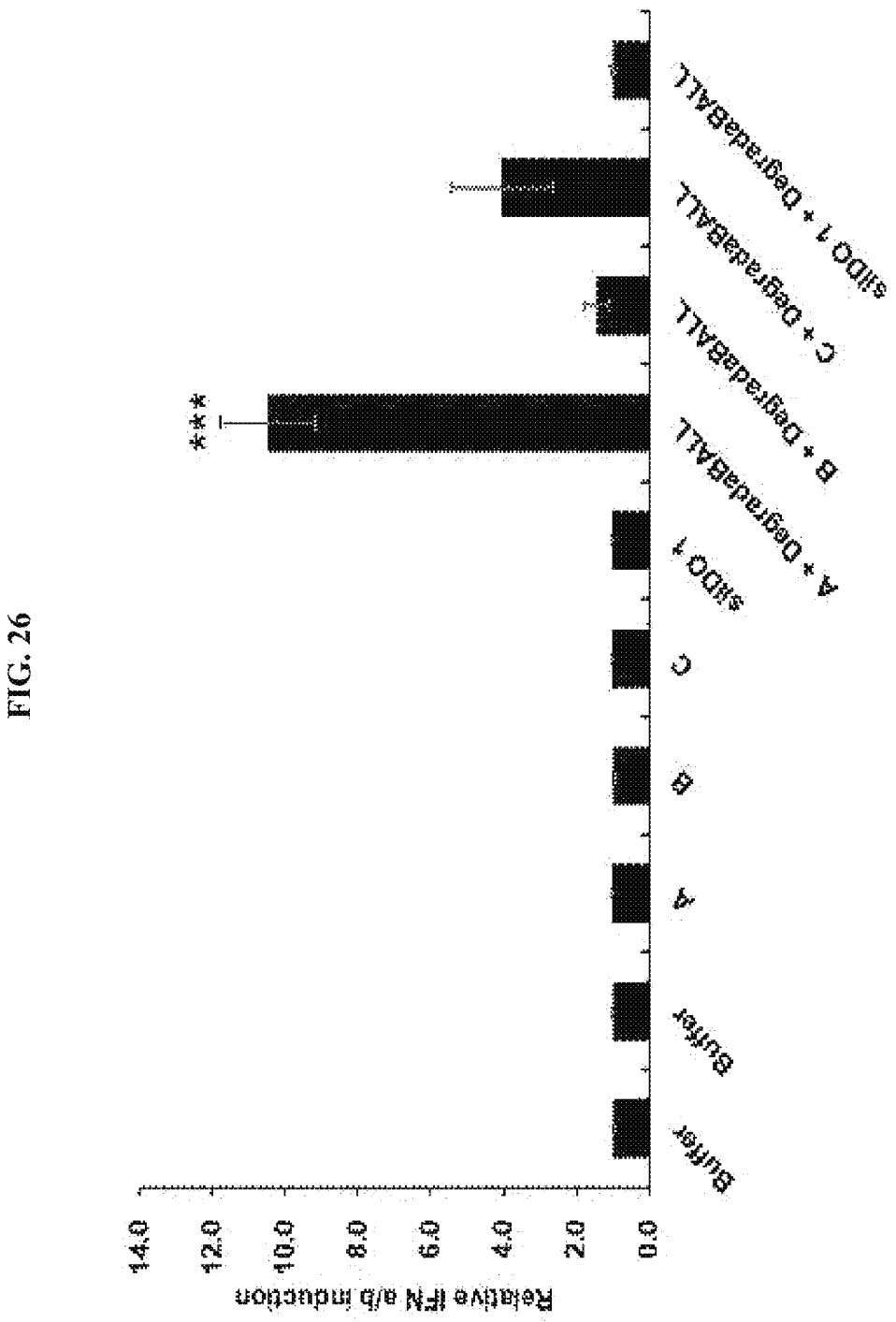
FIG. 26 illustrates Type 1 IFN induction effects according to CpG class.

As a result of the experiment, it was confirmed that siIDO1 connected to CpG class A has more excellent Type IFN induction effects, as compared to siIDO1 connected to class B or C (FIG. 26).

Accordingly, CpG-ODN class A was selected as CpG-ODN of the present experiment.

Example 3: Preparation of LEM-S403 Including CpG-ODN-siIDO Loaded in DegradaBALL 1. Material for Loading CpG-ODN-siIDO DegradaBALL used herein is the particles in Example 2-1. Ethanol was purchased from Sigma-Aldrich (Missouri Ham's F-12K medium (F-12K), Minimum Essential Medium (MEM), Roswell Park Memorial Institute 1640 (RPMI 1640), fetal bovine serum (FBS), bovine calf serum (BCS), penicillin-streptomycin and trypsin-EDTA were purchased from WelGene (Seoul, Korea). Anti-mouse PD-1 and CTLA-4 antibodies were purchased from Bio X Cell (NH, USA). Human and mouse CpG-ODN, siIDO, CpG-ODN-siIDO, FITC-conjugated CpG-ODN-siIDO, Cy5-conjugated CpG-ODN-siIDO and PCR primers were synthesized by Bioneer, Inc (Daejeon, Korea). Sequence information of PCR primer is shown in Table 3. Flow cytometry antibodies (Alexa Fluor® 647 anti-mouse CD11c, Alexa Fluor® R-PE anti-Ly6C, Alexa Fluor® 647 anti-mouse FOXP3, Alexa Fluor® 488 anti-mouse NK-1.1, PE/Cy7 anti-mouse CD4, APC anti-mouse CD3, FITC and Alexa Fluor® 488 anti-mouse CD8a, PE anti-mouse CD122, PE anti-mouse CD25, Alexa Fluor® 647 anti-mouse CD69 and Alexa Fluor® 647 anti-mouse CD86) were purchased from Biolegend (CA, USA). Anti-rabbit p-STAT-1 antibody was purchased from CST (MA, USA), and FITC anti-mouse IDO1 antibody was purchased from Santa Cruz biotechnology (CA, USA). Anti-rabbit L-Kynurenine antibody was purchased from ImmunSmol (CA, USA). TUNEL analysis kit was purchased from Promega (WA, USA). Lipofectamine® 2000, TRIzol and Power SYBR® Green PCR Master Mix were purchased from Thermo Fisher Scientific (MA, USA). Recombinant human interferon-gamma (IFN-γ) was purchased from Peprotech Inc. (NJ, USA). HEK-Blue™ IFN-α/β Cell was purchased from Invivogen (CA, USA). Nucleotide sequence information of PCR primer is shown in Table 3.

TABLE 3

Primer sequence

| Specie | Target gene | | Sequence | SEQ ID NO: |
|---|---|---|---|---|
| Human | IDO1 | Forward | 5'-GAT CCT AAT AAC CCC CTG ACT-3' | 24 |
| | | Reverse | 5'-CAG CAT CTG CTC CAC CAG-3' | 25 |
| | GAPDH | Forward | 5'-TCA CTG CCA CCC AGA CTG-3' | 26 |
| | | Reverse | 5'-GGA TCA CCT TGC CCA CAG C-3' | 27 |
| Mouse | IDO1 | Forward | 5'-AGC TGC CCG ACG CAT ACA GCC CC-3' | 28 |
| | | Reverse | 5'-ACC CCA GGG CCA GGT GTG CCA-3' | 29 |
| | GAPDH | Forward | 5'-TGG ATT TGG ACG CAT TGG TC-3' | 30 |
| | | Reverse | 5'-TTT GCA CTG GTA CGT GTT GAT-3' | 31 |

2. Features of DegradaBALL Used for Production of LEM-S403

TEM image of DegradaBALL was obtained from LIBRA 120 EF-TEM (Carl Zeiss, Germany). Zeta potential and hydrodynamic size of DegradaBALL were measured by Zetasizer NanoS (Malvern Instruments, UK). A nitrogen adsorption isothermal graph was measured by NOVA adsorption device. The surface area of DegradaBALL was calibrated by Brunauer-Emmett-Teller method.

3. LEM-S403 Loading Capacity

In order to determine a loading capacity, DegradaBALL (1, 2, 3, 4, 5, 7 and 10 μg) with different concentration was mixed with 1 μg of human CpG-ODN-siIDO in 10 μL 1×PBS solution. After culturing the solution at room temperature for 30 minutes, the mixture was centrifuged at 8,000 rpm for 10 minutes. Then, the supernatant was moved to a new micro-tube while measuring a concentration of the CpG-ODN-siIDO residue by Citation 5 (Biotech, VT, USA). An amount of the CpG-ODN-siIDO residue in the supernatant was determined by measuring absorbance at 260 nm. A loading capacity was calculated based on the amount of CpG-ODN-siIDO residue in the supernatant.

A dosage of LEM-S403 indicates a content of CpG-ODN-siIDO in LEM-S403. LEM-S403 is CpG-ODN-siIDO prepared in DegradaBALL in a weight ratio of 1:5 (CpG-ODN-siIDO:DegradaBALL).

4. LEM-S403 Release Profiling

For release profiling of LEM-S403,

LEM-S403 (100 ug/mL, volume=100 uL) was diffused in a bio-similar solution (SBF, pH 7.4, [Na+]=142 mM, [K+]=5 mM, [Mg2+]=1.5 mM, [Ca2+]=2.5 mM, [Cl—]=148.8 mM, [HCO3-]=4.2 mM and [HPO42-]=1.0 mM (pH 7.4 Tris buffer ([Tris]=50 mM))) at 37° C. for 10 days. At predetermined time points (days 1, 2, 3, 4, 7 and 10), the mixture was centrifuged at 8,000 rpm for 10 minutes to pull down LEM-S403 while replacing the supernatant with a fresh SBF. An amount of released CpG-ODN-siIDO was measured based on the absorbance at 260 nm.

5. Cell Culture

All cells were cultured in a CO2 incubator at 37° C. under a condition of 5% CO2 (SANYO Electric, Osaka, Japan). A549 cells were cultured in F-12K medium containing 10% FBS (v/v) and 10 unit/mL of penicillin/streptomycin. CT26 cells were cultured in RPMI-1640 medium containing 10% FBS (v/v) and 10 unit/mL of penicillin/streptomycin. Human peripheral blood monocytes (PBMCs) were purchased from Lonza (Basel, Switzerland). Mouse PBMC were isolated from five (5)-week old Balb/c mice under $Ca^{2+}$ and $Mg^{2+}$-free conditions according to ficoll gradient protocol.

6. Cell Absorption Efficiency Test of LEM-S403 in Mouse PBMC

The mouse PMBC was seeded with a density of $2.5×10^4$ cells/well in 24-well plate. Then, a buffer with or without DegradaBALL or FITC-conjugated CpG-ODN-siIDO (100 nM) were added to each well. After culturing for 6 hours, the cells were washed with 1×PBS and then collected for staining. The cells were suspended in a culture buffer (0.5% BSA in 1×PBS) at room temperature for 10 minutes. After blocking, the cells were centrifuged at 1,250 rpm for 2 minutes, followed by removing the supernatant. Thereafter, the cells were treated with a primary antibody solution (0.5% BSA in 1×PBS) (1:200 dilution) and cultured at room temperature for 1 hour. The cells were centrifuged and washed with an incubation buffer. The washed cells were resuspended in 200 μL of culture buffer and analyzed using Attune NxT flow cytometer (Thermo Fisher, MA, USA).

7. IDO1 Knock-Down Efficiency Test in A549 Cell

A549 cells were seeded with a density of $5×10^4$ cells/well in 24-well plate. After culturing for 24 hours, the cells were washed with 1×PBS. Then, DegradaBALL, CpG-ODN-siIDO (150 nM), siIDO (150 nM), CpG-ODN (150 nM), CpG-ODN-siIDO with DegradaBALL (10, 50 and 150 nM), siIDO with DegradaBALL (150 nM) or CpG-ODN with DegradaBALL (150 nM) was dispersed in 500 μL of F-12K medium (non-serum), followed by adding the same to each well. DegradaBALL and loaded material were prepared with a relative ratio of 5:1 (w/w). After culturing for 6 hours, the cells were washed with 1×PBS, followed by additional culture in a fresh growth medium containing IFN-γ (80 ng/mL) for a predetermined time. IDO1 inhibition was detected by Real Time qPCR.

In order to investigate a duration of knock-down efficiency, A549 cells were seeded with a density of $5×10^4$ cells/well in 24-well plate. After culturing for 24 hours, the cells were washed with 1×PBS. Thereafter, CpG-ODN-siIDO (150 nM) loaded in DegradaBALL or CpG-ODN-siIDO loaded in Lipofectamine was dispersed in 500 μL of F-12K medium (non-serum) and added to each well. After culturing for 6 hours, the cells were washed with 1×PBS, followed by additional culture in a new growth medium containing IFN-γ (80 ng/mL) for a predetermined time. IDO1 inhibition was detected by Real Time qPCR.

8. Induction of Type 1 IFN Secretion

Human PBMC was seeded along with 50 μL MEM medium in 96-well plate (5×10$^5$ cells/well). After culturing for 2 hours, buffer, siIDO (125 nM), CpG-ODN (125 nM) or CpG-ODN-siIDO (125 nM) was dispersed in 50 μL of MEM medium with or without DegradaBALL and then added to each well. The cells were further cultured for 22 hours. Type 1 IFN contained in the medium was determined by a reporter cell system (HEK-Blue™ IFN-α/β cell) according to a protocol of the manufacturer.

The human PBMC was seeded along with 50 μL MEM medium in 96-well plate (5×10$^5$ cells/well). After culturing for 2 hours, each of 500, 250, 125, 62.5, 31.25, 15.63 and 7.81 nM of LEM-S403 dispersed in 50 μL MEM medium was added to each well. The cells were further cultured for 22 hours. Type 1 IFN in the medium was determined by a reporter cell system (HEK-Blue™ IFN-α/β cell) according to a protocol of the manufacturer.

9. Animal Experiment

All animal experiments proceeded according to the Institutional Animal Care and Use Committee (IACUC) of Seoul National University. Balb/c male mice (5-week old) were purchased from ORIENT BIO (Seongnam, Korea). During an experimental period, the animals were kept under environmental conditions of a temperature of 19 to 25° C., a humidity of 40 to 70% and a cycle of light-12 hours and dark-12 hours.

10. Sustainability of LEM-S403 after Intratumoral Injection

Mice with tumor (Balb/c) were prepared by subcutaneous injection of CT26 cells (1×10$^6$ cells) in 100 μL of sterile 1×PBS solution containing Matrigel. When a volume of the tumor reaches about 200 mm$^3$, the mouse was treated with buffer, TAMRA-conjugated DegradaBALL or Cy5-conjugated CpG-siIDO with or without TAMRA-conjugated DegradaBALL through intratumoral injection. On day 1 or 3 after injection, the tumor was excised for analysis. A fluorescent image of whole tumor was obtained by FOBI in vivo imaging system (NeoScience, Seoul, Korea). The tumor was cultured in 4% PFA solution. After sucrose penetration, the sample was put an optimal cutting temperature (OCT) compound and then fragmented with a thickness of 10 μm. A section slide was washed with sterile water, followed by staining using DAPI. The sample was observed by BX71 microscope having a 10× object lens.

For flow cytometry, when the volume of tumor reached about 200 mm$^3$, FITC-conjugated CpG-siIDO was injected into a tumor of a mouse having the tumor (CT26) along with or without DegradaBALL. On day 1 or 3 after injection, the tumor was collected. The collected tumor was sliced thinly and cultured in 1 mL of collagenase solution at 37° C. for 30 minutes. The cells were collected using a cell strainer, followed by flow cytometry.

11. Therapeutic Efficacy of LEM-S403 Single Therapy and Combination Therapy Using Immune Checkpoint Inhibitor CT26 cells (1×10$^6$ cells) in 100 μL of sterile 1×PBS solution containing matrigel were subcutaneously injected into the right or both ribs of a Balb/c mouse. A buffer, vehicle (DegradaBALL 70 μg), CpG-ODN (4.5 μg)+vehicle (DegradaBALL 22.5 μg), siIDO (9.5 μg)+vehicle (DegradaBALL 47.5 μg) or LEMIDO (3.5, 7 and 14 μg) was injected into the right rib on day 0, 3, 7 and 10 after the tumor volume reached about 100 mm$^3$. The tumor volume was measured three times every week. A survival rate was proposed by Kaplan-Meier plot.

According to the above method, mice with tumor (CT26) were prepared. A buffer, vehicle (DegradaBALL 70 μg), anti-PD-1 ab (aPD-1; 10 mg/kg), anti-CTLA-4 ab (aCTLA-4; 10 mg/kg), LEMIDO (14 μg), LEMIDO+aPD-1 ab or LEMIDO+aCTLA-4 ab was injected on day 0, 3, 7 and 10 after the tumor volume reached about 100 mm$^3$. The buffer, vehicle and LEMIDO, respectively, were intratumorally injected into the right rib, while aPD-1 and aCTLA-4 were intraperitoneally injected. The tumor volume was measured three times every week. A survival rate was proposed by Kaplan-Meier plot.

12. Treatment Mechanism of LEM-S403 Single Therapy

According to the above method, mice with tumor (CT26) were prepared. A buffer, vehicle (DegradaBALL 70 μg), CpG-ODN (4.5 μg)+vehicle (DegradaBALL 22.5 μg), siIDO (9.5 μg)+vehicle (DegradaBALL 47.5 μg) or LEMIDO (14 μg) was intratumorally injected into the right rib on day 0 and 3 after the tumor volume reached about 100 mm$^3$. On day 4, each mouse was sacrificed while tumors with injection or tumors apart far from one another were extracted for further analysis. During sacrifice, whole blood of the mouse was collected using a tube treated with EDTA. The collected blood was subjected to analysis using Hemavet 950.

13. Annexin V

The collected tumor was sliced thinly and cultured in 1 mL of collagenase solution at 37° C. for 30 minutes. The cells were collected by a cell strainer. Annexin V and propidium iodide staining were performed along with PI (Biolegend, CA, USA) using FITC Annexin V Apoptosis Detection Kit according to a protocol of the manufacturer.

14. Reverse Transcriptase PCR (RT-PCR)

From cells or tumor collected based on combined GITC-column, total RNA was extracted. Synthesis of cDNA was performed under the following conditions: a cycle of 65° C. for 5 minutes, 42° C. for 2 minutes, 42° C. for 50 minutes and 70° C. for 15 minutes under inactivation condition. For gel delay, amplification of cDNA was conducted under the following conditions: 30 cycles of 95° C. for 30 seconds, 55° C. for 60 seconds and 72° C. for 30 seconds under desired condition. The product was delayed in 2% TAE agarose gel by electrophoresis, followed by visualization using Gel-DOC XR+system (Bio-rad, CA, USA). qPCR was performed using CFX96 Touch Real-Time PCR Detection System (Bio-rad) and Power SYBR® Green PCR Master Mix according to a protocol of the manufacturer.

15. Histological Assessment and Fluorescence Staining

The extracted tumor was cultured in 4% PFA solution. After sucrose penetration, the organs entered OCT compound and then were fragmented with a thickness of 10 μm. The fragmented tissues were stained using H & E staining reagent (BBC Biochemical, Mt Vernon, Wash., USA).

For immunofluorescence staining, blocking was conducted for 45 minutes using PBS containing 5% normal goat serum, and then, tissue fragments were stained with a fluorescent dye-combined antibody or a primary antibody followed by a fluorescent dye-combined secondary antibody. A nucleus was stained with DAPI. Each stained tissue fragment was observed with BX71 microscope having a 10× object lens.

16. Flow Cytometry

For tumor tissues, the extracted tumor was cultured in 1 mL of collagenase solution at 37° C. for 30 minutes, followed by collecting cells using a cell strainer. Primary cells (1×10⁵ cells) were cultured in 4% PFA at 37° C. for 10 minutes and then washed with a culture buffer. The cells were suspended in a culture buffer (0.5% BSA in 1×PBS) at room temperature for 10 minutes. After blocking, the cells were centrifuged at 1,250 rpm for 2 minutes, followed by removing the supernatant. Then, the cells were treated with a primary antibody solution (0.5% BAS in 1×PBS, 1:200 dilution), and cultured at room temperature for 1 hour. The cells were centrifuged and washed with an incubation buffer. The washed cells were resuspended in 200 μL of incubation buffer, followed by analysis using Attune NxT flow cytometer (Thermo Fisher, MA, USA).

17. Synergy Effect of Combined cpGODN and siIDO Carbon Linker

In order to confirm whether LEM-S403 in the combined form has synergy effects, comparison experiments were conducted. The mice were treated with vehicle, CpGODN+vehicle, LEM-S403 or cocktail (CpGODN+siIDO+vehicle), respectively, on day 0 and day 3. On day 4, the tumor was extracted and analyzed by flow cytometry. The cocktail therapy group showed an increase of CD8+T cells similar to CpG-ODN and LEM-S403 groups. However, unlike LEM-S403, the Treg cell group was not reduced. Due to this difference, CD8/Teg ratio in the tumor was superior over the above group. This result demonstrates that a strategy to combine siIDO and CpG-ODN is necessary for advantages of treatment.

18. Treatment Mechanism of LEM-S403 and Cocktail Therapy Using CpG-ODN and siIDO Tumor in a mouse (CT26) was prepared according to the above-described method. When a volume of the tumor reached about 100 mm³, vehicle (70 μg of DegradaBALL), CpG-ODN (4.5 μg)+vehicle (22.5 μg of DegradaBALL), LEM-S403 (14 μg) or CpG-ODN (4.5 μg)+siIDO (9.5 μg)+vehicle (70 μg of DegradaBALL) was injected into a tumor in the right rib on day 0 and day 3. On day 4, the mouse was sacrificed and the tumor under injection was extracted for measurement of flow cells.

A sequence listing electronically submitted with the present application on Nov. 23, 2021 as an ASCII text file named 20211123_Q62921LC32_TU_SEQ, created on Oct. 8, 2021 and having a size of 13,000 bytes, is incorporated herein by reference in its entirety.

What is claimed is:

1. A nucleic acid carrier comprising:
a CpG oligodeoxynucleotide-RNA (CpG-ODN-RNA) conjugate; and
a porous silica particle carrying the CpG-ODN-RNA conjugate inside pores thereof, the porous silica particle having an average pore diameter of 7 to 30 nm,
wherein the RNA is indoleamine 2,3-dioxygenase (IDO) siRNA; and
the IDO siRNA is a single pair of nucleotide sequences, and the IDO siRNA is selected from the group consisting of:
(a) an siRNA comprising SEQ ID NOs: 1 and 2;
(b) an siRNA comprising SEQ ID NOs: 3 and 4;
(c) an siRNA comprising SEQ ID NOs: 5 and 6;
(d) an siRNA comprising SEQ ID NOs: 7 and 8; and
(e) an siRNA comprising SEQ ID NOs: 9 and 10.

2. The nucleic acid carrier according to claim 1, wherein the CpG-ODN and the RNA of the CpG-ODN-RNA conjugate are coupled through a linker.

3. The nucleic acid carrier according to claim 2, wherein the linker is at least one selected from the group consisting of a saturated alkyl chain (C3 to C18), a triazole linker, and 4-methyl-6,7,8,9,10,10a-hexahydro-5H-3λ2-cycloocta[d]pyridazine linker.

4. The nucleic acid carrier according to claim 1, wherein the siRNA further comprises a sequence of 1 to 10 nt complementary to IDO mRNA at a 5'-end or a 3'-end.

5. The nucleic acid carrier according to claim 1, wherein the CpG-ODN is CpG-A ODN, CpG-B ODN or CpG-C ODN.

6. The nucleic acid carrier according to claim 1, wherein the porous silica particle is positively charged inside the pores.

7. The nucleic acid carrier according to claim 1, wherein the porous silica particle has zeta potential of 5 to 80 mV before loading of the conjugate.

8. The nucleic acid carrier according to claim 1, wherein a weight ratio of the conjugate and the particle ranges from 1:1 to 1:20.

9. The nucleic acid carrier according to claim 1, wherein a BET surface area of the particle ranges from 200 to 700 $m^2/g$, and a particle diameter ranges from 50 to 1000 nm.

10. A method for treatment of cancer, the method comprising administering the nucleic acid carrier of claim 1 to a subject in need thereof.

11. The method according to claim 10, wherein the cancer is selected from ovarian cancer, cervical cancer, follicle cysts, gynecologic cancer, urologic cancer, renal cancer, testicular cancer, penile cancer, genitourinary tract cancer, testicular tumor, bladder cancer, skin cancer, sarcoma, osteosarcoma, malignant bone tumor, soft tissue sarcoma, keratoacanthoma, melanoma, lung cancer, small cell lung carcinoma, non-small cell lung carcinoma (NSCLC), lung adenocarcinoma, squamous cell carcinoma of the lung, papillary cancer, breast cancer, triple negative breast cancer (TNBC), breast endocrine cancer, hepatobiliary and pancreatic cancer, liver cancer, cholangiocarcinoma, gallbladder cancer, bile duct cancer, pancreatic cancer, bone cancer, bone marrow disorder, lymphatic disorder, hair cell cancer, oral and pharyngeal (oral) cancer, lip cancer, tongue cancer, oral cancer, salivary gland cancer, pharyngeal cancer, laryngeal cancer, esophageal cancer, gastric cancer, gastrointestinal cancer, small intestine cancer, colon cancer, rectal cancer, prostate cancer, vulvar cancer, thyroid cancer, large intestine cancer, endometrial cancer, uterine cancer, brain cancer, glioma, non-glioma tumor, malignant glioma, metastatic brain cancer, brain parenchyma, vestibular schwannoma, pituitary tumor, head and neck cancer, central nervous system cancer, peritoneal cancer, hepatocellular carcinoma, head cancer, neck cancer, primary tumor, metastatic tumor, lymphoma, squamous cell carcinoma, hematologic malignancy, endocrine cancer, Hodgkin disease or leukemia.

12. The nucleic acid carrier according to claim 1, wherein the porous silica particle has zeta potential of 40 to 55 mV before loading of the conjugate.

13. A nucleic acid carrier comprising:
a CpG oligodeoxynucleotide-RNA (CpG-ODN-RNA) conjugate; and
a porous silica particle carrying the CpG-ODN-RNA conjugate inside pores thereof, the porous silica particle having an average pore diameter of 7 to 30 nm,
wherein the RNA is indoleamine 2,3-dioxygenase (IDO) siRNA; and
the IDO siRNA comprises siRNA of SEQ ID NOs: 11 and 12.

14. The nucleic acid carrier according to claim 13, wherein the porous silica particle has zeta potential of 40 to 55 mV before loading of the conjugate.

15. The nucleic acid carrier according to claim 13, wherein a weight ratio of the conjugate and the particle ranges from 1:1 to 1:20.

16. A nucleic acid carrier comprising:
a CpG oligodeoxynucleotide-RNA (CpG-ODN-RNA) conjugate; and
a porous silica particle carrying the CpG-ODN-RNA conjugate inside pores thereof, the porous silica particle having an average pore diameter of 7 to 30 nm,
wherein the CpG-ODN comprises any one nucleotide among SEQ ID NOs: 13 to 15.

* * * * *

SEQUENCE LISTING

<160> NUMBER OF SEQ ID NOS: 52

<210> SEQ ID NO 1
<211> LENGTH: 20
<212> TYPE: RNA
<213> ORGANISM: Artificial Sequence
<220> FEATURE:
<223> OTHER INFORMATION: siRNA

<400> SEQUENCE: 1
aucaccaugg cauaugugug            20

<210> SEQ ID NO 2
<211> LENGTH: 20
<212> TYPE: RNA
<213> ORGANISM: Artificial Sequence
<220> FEATURE:
<223> OTHER INFORMATION: siRNA

<400> SEQUENCE: 2
cacacauaug ccauggugau            20

<210> SEQ ID NO 3
<211> LENGTH: 20
<212> TYPE: RNA
<213> ORGANISM: Artificial Sequence
<220> FEATURE:
<223> OTHER INFORMATION: siRNA

<400> SEQUENCE: 3
ugacuuauga gaacauggac            20

<210> SEQ ID NO 4
<211> LENGTH: 20
<212> TYPE: RNA
<213> ORGANISM: Artificial Sequence
<220> FEATURE:
<223> OTHER INFORMATION: siRNA

<400> SEQUENCE: 4
guccauguuc ucauaaguca            20

```
<210> SEQ ID NO 5
<211> LENGTH: 20
<212> TYPE: RNA
<213> ORGANISM: Artificial Sequence
<220> FEATURE:
<223> OTHER INFORMATION: siRNA

<400> SEQUENCE: 5
uggagacugc aguaaaggau                                                    20

<210> SEQ ID NO 6
<211> LENGTH: 20
<212> TYPE: RNA
<213> ORGANISM: Artificial Sequence
<220> FEATURE:
<223> OTHER INFORMATION: siRNA

<400> SEQUENCE: 6
auccuuuacu gcagucucca                                                    20

<210> SEQ ID NO 7
<211> LENGTH: 20
<212> TYPE: RNA
<213> ORGANISM: Artificial Sequence
<220> FEATURE:
<223> OTHER INFORMATION: siRNA

<400> SEQUENCE: 7
agcugcuucu gcaaucaaag                                                    20

<210> SEQ ID NO 8
<211> LENGTH: 20
<212> TYPE: RNA
<213> ORGANISM: Artificial Sequence
<220> FEATURE:
<223> OTHER INFORMATION: siRNA

<400> SEQUENCE: 8
cuuugauugc agaagcagcu                                                    20

<210> SEQ ID NO 9
<211> LENGTH: 19
<212> TYPE: RNA
<213> ORGANISM: Artificial Sequence
<220> FEATURE:
<223> OTHER INFORMATION: siRNA

<400> SEQUENCE: 9 ugauccugc aagccagca                                                      19

<210> SEQ ID NO 10
<211> LENGTH: 19
<212> TYPE: RNA
<213> ORGANISM: Artificial Sequence
<220> FEATURE:
<223> OTHER INFORMATION: siRNA

<400> SEQUENCE: 10
ugcuggcuug caggaauca                                                     19

<210> SEQ ID NO 11
<211> LENGTH: 24
<212> TYPE: RNA
<213> ORGANISM: Artificial Sequence
<220> FEATURE:
<223> OTHER INFORMATION: siRNA
```

<400> SEQUENCE: 11
agcugcuucu gcaaucaaag uaau                                          24

<210> SEQ ID NO 12
<211> LENGTH: 24
<212> TYPE: RNA
<213> ORGANISM: Artificial Sequence
<220> FEATURE:
<223> OTHER INFORMATION: siRNA

<400> SEQUENCE: 12
auuacuuuga uugcagaagc agcu                                          24

<210> SEQ ID NO 13
<211> LENGTH: 20
<212> TYPE: DNA
<213> ORGANISM: Artificial Sequence
<220> FEATURE:
<223> OTHER INFORMATION: CpG ODN

<400> SEQUENCE: 13
gggggacgat cgtcggggg                                                20

<210> SEQ ID NO 14
<211> LENGTH: 24
<212> TYPE: DNA
<213> ORGANISM: Artificial Sequence
<220> FEATURE:
<223> OTHER INFORMATION: CpG ODN

<400> SEQUENCE: 14
tcgtcgtttt gtcgttttgt cgtt                                          24

<210> SEQ ID NO 15
<211> LENGTH: 22
<212> TYPE: DNA
<213> ORGANISM: Artificial Sequence
<220> FEATURE:
<223> OTHER INFORMATION: CpG ODN

<400> SEQUENCE: 15
tcgtcgtttt cggcgcgcgc cg                                            22

<210> SEQ ID NO 16
<211> LENGTH: 20
<212> TYPE: RNA
<213> ORGANISM: Artificial Sequence
<220> FEATURE:
<223> OTHER INFORMATION: siRNA

<400> SEQUENCE: 16
ucaccauggc auaugugugg                                               20

<210> SEQ ID NO 17
<211> LENGTH: 20
<212> TYPE: RNA
<213> ORGANISM: Artificial Sequence
<220> FEATURE:
<223> OTHER INFORMATION: siRNA

<400> SEQUENCE: 17
ccacacauau gccaugguga                                               20

<210> SEQ ID NO 18
<211> LENGTH: 19

```
<212> TYPE: RNA
<213> ORGANISM: Artificial Sequence
<220> FEATURE:
<223> OTHER INFORMATION: siRNA

<400> SEQUENCE: 18
ucucauuucg ugauggaga                                                    19

<210> SEQ ID NO 19
<211> LENGTH: 19
<212> TYPE: RNA
<213> ORGANISM: Artificial Sequence
<220> FEATURE:
<223> OTHER INFORMATION: siRNA

<400> SEQUENCE: 19
ucuccaucac gaaaugaga                                                    19

<210> SEQ ID NO 20
<211> LENGTH: 19
<212> TYPE: RNA
<213> ORGANISM: Artificial Sequence
<220> FEATURE:
<223> OTHER INFORMATION: siRNA

<400> SEQUENCE: 20
ucuggcugga aaggcaacc                                                    19

<210> SEQ ID NO 21
<211> LENGTH: 19
<212> TYPE: RNA
<213> ORGANISM: Artificial Sequence
<220> FEATURE:
<223> OTHER INFORMATION: siRNA

<400> SEQUENCE: 21
gguugccuuu ccagccaga                                                    19

<210> SEQ ID NO 22
<211> LENGTH: 17
<212> TYPE: RNA
<213> ORGANISM: Artificial Sequence
<220> FEATURE:
<223> OTHER INFORMATION: siRNA

<400> SEQUENCE: 22
ggucuggugu augaagg                                                      17

<210> SEQ ID NO 23
<211> LENGTH: 20
<212> TYPE: RNA
<213> ORGANISM: Artificial Sequence
<220> FEATURE:
<223> OTHER INFORMATION: siRNA

<400> SEQUENCE: 23
ccacacauau gccaugguga                                                   20

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
```

```
gatcctaata accccctgac t                                              21

<210> SEQ ID NO 25
<211> LENGTH: 18
<212> TYPE: DNA
<213> ORGANISM: Artificial Sequence
<220> FEATURE:
<223> OTHER INFORMATION: primer

<400> SEQUENCE: 25
cagcatctgc tccaccag                                                  18

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
tcactgccac ccagaagact g                                              21

<210> SEQ ID NO 27
<211> LENGTH: 19
<212> TYPE: DNA
<213> ORGANISM: Artificial Sequence
<220> FEATURE:
<223> OTHER INFORMATION: primer

<400> SEQUENCE: 27
ggatcacctt gcccacagc                                                 19

<210> SEQ ID NO 28
<211> LENGTH: 23
<212> TYPE: DNA
<213> ORGANISM: Artificial Sequence
<220> FEATURE:
<223> OTHER INFORMATION: primer

<400> SEQUENCE: 28
agctgcccga cgcatacagc ccc                                            23

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
accccagggc caggtgtgcc a                                              21

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
tggatttgga cgcattggtc                                                20

<210> SEQ ID NO 31
<211> LENGTH: 21
<212> TYPE: DNA
<213> ORGANISM: Artificial Sequence
```

```
<220> FEATURE:
<223> OTHER INFORMATION: primer

<400> SEQUENCE: 31
tttgcactgg tacgtgttga t                                              21

<210> SEQ ID NO 32
<211> LENGTH: 1849
<212> TYPE: DNA
<213> ORGANISM: Homo sapiens

<400> SEQUENCE: 32 actgagggc accagaggag cagactacaa gaatggcaca cgctatggaa aactcctgga      60
caatcagtaa agagtaccat attgatgaag aagtgggctt tgctctgcca aatccacagg   120
aaaatctacc tgattttat aatgactgga tgttcattgc taaacatctg cctgatctca    180
tagagtctgg ccagcttcga gaaagagttg agaagttaaa catgctcagc attgatcatc   240
tcacagacca caagtcacag cgccttgcac gtctagttct gggatgcatc accatggcat   300
atgtgtgggg caaggtcat ggagatgtcc gtaaggtctt gccaagaaat attgctgttc    360
cttactgcca actctccaag aaactggaac tgcctcctat tttggtttat gcagactgtg   420
tcttggcaaa ctggaagaaa aaggatccta ataagcccct gacttatgag aacatggacg   480 tttgttctc atttcgtgat ggagactgca gtaaggatt cttcctggtc tctctattgg     540
tggaaatagc agctgcttct gcaatcaaag taattcctac tgtattcaag gcaatgcaaa   600
tgcaagaacg ggacactttg ctaaaggcgc tgttggaaat agcttcttgc ttggagaaag   660
cccttcaagt gttccaccaa atccacgatc atgtgaaccc aaaagcattt ttcagtgttc   720
ttcgcatata tttgtctggc tggaaaggca accccagct atcagacggt ctggtgtatg    780
aagggttctg ggaagaccca aaggagtttg caggggcag tgcaggccaa agcagcgtct    840
ttcagtgctt tgacgtcctg ctgggcatcc agcagactgc tggtggagga catgctgctc   900
agttcctcca ggacatgaga agatatatgc caccagctca caggaacttc ctgtgctcat   960
tagagtcaaa tccctcagtc cgtgagtttg tcctttcaaa aggtgatgct ggcctgcggg  1020
aagcttatga cgcctgtgtg aaagctctgg tctcccctgag gagctaccat ctgcaaatcg  1080
tgactaagta catcctgatt cctgcaagcc agcagccaaa ggagaataag acctctgaag  1140
acccttcaaa actggaagcc aaaggaactg gaggcactga tttaatgaat tcctgaaga   1200 ctgtaagaag tacaactgag aaatcccttt tgaaggaagg ttaatgtaac ccaacaagag  1260
cacattttat catagcagag acatctgtat gcattcctgt cattacccat tgtaacagag  1320
ccacaaacta atactatgca atgttttacc aataatgcaa tacaaaagac ctcaaaatac  1380
ctgtgcattt cttgtaggaa acaacaaaa ggtaattatg tgtaattata ctagaagttt   1440
tgtaatctgt atcttatcat tggaataaaa tgacattcaa taaataaaaa tgcataagat  1500
atattctgtc ggctgggcgc ggtggctcac gcctgtaatc ccagcacttt gggaggccga  1560
ggcgggcgga tcacaaggtc aggagatcga gaccatcttg gctaacacgg tgaaaccccg  1620
tctctactaa aaatacaaaa aattagccgg gcgcggtggc gggcacctgt agtcccagct  1680
actcgggagg ctgaggcagg agaatggcgt gaacctggga ggcggagctt gcagtgagcc  1740
aagattgtgc cactgcaatc cggcctgggc taaagagcgg gactccgtct caaaaaaaaa  1800 aaaaaaaga tatattctgt cataataaat aaaaatgcat aagatataa                1849

<210> SEQ ID NO 33
```

```
<211> LENGTH: 1473
<212> TYPE: DNA
<213> ORGANISM: Canis familiaris

<400> SEQUENCE: 33
gtggtcattg gctgtggcaa cctttataat aagtagaggc tctgaaactc tatcagaact      60
aaggaccaaa agaggagact gcaagcatgg aagatgatgg aatacttctt atggaaagtc    120
ctcagagaat ttttgaaaaa taccatatag atgaagagat gggcttcgct ttgccaaatc    180
cactggagaa gctacctccg ccttatgatg aatggatttc cattgctaaa aatctgcctg    240
aactgattaa gaaaaatgaa ctacgtaaaa aagttgatga gttaaaaatt ctcagtattg    300
atggccttag tggacacaag ttgcagcgcc ttgcacgtct ggctctgggg tatatcacca    360
tggcatatgt gtggaatcaa ggtgatggag atgttcgaaa ggtcttgcca cagaatattg    420
ctattcctta ctgtgaactc tctgagaagc tgggtctgcc tcctattctg gtttatgcag    480
actgtgtctt agcaaactgg aagaaaaagg atcccaatgg gcctatgact tatgagaaca    540
tggacattct cttctggttt cctggtggag actgcagtaa aggatttttc ctggtttcac    600
tattggtgga attagcagct gcttctgcaa tcaaagtaat tcccaattta ttaaaggcag    660
ttaaaaatca ggacgaggtc actttgaaga aggcactgca ttatatagct tcttgtctgc    720
accgagccca taaagagttt gaagaagttc ataaacatgt ggacccaagc acgttttca    780 aagttcttcg catatacttg tctggttgga aaggcaactc caaactgcca gagggtttga    840
agtatgaagg tttctgggaa aacccaaaag agtttgcagg aggcagtgca gcccaaagca    900
gcatctttca atgctttgac attctgctgg gcatccagca gtgttctggt gaagaattcg    960
ctgctgaatt cctccaggaa atgagaaact atatgccccc agctcaccgg gactttcttc    1020
tcttgttaaa gtcaggcccc tcagtccggg agtttgttcg ttcaagagat gatgttgaac    1080
tgaaggcaga ttataatgag tgtgtgaaag ctatggtctc cctgagaaaa tatcacttga    1140
agatagtagc taagtacatt gtgattcctg caagccagca gcccaagaat aatcaagcat    1200
ctgaagaatc atcggaacaa aaaaataaag gaactggagg cactaatgcc atggatttcc    1260
tgaagagtgt aagaactaca actgagaaat tcctgctgat agatcattaa tgtaactcaa    1320
acaagggcac attttgtcaa gatgaagatg tctgtatata ttagtgtcac tgctcatgat    1380
atcagaccca tgaattaata gtacacaaca atgttttttt tttacaacaa tgttttaata    1440
gtacttataa aagatttcaa atatttttc caa                                   1473

<210> SEQ ID NO 34
<211> LENGTH: 24
<212> TYPE: RNA
<213> ORGANISM: Homo sapiens

<400> SEQUENCE: 34
agcugcuucu gcaaucaaag uaau                                              24

<210> SEQ ID NO 35
<211> LENGTH: 20
<212> TYPE: DNA
<213> ORGANISM: Homo sapiens

<400> SEQUENCE: 35
atcaccatgg catatgtgtg                                                   20

<210> SEQ ID NO 36
<211> LENGTH: 19
```

```
<212> TYPE: RNA
<213> ORGANISM: Rattus norvegicus

<400> SEQUENCE: 36
gggcuucuuc cucgucucu                                                  19

<210> SEQ ID NO 37
<211> LENGTH: 19
<212> TYPE: RNA
<213> ORGANISM: Rattus norvegicus

<400> SEQUENCE: 37
agagacgagg aagaagccc                                                  19

<210> SEQ ID NO 38
<211> LENGTH: 20
<212> TYPE: DNA
<213> ORGANISM: Homo sapiens

<400> SEQUENCE: 38
gggggacgat cgtcggggggg                                                20

<210> SEQ ID NO 39
<211> LENGTH: 20
<212> TYPE: DNA
<213> ORGANISM: Rattus norvegicus

<400> SEQUENCE: 39
ggggtcaacg ttgagggggg                                                 20

<210> SEQ ID NO 40
<211> LENGTH: 20
<212> TYPE: DNA
<213> ORGANISM: Homo sapiens

<400> SEQUENCE: 40
atcaccatgg catatgtgtg                                                 20

<210> SEQ ID NO 41
<211> LENGTH: 20
<212> TYPE: DNA
<213> ORGANISM: Homo sapiens

<400> SEQUENCE: 41
tgacttatga gaacatggac                                                 20

<210> SEQ ID NO 42
<211> LENGTH: 20
<212> TYPE: DNA
<213> ORGANISM: Homo sapiens

<400> SEQUENCE: 42
tggagactgc agtaaaggat                                                 20

<210> SEQ ID NO 43
<211> LENGTH: 20
<212> TYPE: DNA
<213> ORGANISM: Homo sapiens

<400> SEQUENCE: 43
agctgcttct gcaatcaaag                                                 20

<210> SEQ ID NO 44
```

```
<211> LENGTH: 24
<212> TYPE: DNA
<213> ORGANISM: Homo sapiens

<400> SEQUENCE: 44
agctgcttct gcaatcaaag taat                                              24

<210> SEQ ID NO 45
<211> LENGTH: 19
<212> TYPE: DNA
<213> ORGANISM: Homo sapiens

<400> SEQUENCE: 45
tgattcctgc aagccagca                                                    19

<210> SEQ ID NO 46
<211> LENGTH: 20
<212> TYPE: DNA
<213> ORGANISM: Homo sapiens

<400> SEQUENCE: 46
tcaccatggc atatgtgtgg                                                   20

<210> SEQ ID NO 47
<211> LENGTH: 19
<212> TYPE: DNA
<213> ORGANISM: Homo sapiens

<400> SEQUENCE: 47
tctcatttcg tgatggaga                                                    19

<210> SEQ ID NO 48
<211> LENGTH: 19
<212> TYPE: DNA
<213> ORGANISM: Homo sapiens

<400> SEQUENCE: 48
tctggctgga aaggcaacc                                                    19

<210> SEQ ID NO 49
<211> LENGTH: 17
<212> TYPE: DNA
<213> ORGANISM: Homo sapiens

<400> SEQUENCE: 49
ggtctggtgt atgaagg                                                      17

<210> SEQ ID NO 50
<211> LENGTH: 25
<212> TYPE: DNA
<213> ORGANISM: Artificial Sequence
<220> FEATURE:
<223> OTHER INFORMATION: LEMIDO

<400> SEQUENCE: 50
gggggacgat cgtcgggggg ccccc                                             25

<210> SEQ ID NO 51
<211> LENGTH: 29
<212> TYPE: DNA
<213> ORGANISM: Artificial Sequence
<220> FEATURE:
<223> OTHER INFORMATION: LEMIDO

<400> SEQUENCE: 51
```

```
tcgtcgtttt gtcgttttgt cgttccccc                                29

<210> SEQ ID NO 52
<211> LENGTH: 27
<212> TYPE: DNA
<213> ORGANISM: Artificial Sequence
<220> FEATURE:
<223> OTHER INFORMATION: LEMIDO

<400> SEQUENCE: 52
tcgtcgtttt cggcgcgcgc cgccccc                                  27
```